United States Patent
Pitlick et al.

(10) Patent No.: US 12,161,629 B2
(45) Date of Patent: Dec. 10, 2024

(54) METHODS AND COMPOSITIONS FOR TREATMENT OF GLAUCOMA AND RELATED CONDITIONS

(71) Applicant: Opus Genetics, Inc., Farmington Hills, MI (US)

(72) Inventors: William H. Pitlick, Seattle, WA (US); Alan R. Meyer, North Riverside, IL (US); Mina Sooch, Bloomfield, MI (US); Konstantinos Charizanis, Ypsilanti, MI (US)

(73) Assignee: Opus Genetics, Inc., Farmington Hills, MI (US)

( * ) Notice: Subject to any disclaimer, the term of this patent is extended or adjusted under 35 U.S.C. 154(b) by 707 days.

(21) Appl. No.: 17/283,038

(22) PCT Filed: Oct. 15, 2019

(86) PCT No.: PCT/US2019/056324
§ 371 (c)(1),
(2) Date: Apr. 6, 2021

(87) PCT Pub. No.: WO2020/081562
PCT Pub. Date: Apr. 23, 2020

(65) Prior Publication Data
US 2021/0346350 A1  Nov. 11, 2021

Related U.S. Application Data

(60) Provisional application No. 62/752,088, filed on Oct. 29, 2018, provisional application No. 62/745,806, filed on Oct. 15, 2018.

(51) Int. Cl.
| | |
|---|---|
| *A61K 31/417* | (2006.01) |
| *A61K 9/00* | (2006.01) |
| *A61K 31/138* | (2006.01) |
| *A61K 31/222* | (2006.01) |
| *A61K 31/27* | (2006.01) |
| *A61K 31/382* | (2006.01) |
| *A61K 31/4045* | (2006.01) |
| *A61K 31/4164* | (2006.01) |
| *A61K 31/4168* | (2006.01) |
| *A61K 31/4178* | (2006.01) |
| *A61K 31/439* | (2006.01) |
| *A61K 31/444* | (2006.01) |

(Continued)

(52) U.S. Cl.
CPC .......... *A61K 31/417* (2013.01); *A61K 9/0048* (2013.01); *A61K 31/138* (2013.01); *A61K 31/222* (2013.01); *A61K 31/27* (2013.01); *A61K 31/382* (2013.01); *A61K 31/4045* (2013.01); *A61K 31/4164* (2013.01); *A61K 31/4168* (2013.01); *A61K 31/4178* (2013.01); *A61K 31/439* (2013.01); *A61K 31/444* (2013.01); *A61K 31/4704* (2013.01); *A61K 31/472* (2013.01); *A61K 31/475* (2013.01); *A61K 31/496* (2013.01); *A61K 31/498* (2013.01); *A61K 31/517* (2013.01); *A61K 31/5377* (2013.01); *A61K 31/55* (2013.01); *A61K 31/551* (2013.01); *A61K 31/5575* (2013.01); *A61K 31/558* (2013.01); *A61K 31/683* (2013.01); *A61K 31/7076* (2013.01); *A61K 45/06* (2013.01); *A61P 27/06* (2018.01)

(58) Field of Classification Search
CPC .... A61K 31/138; A61K 31/222; A61K 31/27; A61K 31/382; A61K 31/4045; A61K 31/4164; A61K 31/4168; A61K 31/4178; A61K 31/439; A61K 31/444; A61K 31/4704; A61K 31/472; A61K 31/475; A61K 31/496; A61K 31/498; A61K 31/517; A61K 31/5377; A61K 31/55; A61K 31/551; A61K 31/5575; A61K 31/558; A61K 31/683; A61K 31/7076; A61K 45/06; A61K 9/0048; A61P 27/06
See application file for complete search history.

(56) References Cited

U.S. PATENT DOCUMENTS

| | | |
|---|---|---|
| 4,252,721 A | 2/1981 | Silvestrini et al. |
| 4,443,441 A | 4/1984 | Galin |

(Continued)

FOREIGN PATENT DOCUMENTS

| | | |
|---|---|---|
| CN | 101463009 A | 6/2009 |
| CN | 103764120 A | 4/2014 |

(Continued)

OTHER PUBLICATIONS

Constant et al., AMA Arch. Ophthalmol., 1956, 56(1), p. 19-25. (Year: 1956).*
Shin et al., Journal of Korean Oriental Medicine, 2010, 31(3), p. 1-7. (Year: 2010).*
Russo et al., Clinical Ophthalmology, 2008, 2(4), p. 897-905. (Year: 2008).*
Perry et al., Drugs Aging, 2003, 20, p. 597-630. (Year: 2003).*
Kogure et al., "Hypotensive effect of labetalol on intraocular pressure in rabbits: in relation to its alpha- and beta-adrenergic blocking action on the cardiovascular system", Arch Int Pharmacodyn Ther., Mar. 1981, 250(1):109-122. (Abstract only).

(Continued)

*Primary Examiner* — Jonathan S Lau
(74) *Attorney, Agent, or Firm* — Dechert LLP

(57) ABSTRACT

Methods, compositions and kits comprising alpha-adrenergic antagonists, such as phentolamine, for the treatment of glaucoma, ocular hypertension, and/or other ocular disorders, such as non-arteritic anterior ischemic optic neuropathy or keratoconus, are provided. Said methods, compositions and kits may further comprise additional therapeutic agents, including prostaglandin analogues such as latanoprost, beta-adrenergic antagonists, alpha-adrenergic agonists, carbonic anhydrase inhibitors, cholinergic agonists, NMDA receptor antagonist, adenosine receptor antagonists, 5-HT2a receptor agonists, or Rho kinase inhibitors.

20 Claims, 1 Drawing Sheet

(51) Int. Cl.
  *A61K 31/4704* (2006.01)
  *A61K 31/472* (2006.01)
  *A61K 31/475* (2006.01)
  *A61K 31/496* (2006.01)
  *A61K 31/498* (2006.01)
  *A61K 31/517* (2006.01)
  *A61K 31/5377* (2006.01)
  *A61K 31/55* (2006.01)
  *A61K 31/551* (2006.01)
  *A61K 31/5575* (2006.01)
  *A61K 31/558* (2006.01)
  *A61K 31/683* (2006.01)
  *A61K 31/7076* (2006.01)
  *A61K 45/06* (2006.01)
  *A61P 27/06* (2006.01)

(56) References Cited

U.S. PATENT DOCUMENTS

| | | |
|---|---|---|
| 4,508,715 A | 4/1985 | Booth et al. |
| 4,515,295 A | 5/1985 | Dougherty |
| 4,590,202 A | 5/1986 | Remy |
| 4,629,456 A | 12/1986 | Edwards |
| 4,659,714 A | 4/1987 | Watt-Smith |
| 4,834,727 A | 5/1989 | Cope |
| 4,888,344 A | 12/1989 | Sunagawa et al. |
| 4,906,613 A | 3/1990 | Watkins |
| 4,938,970 A | 7/1990 | Hustead et al. |
| 5,032,392 A | 7/1991 | Varma |
| 5,059,188 A | 10/1991 | Goddard |
| 5,134,124 A | 7/1992 | Nisato et al. |
| 5,149,320 A | 9/1992 | Dhaliwal et al. |
| 5,192,527 A | 3/1993 | Abrahmsohn |
| 5,261,903 A | 11/1993 | Dhaliwal et al. |
| 5,281,591 A | 1/1994 | Burke |
| 5,288,759 A | 2/1994 | DeSantis, Jr. |
| 5,488,050 A | 1/1996 | Neufeld |
| 5,514,118 A | 5/1996 | Kummer et al. |
| 5,584,823 A | 12/1996 | Valberg |
| 5,591,426 A | 1/1997 | Dabrowski et al. |
| 5,627,611 A | 5/1997 | Scheiner |
| 5,792,767 A | 8/1998 | Meyer et al. |
| 5,885,550 A | 3/1999 | Vallier |
| 5,891,882 A | 4/1999 | Meyer et al. |
| 5,891,913 A | 4/1999 | Sallmann et al. |
| 5,895,654 A | 4/1999 | Hartford et al. |
| 6,001,845 A | 12/1999 | Estok |
| 6,025,396 A | 2/2000 | Kim et al. |
| 6,043,224 A | 3/2000 | Lee et al. |
| 6,046,207 A | 4/2000 | Meyer et al. |
| 6,051,594 A | 4/2000 | Lowrey |
| 6,106,866 A | 8/2000 | Ranney |
| 6,291,498 B1 | 9/2001 | Horn |
| 6,420,407 B1 | 7/2002 | Horn |
| 6,432,401 B2 | 8/2002 | Weber et al. |
| 6,469,065 B1 | 10/2002 | Garvey et al. |
| 6,515,006 B2 | 2/2003 | Horn |
| 6,638,537 B2 | 10/2003 | Dennis et al. |
| 6,730,065 B1 | 5/2004 | Horn |
| 6,730,691 B1 | 5/2004 | Galin |
| 6,764,678 B2 | 7/2004 | Weber et al. |
| 6,872,390 B2 | 3/2005 | Weber et al. |
| 7,229,630 B2 | 6/2007 | Chen et al. |
| 7,569,230 B2 | 8/2009 | Chen et al. |
| 7,575,757 B2 | 8/2009 | Chen et al. |
| 7,868,035 B2 | 1/2011 | Woodward et al. |
| 8,299,079 B2 | 10/2012 | Kaufman |
| 8,445,526 B2 | 5/2013 | Horn |
| 8,580,787 B2 | 11/2013 | Horn |
| 8,597,629 B1 | 12/2013 | Horn |
| 8,889,112 B2 | 11/2014 | Horn |
| 8,979,809 B2 | 3/2015 | Horn |
| 9,089,560 B2 | 7/2015 | Meyer |
| 9,789,088 B2 | 10/2017 | Meyer |
| 9,795,560 B2 | 10/2017 | Meyer |
| 9,968,594 B2 | 5/2018 | Horn et al. |
| 10,064,818 B2 | 9/2018 | Horn et al. |
| 10,278,918 B2 | 5/2019 | Meyer |
| 10,507,245 B2 | 12/2019 | Vejarano Restrepo |
| 10,610,518 B2 | 4/2020 | Robinson et al. |
| 10,639,297 B2 | 5/2020 | Feinbaum et al. |
| 10,772,829 B2 | 9/2020 | Meyer |
| 10,993,932 B2 | 5/2021 | Pitlick et al. |
| 11,000,509 B2 | 5/2021 | Meyer |
| 11,090,261 B2 | 8/2021 | Meyer |
| 2002/0082288 A1 | 6/2002 | Horn |
| 2002/0183356 A1 | 12/2002 | Weber et al. |
| 2002/0183396 A1 | 12/2002 | Weber et al. |
| 2002/0187986 A1 | 12/2002 | Horn |
| 2003/0236306 A1 | 12/2003 | Chen et al. |
| 2004/0053894 A1 | 3/2004 | Mazess et al. |
| 2004/0176408 A1 | 9/2004 | Horn |
| 2005/0080056 A1 | 4/2005 | Horn |
| 2005/0203099 A1 | 9/2005 | Chen et al. |
| 2006/0211753 A1 | 9/2006 | Horn |
| 2006/0257388 A1 | 11/2006 | Knowles |
| 2007/0098748 A1 | 5/2007 | Chen et al. |
| 2008/0020076 A1 | 1/2008 | Jhamandas et al. |
| 2008/0039507 A1 | 2/2008 | Woodward et al. |
| 2009/0131303 A1 | 5/2009 | Hong et al. |
| 2009/0220618 A1 | 9/2009 | Xia et al. |
| 2009/0232763 A1 | 9/2009 | Kabra et al. |
| 2010/0029663 A1 | 2/2010 | Horn |
| 2010/0324031 A1 | 12/2010 | Kabra |
| 2011/0152274 A1 | 6/2011 | Kaufman |
| 2011/0178147 A1 | 7/2011 | Likitlersuang et al. |
| 2012/0136072 A1 | 5/2012 | Mosher et al. |
| 2012/0149748 A1 | 6/2012 | Shanler et al. |
| 2012/0208858 A1 | 8/2012 | Shanler et al. |
| 2012/0238615 A1 | 9/2012 | Chow et al. |
| 2012/0277239 A1 | 11/2012 | Horn et al. |
| 2013/0029919 A1 | 1/2013 | Gore et al. |
| 2013/0143938 A1 | 6/2013 | Horn |
| 2013/0172357 A1 | 7/2013 | Horn |
| 2014/0221445 A1 | 8/2014 | Meyer |
| 2014/0221446 A1 | 8/2014 | Meyer |
| 2015/0150848 A1 | 6/2015 | Horn |
| 2016/0008278 A1 | 1/2016 | Horn et al. |
| 2016/0008337 A1 | 1/2016 | Horn et al. |
| 2016/0051515 A1 | 2/2016 | Meyer |
| 2017/0065664 A1 | 3/2017 | Russ |
| 2018/0221274 A1 | 8/2018 | Meyer |
| 2018/0221340 A1 | 8/2018 | Meyer |
| 2019/0254963 A1 | 8/2019 | Meyer |
| 2019/0321337 A1 | 10/2019 | Robinson et al. |
| 2019/0358152 A1 | 11/2019 | Meyer |
| 2020/0246310 A1 | 8/2020 | Pitlick et al. |
| 2020/0253931 A1 | 8/2020 | Pitlick et al. |
| 2021/0338638 A1 | 11/2021 | Meyer |
| 2021/0346349 A1 | 11/2021 | Pitlick et al. |

FOREIGN PATENT DOCUMENTS

| | | |
|---|---|---|
| EP | 0399791 A1 | 11/1990 |
| EP | 2242487 B1 | 2/2016 |
| WO | WO-1995005188 A1 | 2/1995 |
| WO | WO-1999007353 A1 | 2/1999 |
| WO | WO-2001019364 A1 | 3/2001 |
| WO | WO-2001085171 A1 | 11/2001 |
| WO | WO-2005034998 A2 | 4/2005 |
| WO | WO-2005123093 A2 | 12/2005 |
| WO | WO-2007008666 A2 | 1/2007 |
| WO | WO-2008009141 A1 | 1/2008 |
| WO | WO-2010135731 A1 | 11/2010 |
| WO | WO-2011050018 A1 | 4/2011 |
| WO | WO-2011050030 A1 | 4/2011 |
| WO | WO-2012075319 A2 | 6/2012 |
| WO | WO-2012112566 A1 | 8/2012 |
| WO | WO-2012119059 A1 | 9/2012 |
| WO | WO-2012119070 A2 | 9/2012 |
| WO | 2013003827 A2 | 1/2013 |
| WO | WO-2013115844 A1 | 8/2013 |

(56) References Cited

FOREIGN PATENT DOCUMENTS

| WO | WO-2013130577 A2 | 9/2013 |
|----|------------------|--------|
| WO | WO-2014121027 A1 | 8/2014 |
| WO | WO-2014121028 A1 | 8/2014 |
| WO | WO-2017152129 A2 | 9/2017 |

OTHER PUBLICATIONS

Sakanaka et al., "Ocular pharmacokinetic/pharmacodynamic modeling for multiple anti-glaucoma drugs", Biol Pharm Bull., Aug. 2008, 31(8):1590-1595.

Abdelkader, A. and Kaufman, H. E., "Clinical outcomes of combined versus separate carbachol and brimonidine drops in correcting presbyopia," *Eye and Vision*, 3(1), 31 (2016).

Ackerman, S.L. et al., "Low-dose brimonidine for relief of ocular redness: Integrated analysis of four clinical trials," *Clinical and Experimental Optometry*, 102(2), 131-139 (2019).

Akutsu, H. et al., "Contrast Sensitivity and Reading Through Multifocal Intraocular Lenses," *Arch Ophthalmol*, 110:1076-1080 (1992).

Al-Khersan, H. et al., "Retinal Detachments Associated With Topical Pilocarpine Use for Presbyopia," *Am J Ophthalmol.* (2022)doi:10.1016/j.ajo.2022.05.011.

Alio, J.L., and Azar, D.T., "Management of Complications in Refractive Surgery," *Springer* (2018).

Amarikwa, L. et al., "Vitreofoveal Traction Associated With Pilocarpine for Presbyopia," *Ophthalmic Surg Lasers Imaging Retina.*, 53(7):410-411. doi: 10.3928/23258160-20220629-01 (Jul. 2022).

American Optometric Association. Adult Vision: 41 to 60 Years of Age (2022).

American Society of Health System Pharmacists; AHFS Drug Information 2010. Bethesda, MD, p. 1386 (2010).

Antonelli-Incalzi, R. and Pedone, C., "Respiratory effects of beta-adrenergic receptor blockers," *Curr Med Chem.*, 14(10), 1121-1128 (2007). doi:10.2174/092986707780362853.

Applegate, R.A. et al., "Metrics of retinal image quality predict visual performance in eyes with 20/17 or better visual acuity," *Optom Vis Sci.*, 83(9) 635-640 (2006).

Bellucci, R. et al., "Visual acuity and contrast sensitivity comparison between Tecnis and Acrysof AS60 AT intraocular lenses," *J. Cataract Refract Surg.*, 31:712-717 (2005).

Besada, E. et al., "Pupillometry Study of Brimonidine Tartrate 0.2% and Apraclonidine 0.5%," *The Journal of Clinical Pharmacology*, 51(12), 1690-1695 (2011).

Betoptic Pilo PI (2006).

Bidgoli, S.and Alio, J.L., "Night Vision Disturbances Following Refractive Surgery: Causes, Prevention, and Treatment," (2018).

Boger, W.P. et al., "Clinical Trial Comparing Timolol Ophthalmic Solution to Pilocarpine in Open-Angle Glaucoma," *American Journal of Ophthalmology*, 86(1), 8-18 (1978).

Boland, M.V. et al., "Electronic monitoring to assess adherence with once-daily glaucoma medications and risk factors for nonadherence: the automated dosing reminder study," *JAMA Ophthalmol*, 132(7), 838-844 (2014), doi:10.1001/jamaophthalmol.2014.856.

Boyer, D. et al., "Phentolamine Ophthalmic Solution Rapidly Reverses Pharmacologically Induced Mydriasis in Two Pivotal Phase 3 MIRA Trials," ASRS Annual Meeting, Abstract ID 665511 (2022).

Bradley, A.E. et al., "International Harmonization of Nomenclature and Diagnostic Criteria (INHAND): Nonproliferative and Proliferative Lesions of the Rabbit," *J Toxicol Pathol.* 34(3 Suppl):183S-292S (2021).

British Journal of Ophthalmology, European Glaucoma Society Terminology and Guidelines for Glaucoma, 4th Edition—Chapter 3: "Treatment Principles and Options . . . " *Br J Ophthalmol.* 101(6):130-195, BJO (2017). [No authors listed].

Brooks et al., "Patient subjective visual function after corneal collagen crosslinking for keratoconus and corneal ectasia," *J Cataract Refract Surg.*, 38(4),615-619 (2012), doi:10.1016/j.jcrs.2011.11.029.

Bruner, R.H. et al., "Spontaneous hibernomas in Sprague-Dawley rats," *Toxicol Pathol.*, 37(4):547-52 (2009), doi:10.1177/0192623309335061.

Brunton, L. et al., "Goodman & Gilman's Pharmacological Basis of Therapeutics, 12e," *McGraw-Hill Education/Medical* (2011).

Büscher, R. et al., "Comparison of guinea-pig, bovine and rat alpha 1-adrenoceptor subtypes," *Br J Pharmacol.*, 117(4):703-711 (1996).

Cankurtaran, V. and Tekin, K., "Effects of a Single Dose of Topical Brimonidine 0.15% on Anterior Segment Morphology, Pupil Characteristics, and Choroidal Thickness in Healthy Subjects," *Eye & Contact Lens: Science & Clinical Practice*, 47(6), 323-329 (2001), https://doi.org/10.1097/ICL.0000000000000708.

Canovetti, A. et al., "Aceclidine, brimonidine tartrate, and dapiprazole: Comparison of miotic effect and tolerability under different lighting conditions," *Journal of Cataract and Refractive Surgery*, 35(1), 42-46 (2009), https://doi.org/10.1016/j.jcrs.2008.09.009.

CDRH FDA Tecnis Multifocal IOL: P080010: CDRH/FDA, "Summary of Safety and Effectiveness," (2009)https://www.accessdata.fda.gov/cdrh_docs/pdf8/P080010B.pdf.

CDRH/FDA, "Summary of Safety and Effectiveness of VISX STAR Excimer Laser System," (2007).

Chu, Y.R. et al., "The Safety of Phentolamine Ophthalmic Solution for Reversal of Pharmacologically Induced Mydriasis from Multiple Late-Stage Clinical Trials," ASCRS Annual Meeting, Paper ID 80618 (2022).

Chylak, L.T. et al., "Loss of contrast sensitivity in diabetic patients with LOCSII classified cataracts," *Brit J Ophthalmol.*, 77:78-11 (1993).

Csaky, K.G. et al., "Report from the NEI/FDA ophthalmic clinical trial design and endpoints symposium," *Invest Ophth Vis Sci.* 49(2) 479-489 (2008).

Dart, R.C., *Medical Toxicology*, 3 ed., Lippincott Williams & Wilkins. Philadelphia, PA, 719 (2004).

De La Torre, J.C. et al., "Impaired Cerebromicrovascular Perfusion," *Annals of the New York Academy of Sciences*, Jan. 25, 2006.

Deeb, S.E. et al., "Evaluation of monolithic C18 HPLC columns for the fast analysis of pilocarpine hydrochloride in the presence of its degradation products," *Die Pharmazie*, 9, 751-756 (2006).

DeGraff, A.C. et al., "Phentolamine," *American Heart J*, 92:397-402 (1976) doi:10.1016/s0002-8703(76)80121-4.

Devries, D. et al., "Phentolamine Ophthalmic Solution Reverses Pharmacologically Induced Mydriasis in Healthy Subjects: Subgroup Analyses in the Pivotal Phase 3 MIRA-2 Randomized Placebo Controlled Trial," ARVO Annual Meeting, Abstract ID 3709630 (2022).

Dexl, A.K. et al., "Reading performance after implantation of a small-aperture corneal inlay for the surgical correction of presbyopia: Two-year follow-up," *J Cataract Refract Surg*, 37(3), 525-531 (2011) doi:10.1016/j.jcrs.2010.10.044.

Dick, H.B. et al., "Contrast sensitivity after implantation of toric iris-claw lenses in phakic eyes," *J Cataract Refract Surg.*, 30:2284-2289 (2004).

Diestelhorst, M. et al., "Combined Therapy of Pilocarpine or Latanoprost with Timolol Versus Latanoprost Monotherapy," *Survey of Ophthalmology*, 47, S155-S161 (2002) https://doi.org/10.1016/S0039-6257(02)00329-6.

Dinsmore, W.W. and Alderdice, D.K., "Vasoactive intestinal polypeptide and phentolamine mesylate administered by autoinjector in the treatment of patients with erectile dysfunction resistant to other intracavernosal agents," *Brit J Urology*, 81:437-440 (1988).

Dragoi, V., "Ocular Motor System. In: Neuroscience Online: An Electronic Textbook for the Neurosciences," The University of Texas Health Science Center at Houston (2020).

Draize, J.H. et al., "Methods for the study of irritation and toxicity of substances applied topically to the skin and mucous membranes," *J Pharmacol Exp Ther* , 82:377-390 (1944).

Draize, J.H., "Appraisal of the Safety of Chemicals in Foods, Drugs and Cosmetics," *The Association of Food and Drug Officials of the United States*, 49-51 (1955).

Drews-Bankiewiez, M. et al., "Contrast Sensitivity in Patients with Nuclear Cataracts," *Arch. Ophthalmol*, 110: 953-959 (1992).

Drugbank Online, "Phentolamine" https://go.drugbank.com/drugs/DB00692 Accessed Aug. 25, 2022.

(56) References Cited

OTHER PUBLICATIONS

Drum, B. et al., "Assessment of visual performance in the evaluation of new medical products," In: *Drug Discoveries Today: Technologies*, Lam K, Timmerman H, eds. Elsevier., 4(2) 55-61 (2007).

Du, H. et al., "Cell membrane chromatography competitive binding analysis for characterization of α1A adrenoreceptor binding interactions," *Anal Bioanal Chem.*, 400(10):3625-3633 (2011) https://pubmed.ncbi.nlm.nih.gov/21544540/.

Durand-Cavagna, G. et al., "Spontaneous pre-Descemet's membrane corneal opacities in rabbits," *Lab Anim Sci*, 48(3):310-3 (1998).

Elliott, D.B. et al., "Improvements in clinical and functional vision and perceived visual disability after first and second eye cataract surgery," *Brit J Ophthalmol.*, 81:889-895 (1997).

Elliott, D.B. et al., "The reliability of the Pelli-Robson chart," *Ophthalmology and Physiological Optics.*, 10:21-24 (1990).

Enroth-Cugell et al., "The contrast sensitivity of retinal ganglion cells of the cat.," *J Physiol.*, 187:517-552 (1966).

Eton, E.A. et al., "Rhegmatogenous Retinal Detachment Following Initiation of Pilocarpine Hydrochloride Ophthalmic Solution 1.25% for Treatment of Presbyopia," *Ophthalmic Surg Lasers Imaging Retina.*, 53(7):410-411 (2022) doi: 10.3928/23258160-20220629-01.

European Glaucoma Society Terminology and Guidelines for Glaucoma, 4th Edition—Chapter 3, "Treatment principles and options," *Br J Ophthalmol*, 101(6):130-95 (2017).

Eydelman, M. et al., "Symptoms and Satisfaction of Patients in the Patient-Reported Outcomes With Laser In Situ Keratomileusis (PROWL) Studies," *JAMA Ophthalmol.*, 135(1):13-22 (2017).

Fan, T.Y. et al., "Improved high-performance liquid chromatographic determination of pilocarpine and its degradation products in ophthalmic solutions importance of octadecylsilane col. choice," *Journal of Chromatography A*, 740(2):289-295 (1996). doi: 10.1016/0021-9673(96)00120-3.

Fan-Paul, N. et al., "Night vision disturbances after corneal refractive surgery," *Surv Ophthalmol*, 47(6), 533-546 (2002). doi:10.1016/s0039-6257(02)00350-8.

Fejer, T.P. et al., "Night myopia: implications for the young driver," *Can J Ophthalmol*, 27(4), 172-176, (1992) Retrieved from https://www.ncbi.nlm.nih.gov/pubmed/1633588.

Foster, S. et al., "MIRA-4, Clinical Trial Evaluating the Safety and Efficacy of Phentolamine Ophthalmic Solution for Reversal of Pharmacologically Induced Mydriasis in Pediatric Subjects Aged 3-11 Years," AAOpt Annual Meeting, Abstract ID 10569 (2022).

Fricke, T. R. et al., "Global Prevalence of Presbyopia and Vision Impairment from Uncorrected Presbyopia: Systematic Review, Meta-analysis, and Modelling," *Ophthalmology*, 125(10), 1492-1499 (2018), doi:10.1016/j.ophtha.2018.04.013.

Ginsburg, A.P., "Contrast sensitivity and functional vision in Functional Vision," In Packer, M, editor. *Functional Vision*. Philadelphia (PA) Lippincott Williams & Wilkins, 5-15. (Int. Ophthalmol Clin, vol. 43) (2003).

Ginsburg, A.P., "Contrast sensitivity: determining the visual quality and function of cataract, intraocular lenses and refractive surgery," *Curr Opin Ophthalmol.*, 17:19-26 (2006).

Ginsburg, A.P., "Vision Channels, Contrast Sensitivity and Functional Vision in Human Vision and Electronic Imaging IX," Rogowitz, BE, ed. SPIE-IS&T, 529:215-25 (2004).

Giovannitti, J.A., Jr. et al., "Alpha-2 adrenergic receptor agonists: a review of current clinical applications," *Anesth Prog*, 62(1), 31-39 (2015).

Godbillon J., "Determination of the major metabolite of phentolamine in human plasma and urine by high performance liquid chromatography," *J Chromatography.*, 222:461-466 (1981).

Goel, M. et al., "Aqueous humor dynamics: a review," *Open Ophthalmol J*, 4, 52-59 (2010), doi:10.2174/1874364101004010052.

Goertz, A.D. et al., "Review of the impact of presbyopia on quality of life in the developing and developed world," *Acta Ophthalmol.*, 92(6):497-500 (2014).

Goldstein, I., "Oral phentolamine: an alpha-1, alpha-2 adrenergic antagonist for the treatment of erectile dysfunction," *Int J Impot Res.*, 12(S1):S75-S80 (2000).

Gomez-Gomar, A. et al., "HPLC method for the simultaneous determination of pilocarpine, isopilocarpine, pilocarpic acid and isopilocarpic acid," *Journal of Pharmaceutical and Biomedical Analysis.*, 7(12):1729-1734 (1989), doi:10.1016/0731-7085(89)80187-6.

Hays, R.D. et al., "Assessment of the Psychometric Properties of a Questionnaire Assessing Patient-Reported Outcomes With Laser In Situ Keratomileusis (PROWL)," *JAMA Ophthalmol.* 135(1):3-12 (2017).

Hersh, E.V. et al., "Phase Four, Randomized, Double-Blinded, Controlled Trial of Phentolamine Mesylate in Two- to Five-year-old Dental Patients," *Pediatr Dent*, 39(1), 39-45 (2017).

Hersh, E.V. et al., "Phentolamine mesylate for accelerating recovery from lip and tongue anesthesia," *Dent Clin North Am*, 54:631-642. doi: 10.1016/j.cden.2010.06.004 (2010).

Hill, C.E. et al., "Specificity of innervation of iris musculature by sympathetic nerve fibres in tissue culture," *Pflugers Arch*, 361(2), 127-134 (1976), doi:10.1007/BF00583456.

Holladay, J.T. et al., "Functional vision and corneal changes after laser in situ keratomileusis determined by contrast sensitivity, glare testing and corneal topography," *J Cataract Refract Surg.*, 25:664-669 (1999).

Holladay, J.T. et al., "Phentolamine Mesylate Ophthalmic Solution Once Daily Reduces Pupil Diameter and Improves Night Vision Disturbances," AAO Annual Meeting, PA025 (2018).

Holve, D., "Optical Coherence Tomography and Slit Lamp Imaging of Corneal Dystrophy in the Dutch Belted Rabbit," Unpublished data, 2023.

Hong, D., "Tropicamide," [Updated Jul. 4, 2020]. In: StatPearls [Internet]. Treasure Island (FL): StatPearls Publishing (2020).

Howe, J.W., "The objective assessment of contrast sensitivity function by electrophysiological means," *Brit J Ophthalmology.*, 68:626-638 (1984).

Ishikawa, H. et al., "Comparison of post-junctional alphaadrenoceptors in iris dilator muscle of humans, and albino and pigmented rabbits," *Naunyn Schmiedebergs Arch Pharmacol*, 354(6), 765-772 (1996), doi:10.1007/BF00166903.

Isopto, Isopto® Carpine (Pilocarpine Hydrochloride Ophthalmic Solution) FDA Documents 1%, 2% and 4%. Highlights of Prescribing Information (2010).

Israilov, S. et al., "Intracavernous injections for erectile dysfunction in patients with cardiovascular diseases and failure or contraindications for sildenafil citrate," *Intl J Impot Res.*, 14:38-43 (2002).

Jackson, M. et al., "A Combination of Phentolamine Eye Drops and Low Dose Pilocarpine Improves Near Vision in VEGA-1 Phase 2 Presbyopia Trial," AAO (2022).

Jin, B. et al., "Degradation Characteristics of a Novel PAF Receptor Antagonist, SY0916, in Aqueous Solution." *Journal of Analytical Methods in Chemistry*, vol. 2019, Article ID 8789470, 8 pages (2019), https://doi.org/10.1155/2019/8789470.

Kan, X., "UPLC-MS/MS Determination of Phentolamine in Human Plasma and its Application to a Pharmacokinetic Study," *Drug Res* (Stuttg), 64(11):607-612 (2014), doi:10.1055/s-0033-1364002.

Kannarr, S. et al., "LYNX-1: A Pivotal Phase 3 Randomized Placebo-Controlled Trial of Phentolamine Ophthalmic Solution in Subjects with Dim Light Vision Disturbance," AAOpt Annual Meeting, Abstract ID 10526 (2022).

Karpecki, P.M. et al., "Phentolamine eye drops reverse pharmacologically induced mydriasis in a randomized phase 2b trial," *Optom Vis Sci.*, 98(3):234-242 (2021).

Kass, M A. et al., "The Ocular Hypertension Treatment Study: a randomized trial determines that topical ocular hypotensive medication delays or prevents the onset of primary open-angle glaucoma," *Arch Ophthalmol*, 120(6), 701-713; discussion 829-730 (2002), doi: 10.1001/archopht.120.6.701.

Kato, C.O.S. et al., "Effects of brimonidine tartrate 0.1% ophthalmic solution on the pupil, refraction, and light reflex," *Sci Rep.*, 8(1):9003 (2018), doi: 10.1038/s41598-018-27436-8.

(56) References Cited

OTHER PUBLICATIONS

Katz, J. et al., " VEGA-1: Phentolamine Ophthalmic Solution as a Single Agent Improves Distance-Corrected Near Visual Acuity in Patients with Presbyopia," ARVO Annual Meeting, Abstract ID 3712883 (2022).
Kennedy, "High-performance liquid chromatographic analysis of pilocarpine hydrochloride, isopilocarpine, pilocarpic acid and isopilocarpic acid in eye-drop preparations," *Journal of Chromatography A*, 212(3), 331-338, ISSN 0021-9673 (1981), https://doi.org/10.1016/S0021-9673(01)84046-2.
Kerger, B.D. et al., "An assay for phentolamine using high performance liquid chromotography with electrochemical detection," *Analyt Biochem*, 170:145-151 (1988) doi: 10.1016/0003-2697(88)90102-9.
Kesler A. et al., "Effect of brimonidine tartrate 0.2% ophthalmic solution on pupil size," Journal of Cataract and Refractive Surgery 30(8):1707-1710 (2004), doi:10.1016/j.jers.2004.02.043.
Kiel, J.W. and Reitsamer, H.A., "Paradoxical effect of phentolamine on aqueous flow in the rabbit," *J Ocul Pharmacol Ther*, 23(1), 21-26 (2007), doi:10.1089/jop.2006.0102.
Kimlin, J.A. et al., "Nighttime Driving in Older Adults: Effects of Glare and Association With Mesopic Visual Function," *Invest Ophthalmol Vis Sci*, 58(5), 2796-2803 (2017), doi:10.1167/iovs.16-21219.
Kinney, M., "Temporal Effects of 2% Pilocarpine Ophthalmic Solution on Human Pupil Size and Accommodation," *Military Medicine*, 185(Supplement_1):435-442 (2020), doi:10.1093/milmed/usz235.
Kirsten, R. et al., "Clinical pharmacokinetics of vasodilators. Part II," *Clin Pharmacokinet*, 35(1):9-36 (1998), doi: 10.2165/00003088-199835010-00002.
Klein, B.E. et al., "Prevalence of glaucoma. The Beaver Dam Eye Study," Ophthalmology, 99(10), 1499-1504 (1992), doi:10.1016/s0161-6420(92)31774-9.
Kobayashi, H. et al., "Efficacy of bunazosin hydrochloride 0.01% as adjunctive therapy of latanoprost or timolol," *J Glaucoma* 13(1), 73-80 (2004), doi:10.1097/00061198-200402000-00014.
Konno, F. and Takayanagi, I., "Characterization of postsynaptic alpha-1 adrenoceptors in the rabbit iris dilator smooth muscle," *Naunyn Schmiedebergs Arch Pharmacol* 333:271-276 (1986), doi: 10.1007/BF00512940.
Koss, M.C., & Gherezghiher, T., "Pharmacological characterization of alphaadrenoceptors involved in nictitating membrane and pupillary responses to sympathetic nerve stimulation in cats," *Naunyn Schmiedebergs Arch Pharmacol*, 337(1), 18-23 (1988), doi:10.1007/BF00169471.
Krupin, T. et al., "Effect of prazosin on aqueous humor dynamics in rabbits," *Arch Ophthalmol*, 98(9), 1639-1642 (1980), doi:10.1001/archopht.1980.01020040491021.
Kupersmith, M.J. et al., "Contrast sensitivity loss in multiple sclerosis," *Invest Ophthalmol Vis Sci.*, 25:632-639 (1984).
Kwon, Y.H. et al., "Primary open-angle glaucoma," *N Engl J Med*, 360(11), 1113-1124 (2009), doi:10.1056/NEJMra0804630.
Lai, J.S. et al., "The efficacy and safety of combined phacoemulsification, intraocular lens implantation, and limited goniosynechialysis, followed by diode laser peripheral iridoplasty, in the treatment of cataract and chronic angle-closure glaucoma," *J Glaucoma.*, 10(4):309-15 (2001), doi: 10.1097/00061198-200108000-00011. PMID: 11558816.
Langevin, N.E. et al., "Historical Data: Histopathology Lesions Observed in the Eyes of Control Rabbits in Topical Ocular Administration and Contact Lens Studies," *Toxicologic Pathology* 46(7): 799-820 (2018).
Lee, J.H. et al., "Efficacy of brimonidine tartrate 0.2% ophthalmic solution in reducing halos after laser in situ keratomileusis," *Journal of Cataract and Refractive Surgery*, 34(6):963-967 (2008), doi:10.1016/j.jers.2008.01.028.
Lewis, R.A. et al., "Fixed-dose combination of AR-13324 and latanoprost: A double-masked, 28-day, randomised, controlled study in patients with open-angle glaucoma or ocular hypertension," *Br. J. Ophthalmol.* 100, 339-344 (2016).

Lin et al., "Pharmacokinetics Study of Phentolamine Mesylate Injection in Healthy Volunteers. In Sichuan da xue xue bao. Yi xue ban = *Journal of Sichuan University*," Medical science edition, 49 (6), 929-933 (2018).
Liu, J.C., "Assessing the utility of 2.5% phenylephrine for diagnostic pupillary dilation," *Can J Ophthalmol*, 52(4), 349-354 (2017), doi:10.1016/j.jcjo.2017.01.023.
Lograno, M.D. and Reibaldi, A., "Receptor-responses in fresh human ciliary muscle," *Br J Pharmacol*, 87(2), 379-385 (1986), doi:10.1111/j.1476-5381.1986.tb10827.
Marshall, L.L. et al., "Therapy for Open-Angle Glaucoma.," *Consult Pharm*, 33(8), 432-445 (2018), doi:10.4140/TCP.n.2018.432.
Martinez, C.E. et al., "Effect of pupillary dilation on corneal optical aberrations after photorefractive keratectomy," *Arch Ophthalmol*, 116(8), 1053-1062 (1998), doi:10.1001/archopht.116.8.1053.
Marx-Gross, S. et al., "Brimonidine versus dapiprazole: Influence on pupil size at various illumination levels," *Journal of Cataract and Refractive Surgery*,31(7):1372-1376.(2005) doi:10.1016/j.jcrs.2004.12.064.
Matsuura, K. et al., "Determination of pilocarpine in aqueous humour by liquid chromatography-atmospheric pressure chemical ionization mass spectrometry," *Journal of Chromatography B: Biomedical Sciences and Applications*, 621(2):173-180, (1993)doi:10.1016/0378-4347(93)80093-J.
McAuliffe-Curtin, D. and Buckley, C., "Review of alpha adrenoceptor function in the eye," *Eye* 3:472-476 (1989), doi: 10.1038/eye.1989.71.
McDonald, M. et al., "MIRA-3: A 2nd Phase 3 Randomized Placebo-Controlled Trial of Phentolamine Ophthalmic Solution to Reverse Pharmacologically Induced Mydriasis," ASCRS Annual Meeting, Paper ID 81993 (2022).
McDonald, M.B. et al., "Phentolamine mesylate treatment of severe night-vision complaints," Presented at: Annual Meeting of the American Society of Cataract and Refractive Surgery; Mar. 25-29, 2011; San Diego, CA.
McDonald, M.B. et al., "Phentolamine Mesylate Treatment of Severe Night Vision Complaints," AAO Abstracts, PO433 (2010).
McDonnell, P.J. et al., "Associations of presbyopia with vision-targeted health-related quality of life," *Arch Ophthalmol*, 121(11), 1577-1581 (2003), doi:10.1001/archopht.121.11.1577.
McMahon, C.G., "A pilot study of the role of intracavernous injection of vasoactive intestinal peptide (VIP) and phentolamine mesylate in the treatment of erectile dysfunction," *Int J Impot Res.*, 4:233-6 (1996).
Mittag, T.W. et al., "Alpha-adrenergic antagonists: correlation of the effect on intraocular pressure and on alpha 2-adrenergic receptor binding specificity in the rabbit eye," *Exp Eye Res*, 40(4), 591-599 (1985), doi:10.1016/0014-4835(85)90081-8.
Mohammadpour, M. et al., "Updates on Managements for Keratoconus," *J Curr Ophthalmol*, 30(2):110-124 (2018).
Molinari, J.F. et al., "Dapiprazole clinical efficiency for counteracting tropicamide 1%," *Optom Vis Sci*, 71(5), 319-322 (1994), doi:10.1097/00006324-199405000-00003.
Molinari, J.F. et al., in *Optom Vis Sci* (1994) vol. 71(5), p. 319 (Abstract).
Monestam, E. and Lundqvist, B., "Long-time results and associations between subjective visual difficulties with car driving and objective visual function 5 years after cataract surgery," *J Cataract Refract Surg*, 32(1), 50-55. (2006), doi:10.1016/j.jcrs.2005.06.052.
Montes-Mico, R. et al., "Choice of spatial frequency for contrast sensitivity evaluation after corneal refractive surgery," *J. Refract. Surg.*, 17:646-651 (2001).
Montes-Mico, R. et al., "Visual performance with multifocal intraocular lenses: Mesopic contrast sensitivity under distance and near conditions," *Ophthalmology* 111:85-96 (2004).
Moore, C.P. et al., "Anterior Corneal Dystrophy of American Dutch Belted Rabbits: Biomicroscopic and Histopathologic Findings," *Vet. Pathol.*, 24:28-33 (1987).
Moore, P.A. et al., "Pharmacokinetics of lidocaine with epinephrine following local anesthesia reversal with phentolamine mesylate," In *Anesth. Prog.* 55(2);40-48. (2008), DOI: 10.2344/0003-3006(2008)55[40:POLWEF]2.0.CO;2.

(56) References Cited

OTHER PUBLICATIONS

Motolko, M.A. and Phelps, C.D., "Contrast sensitivity in asymmetric glaucoma," *Int Ophthalmol.*, 7(1):45-59 (1984).
Nagasubramanian, S.A., "Comparison of the Ocular Hypotensive Efficacy, Safety and Acceptability of Brimonidine 0.2% Twice Daily Versus Pilocarpine 2.0% Thrice Daily as Adjunct Therapy with Beta-Blockers," In: *Glaucoma Update VI. Springer Berlin Heidelberg*, 203-208 (2000), doi:10.1007/978-3-642-57056-8_31.
Nakamura, S. et al., "Evaluation of alpha-1 adrenoceptors in the rabbit iris: pharmacological characterization and expression of mRNA," *Br J Ophthalmol*, 127:1367-1374 (1999). doi: 10.1038/sj.bjp.0702675.
National Center for Biotechnology Information (2022). PubChem Compound Summary for CID 517293, Phentolamine, methane sulfonate, 2022.
National Center for Biotechnology Information (2022). PubChem Compound Summary for CID 91430, Phentolamine mesylate, 2022.
National Institutes of Health. "NIH urges dilated eye exams to detect glaucoma," Accessed Apr. 24, 2020. https://www.nih.gov/news-events/news-releases/nih-urges-dilated-eye-exams-detect-glaucoma.
Neonatal Intensive Care, Children's Hospital, Neonatal Intensive Care Unit, May 26, 2011.
Nielsen, C.B. and Nielsen, P.J., "Effect of alpha- and beta-receptor active drugs on corneal thickness," *Acta Ophthalmol (Copenh)*, 63(3), 351-354 (1985), doi:10.1111/j.1755-3768.1985.tb06819.x.
Noordam, A. et al., "Quantitative Determination of Pilocarpine, Isopilocarpine, Pilocarpic Acid, and Isopilocarpic Acid in Clinical Ophthalmic Pilocarpine Formulations by Reversed-Phase Liquid Chromatography," *Journal of Pharmaceutical Sciences.*, 70(1):96-97 (1981), doi:10.1002/jps.2600700122.
Nyman, N., Optometrist *; Keates, Edwin U. "Physicant. Effects of Dapiprazole on the Reversal of Pharmacologically Induced Mydriasis," *Optometry and Vision Science*: 67(9):705-709 (1990).
Ogura, T. et al., "Properties of [3H]bunazosin binding in rat kidney," *Clin Ther.*, 10(5):559-567 (1988).
OraVerse Summary Basis of Approval (SBA). Clinical pharmacology and biopharmaceutics review. Application No. 22-159; 2007. Novalar. https://www.accessdata.fda.gov/drugsatfda_docs/nda/2008/022159s000_ClinPharmR.
Oraverse, "OraVerse (phentolamine mesylate) FDA Documents injection," Highlights of Prescribing Information. Septodont (2016a).
Oraverse, OraVerse FDA Documents. FDA approves OraVerse for pediatric dental patients 3 years and older. Septodont (2016b).
Oshika, T. et al., "Effect of bunazosin hydrochloride on intraocular pressure and aqueous humor dynamics in normotensive human eyes," *Arch Ophthalmol*, 109(11), 1569-1574, (1991). doi:10.1001/archopht.1991.01080110105046.
Oshika, T. et al., "Incidence of intraoperative floppy iris syndrome in patients on either systemic or topical alpha(1)-adrenoceptor antagonist," *Am. J. Ophthalmol.* 143, 150-151 (2007).
Owsley, C. and Sloane, M.E., "Contrast sensitivity, acuity, and the perception of 'real-world' targets," Brit J Ophthalmology., 71:791-796 (1987).
Owsley, C., "Contrast Sensitivity," *Ophthalmol Clin N Am*, 16:171-177 (2003).
Padma-Nathan, H. et al., "Long-term safety and efficacy of oral phentolamine mesylate (Vasomax) in men with mild to moderate erectile dysfunction," *Int J Impot Res*, 14(4), 266-270 (2002), doi:10.1038/sj.ijir.3900885.
Park, S.Y. et al., "Clinical Efficacy of Pinhole Soft Contact Lenses for the Correction of Presbyopia," *Semin Ophthalmol*, 34(2), 06-114 (2019), doi:10.1080/08820538.2019.1586966.
Pepose, J. (2021c), "Phase 2 Clinical Trial to Evaluate the Efficacy of Phentolamine Ophthalmic Solution and Low-Dose Pilocarpine for the Treatment of Presbyopia," AAO Annual Meeting. Abstract ID 30068457.

Pepose, J. et al. (2022a), "Phentolamine Ophthalmic Solution as a Single Agent Improves Distance-Corrected Near Visual Acuity in Patients with Presbyopia, " ASCRS Annual Meeting, Paper ID 80665.
Pepose, J. et al. (2022b), "VEGA-1: Phentolamine Ophthalmic Solution in combination with Low Dose Pilocarpine Improves Distance-Corrected Intermediate Visual Acuity in Patients with Presbyopia," ARVO Annual Meeting, Abstract ID 3707817.
Pepose, J., et al., "A randomized phase 2 clinical trial of phentolamine mesylate eye drops in patients with severe night vision disturbances," *BMC Ophthalmol.* Oct 8;22(1):402, 2022, doi: 10.1186/s12886-022-02621-6.
Pepose, J.P. et al., "Phentolamine mesylate ophthalmic solution provides long lasting pupil modulation and improves visual acuity," The Association for Research in Vision and Ophthalmology Meeting (2020).
Pepose, J.S. et al., "Phentolamine mesylate ophthalmic solution provides lasting pupil modulation and improves near visual acuity in presbyopic glaucoma patients in a randomized phase 2b clinical trial," *Clin Ophthalmol.* 15:79-91 (2020) doi: 10.2147/OPTH.S278169. eCollection 2021.
Pepose, J.S., et al. (2021b) "Phase 2 Clinical Trial to Evaluate the Efficacy of Phentolamine Ophthalmic Solution and Low-Dose Pilocarpine for the Treatment of Presbyopia. Paper #76645," The American Society of Cataract and Refractive Surgery Meeting.
Pepose, J.S. et al., (2021a). "Phase 3 clinical trial to evaluate the efficacy of phentolamine ophthalmic solution on the reversal of pharmacologically induced mydriasis Paper #76599," The American Society of Cataract and Refractive Surgery Meeting.
Peter, J.V.S. et al., "Pharmacokinetics of Pilocarpine in Subjects with Varying Degrees of Renal Function," *Journal of Clinical Pharmacology*, 40(12 Pt 2):1470-1475 (2000).
Pop, M. and Payette, Y., "Risk factors for night vision complaints after LASIK for myopia," *Ophthalmology*, 111(1), 3-10 (2004), doi:10.1016/j.ophtha.2003.09.022.
Poulet, F.M. et al., "Development of hibernomas in rats dosed with phentolamine mesylate during the 24-month carcinogenicity study," *Toxicol Pathol*, 32(5), 558-566 (2004), doi:10.1080/01926230490505086.
Prata, T.S. et al., "Iris morphologic changes related to alpha (1) adrenergic receptor antagonists: implications for intraoperative floppy iris syndrome," *Ophthalmology*, 116:877-81 (2009).
Puell, M.C. et al., "Mesopic contrast sensitivity in the presence or absence of glare in a large driver population," *Graefes Arch Clin Exp Ophthalmol*, 242(9), 755-761 (2004) doi:10.1007/s00417-004-0951-6.
Radi, Z. et al., "Comparative pathophysiology, toxicology, and human cancer risk assessment of pharmaceutical-induced hibernoma," *Toxicol Appl Pharmacol*, 273(3), 456-463 (2013), doi:10.1016/j.taap.2013.10.011.
Rahman, M.Q. et al., "Brimonidine for glaucoma," *Expert Opinion on Drug Safety*;9(3):483-491 (2010), doi:10.1517/14740331003709736.
Regan, D. et al., "Visual acuity and contrast sensitivity in multiple sclerosis—hidden visual loss: an auxiliary diagnostic test," *Brain.*, 100(3):563-79 (1977).
Regitine, Novartis Pharmaceuticals Corporation, "Regitine—phentolamine mesylate injection, powder, lyophilized, for suspension; labeling," (1998).
Regitine, Regitine FDA Documents. Highlights of Prescribing Information (1998).
Rengstorff, R.H. and Doughty, C. B., "Mydriatic and cycloplegic drugs: a review of ocular and systemic complications," *Am J Optom Physiol Opt*, 59(2), 162-177 (1982).
Rev-Eyes Ophthalmic Eyedrops 0.5% (Bausch & Lomb), *Drug Reference Encyclopedia*, 2007.
REV-EYES. Federal Register; 78(92):27971, "Determination that REV-EYES (dapiprazole hydrochloride ophthalmic solution), 0.5%, was not withdrawn from sale for reasons of safety or effectiveness," (2013).
Rev-Eyes® dapiprazole hydrochloride ophthalmic solution 0.5%. NDA 019849, Dec. 31, 1990.
Rhopressa, Rhopressa pharmacology/toxicology NDA review and evaluation. *United States Food and Drug Administration* (2017).

(56) References Cited

OTHER PUBLICATIONS

Richards, D.A. et al., "Circulatory and alpha-adrenoceptor blocking effects of phentolamine," *Br J Clin Pharmacol* 5(6):507-513 (1978), doi: 10.1111/j.1365-2125.1978.tb01665.
Ridder, W.H. et al., "Contrast Sensitivity and Tear Layer Aberrometry in Dry Eye Patients," *Optometry and Vision Sciences*, 86:E1059-1068 (2009).
Robin, A.L. et al., "Adherence in glaucoma: objective measurements of once-daily and adjunctive medication use," *Am J Ophthalmol*, 144(4), 533-540 (2007), doi:10.1016/j.ajo.2007.06.012.
Romero-Jimenez, M. et al., "Keratoconus: a review," *Cont Lens Anterior Eye*, 33(4), 57-166; quiz 205, (2010)doi:10.1016/j.clae.2010.04.006.
Rosen, Emanuel S., "FRCSE Night vision disturbance," *Journal of Cataract & Refractive Surgery*., 31(2):247-9 (2005).
Rutherford, B. et al., "Local and systemic toxicity of intraoral submucosal injections of phentolamine mesylate (OraVerse)," *Anesth Prog*, 56(4), 123-127 (2009), doi:10.2344/0003-3006-56.4.123.
Rutkowski, P.C. and Thompson, H.S., "Mydriasis and Increased Intraocular Pressure," *Arch Ophthalmol.* 87(1 ):21-24 (1972).
Sandoval, H.P. et al., "Comparison of visual outcomes, photopic contrast sensitivity, wavefront analysis, and patient satisfaction following cataract extraction and IOL implantation," *Eye.*, 22:1469-1475 (2008).
Schallhorn, et al., "Comparison of night driving performance after wavefront-guided and conventional LASIK for moderate myopia," *Ophthalmology*, 116(4), 702-709 (2009), doi:10.1016/j.ophtha.2008.12.038.
Septodont Holding (2016): Approved Product Labeling for ORAVERSE (phentolamine mesylate; 0.4mg/1.7mL) for injection. NDA 022159, Mar. 2016. Available online at https://www.accessdata.fda.gov/drugsatfda_docs/label/2016/022159s011lbl.pdf, checked on Apr. 27, 2022.
Serle, J.B. et al., "Two Phase 3 Clinical Trials Comparing the Safety and Efficacy of Netarsudil to Timolol in Patients With Elevated Intraocular Pressure: Rho Kinase Elevated IOP Treatment Trial 1 and 2 (ROCKET-1 and ROCKET-2)," *Am J Ophthalmol.*, 186:116-27 (2017).
Shah, B. et al., "Influence of thymoxamine eye-drops on the mydriatic effect of tropicamide and phenylephrine alone and in combination," *Ophthalmic Physiol Opt*, 9(2), 153-155 (1989), doi:10.1111/j.1475-1313.1989.tb00835.
Shemesh, G. et al., "Effect of brimonidine tartrate 0.10% ophthalmic solution on pupil diameter," *Journal of Cataract and Refractive Surgery*, 37(3):486-489 (2011), doi:10.1016/j.jers.2010.09.026.
Sherwood, M.B. et al., "Twice-Daily 0.2% Brimonidine-0.5% Timolol Fixed-Combination Therapy vs Monotherapy With Timolol or Brimonidine in Patients With Glaucoma or Ocular Hypertension," *Arch. Ophthalmol.* 124, 1230 (2006).
Shiau, T. et al., "The role of episcleral venous pressure in glaucoma associated with Sturge-Weber syndrome," *J AAPOS*, 16(1), 61-64 (2012), doi:10.1016/j.jaapos.2011.09.014.
Shiose, Y. et al., "Epidemiology of glaucoma in Japan—a nationwide glaucoma survey," *Jpn J Ophthalmol*, 35(2), 133-155 (1991).
Silva, L.F.G. et al., "Phentolamine bioequivalence study," *In Int. J Clin. Pharmacol. Ther* 42 (1), pp. 43-49 (2004).
Sioufi, A. et al., "Gas chromatographic determination of phentolamine (Regitine®) in Human Plasma," *J Chromat* 222429-435 (1981), doi: 10.1016/s0378-4347(00)84143-2.
Sommer, A. et al., "Relationship between intraocular pressure and primary open angle glaucoma among white and black Americans," The Baltimore Eye Survey. *Arch Ophthalmol*, 109(8), 1090-1095 (1991), doi:10.1001/archopht.1991.01080080050026.
Steiner, T.F., "State of independent optometry: optometry dominates primary eyecare," *Review of Optometric Business* (2013).
Steinhauer, S.R. et al., "Sympathetic and parasympathetic innervation of pupillary dilation during sustained processing," *Int J Psychophysiol*, 52(1), 77-86 (2004), doi:10.1016/j.ijpsycho.2003.12.005.
Sternitzke, K.D. et al., "High-performance liquid chromatographic determination of pilocarpitie hydrochloride and its degradation products using a /l-cyclodextrin column," *Journal of Chromatography*, 0(589):159-164 (1992), doi: 10.1016/0021-9673(92)80017.
Suzuki, F. et al., "Distribution of alpha-1 adrenoceptor subtypes in RNA and protein in rabbit eyes," *Br J Ophthalmol*, 135:600-608 (2002), doi: 10.1038/sj.bjp.0704503.
Takayanagi, I. et al., "Alpha 1B-adrenoceptor mechanisms in rabbit iris dilator." *Jpn J Pharmacol*, 59(3), 301-305 (1992), doi:10.1254/jjp.59.301.
Tang, W. et al., "Visual performance of lasik patients," *Ann Acad Med Singapore*, 35:541-6 (2006).
Tanzer, J.M. et al., "A Pharmacokinetic and Pharmacodynamic Study of Intravenous Pilocarpine in Humans," *J Dent Res.* 74(12):1845-1849 (1995), doi: 10.1177/00220345950740120701.
Taylor, S.H. et al., "The circulatory effects of phentolamine in man," *Circulation*, 31:741-754 (1965), doi: 10.1161/01.cir.31.5.741.
Tham, Y. C. et al., "Global prevalence of glauco ma and projections of glaucoma burden through 2040: a systematic review and meta-analysis," *Ophthalmology*, 121(11), 2081-2090 (2014), doi:10.1016/j.ophtha.2014.05.013.
Thomas, J., "Normal and amblyopic contrast sensitivity functions in central and peripheral retinas," *Invest. Ophthalmol Visual Sci.* 17:746-753 (1978).
Thordsen, J.E. et al., "Miotic effect of brimonidine tartrate 0.15% ophthalmic solution in normal eyes," *Journal of Cataract and Refractive Surgery*, 30(8):1702-1706 (2004), doi:10.1016/j.jcrs.2003.12.037.
Trew, D. R. et al., "Ocular responses in healthy subjects to topical bunazosin 0.3%—an alpha 1—adrenoceptor antagonist," *Br J Ophthalmol*, 75(7), 411-413 (1991), doi: 10.1136/bjo.75.7.411.
"Rev-Eyes™," Thomson PDR for Ophthalmic Medicines. 2003;258.
Abad et al., "Comparison of astigmatism correction using shorter arc length 90°/120° asymmetric intacs severe keratoconus versus 150° single-segment intacs severe keratoconus in asymmetric keratoconus," Cornea. Nov. 2011;30(11):1201-6.
Abelson et al., "The Truth about Tachyphylaxis," Rev Ophthalmol. 2006;13(3):112-5.
ACETADOTE (acetylcysteine) injection. Highlights of Prescribing Information, 2008.
ACULAR® (ketorolac tromethamine ophthalmic solution) 0.5%. Highlights of Prescribing Information, 2012.
Anastasi et al., "Effect of pilocarpine in counteracting mydriasis," Arch Ophthalmol. Jun. 1968;79(6):710-5.
ASA, "K-max Plus: Technical attributes and Typical Analysis", 2011.
Barbee and Smith, "A comparative study of mydriatic and cycloplegic agents; in human subjects without eye disease," Am J Ophthalmol. Nov. 1957;44(5 Pt 1):617-22.
Batawi and Micieli, "Adie's tonic pupil presenting with unilateral photophobia successfully treated with dilute pilocarpine," BMJ Case Rep. Jan. 2, 2020;13(1):e233136.
Benson and Seifert, "Is phentolamine stable in solution with papaverine," J Urol. Nov. 1988;140(5):970-1.
Betagan® Eye Drops. Consumer Medicine Information, 2010.
Bristol-Myers Squibb Company, "MUCOMYST® (acetylcysteine solution, USP)", 2006.
CCI, "Glycerin, Anhydrous (Glycerol), ACS," Safety Data Sheet. Aug. 7, 2012.
CCI, "Mannitol, (D-)," Safety Data Sheet. Jul. 30, 2012.
CLARINEX® (desloratadine) Tablets, RediTabs®, and Oral Solution. Highlights of Prescribing Information, 2015.
Cohen and Zakov, "The diagnosis of Adie's pupil using 0.0625% pilocarpine solution," Am J Ophthalmol. May 1975;79(5):883-5.
Doughty and Lyle, "A review of the clinical pharmacokinetics of pilocarpine, moxisylyte (thymoxamine), and dapiprazole in the reversal of diagnostic pupillary dilation," Optom Vis Sci. May 1992;69(5):358-68.
Doughty and Lyle, "A review of the clinical pharmacokinetics of pilocarpine, moxisylyte (thymoxamine), and dapiprazole in the reversal of diagnostic pupillary dilation," Optom Vis Sci. May 1992;69(5):358-68(abstract).

(56) References Cited

OTHER PUBLICATIONS

Drummond, "The effect of light intensity and dose of dilute pilocarpine eyedrops on pupillary constriction in healthy subjects," Am J Ophthalmol. Aug. 15, 1991;112(2):195-9.
Edgar et al., "Effects of dipivefrin and pilocarpine on pupil diameter, automated perimetry and LogMAR acuity," Graefes Arch Clin Exp Ophthalmol. Feb. 1999;237(2):117-24.
European Search Report from European Patent Application 14746208.9, dated Jun. 21, 2016.
Examination Report from European Patent Application 14746208.9, dated Jan. 31, 2018.
Gambill et al., "Mydriatic effect of four drugs determined with pupillograph," Arch Ophthalmol. Jun. 1967;77(6):740-6.
Geyer et al., "The additive miotic effects of dapiprazole and pilocarpine," Graefes Arch Clin Exp Ophthalmol. Jul. 1995;233(7):448-51.
Gilmartin et al., "Reversal of tropicamide mydriasis with single instillations of pilocarpine can induce substantial pseudo-myopia in young adults," Ophthalmic Physiol Opt. Sep. 1995;15(5):475-9.
Hadzija et al., "Physicochemical stability of papaverine hydrochloride-phentolamine mesylate mixtures used for intracavernous injection: a preliminary evaluation," J Urol. Jul. 1, 1988;140(1):64-5.
Hara et al., "Bunazosin, a selective alpha1-adrenoceptor antagonist, as an anti-glaucoma drug: effects on ocular circulation and retinal neuronal damage," Cardiovasc Drug Rev. Spring 2005;23(1):43-56.
Hogan et al. "Dose-response study of dapiprazole HCl in the reversal of mydriasis induced by 2.5% phenylephrine," J Ocul Pharmacol Ther. Aug. 1997;13(4):297-302.
Jacobson and Olson, "Influence of pupil size, anisocoria, and ambient light on pilocarpine miosis. Implications for supersensitivity testing," Ophthalmology. Feb. 1993;100(2):275-80.
Johnston, "Relief for Patients Troubled by Night-Vision Complaints: Presented at AAO," PeerVoice. Oct. 21, 2010.
Leavitt et al., "Pupillary response to four concentrations of pilocarpine in normal subjects: application to testing for Adie tonic pupil," Am J Ophthalmol. Mar. 2002;133(3):333-6.
Martell, "Chelates of Ascorbic Acid Formation and Catalytic Properties," Adv Chem. Jun. 1, 1982;200:153-87.
Muftuoglu et al., "Drug-induced intraocular lens movement and near visual acuity after AcrySof intraocular lens implantation," J Cataract Refract Surg. Jul. 2005;31(7):1298-305.
Murphy et al., "How red is a white eye? Clinical grading of normal conjunctival hyperaemia, " Eye (Lond). May 2007;21(5):633-8.
National Institutes of Health, "Visual acuity test," Retrieved Feb. 23, 2015: medlineplus.gov/ency/article/003396.htm.
Notice of Intention to Grant a Patent from European Patent Application 14746208.9, dated Apr. 10, 2019.
Ocuphire Pharma, Inc., "Safety and Efficacy of Ophthalmic Phentolamine Mesylate in Glaucoma," Study NCT03960866. May 23, 2019.
Ocuphire Pharma, Inc., "Safety and Efficacy of Ophthalmic Phentolamine Mesylate in Glaucoma," Study NCT03960866. Oct. 14, 2019.
Ocuphire Pharma, Inc., "Safety and Efficacy of Ophthalmic Phentolamine Mesylate to Reverse Pharmacologically Induced Mydriasis," Study NCT04024891. Oct. 14, 2019.
Ocuphire Pharma, Inc., "Safety and Efficacy of Ophthalmic Phentolamine Mesylate to Reverse Pharmacologically Induced Mydriasis," Study NCT04024891. Start Jul. 2019.
Ocuphire Pharma, Inc., "Single Dose Study of Phentolamine Mesylate Eye Drops in Patients With Severe Night Vision Disturbances (SNV)," Study NCT04004507. Aug. 1, 2019.
OraVerse (phentolamine mesylate) Injection. Highlights of Prescribing Information, 2009.
Ozulken et al., "Effect of topical pilocarpine on refractive surgery outcomes," Int Ophthalmol. Mar. 2020;40(3):733-740.
PCT International Search Report and Written Opinion from PCT/US2014/014067, dated Apr. 18, 2014.
PCT International Search Report and Written Opinion from PCT/US2014/014070, dated Mar. 24, 2014.
Ramsay, "Dilute solutions of phenylephrine and pilocarpine in the diagnosis of disordered autonomic innervation of the iris. Observations in normal subjects, and in the syndromes of Horner and Holmes-Adie," J Neurol Sci. Mar. 1986;73(1):125-34.
Smith et al., "An increased effect of pilocarpine on the pupil by application of the drug in oil," Br J Ophthalmol. May 1978; 62(5): 314-317.
Soli et al., "Vasoactive cocktails for erectile dysfunction: chemical stability of PGE1, papaverine and phentolamine," J Urol. Aug. 1998; 160(2):551-5.
Thompson, "Adie's syndrome: some new observations," Trans Am Ophthalmol Soc. 1977; 75: 587-626.
Troy et al., "Remington: The Science and Practice of Pharmacy," University of the Sciences, Philadelphia, Pennsylvania, 2006;21st ed.:1032.
Tu et al., "Stability of papaverine hydrochloride and phentolamine mesylate in injectable mixtures," Am J Hosp Pharm. 1987;44:2524-7.
Vivacy, "Stylage," retrieved May 27, 2016.
Wang et al., "Degradation kinetics of phentolamine hydrochloride in solution," J Pharm Sci. Nov. 1988;77(11):972-6.
Zimmerman, "Pilocarpine," Ophthalmology. Jan. 1981;88(1):85-8.
Chao, R. and Clowers, D. E. "Experience with Intracavernosal Tri-Mixture for the Management of Neurogenic Erectile Dysfunction," *Arch. Phys. Med. Rehab.* 1994, vol. 75, Issue 3, p. 276-278.
Doucette, W. et al. "Adrenergic modulation of olfactory bulb circuitry affects odor discrimination," *Learning & Memory*, 2007, vol. 14, p. 539-547.
International Search Report and Written Opinion for PCT/US2019/056324, dated Jan. 28, 2020.
Kostyuchenkov, V.N. "Effect of Phentolamine on the Ophthalmotone," *Farmikol i Toksikol*, 1970, vol. 33, Issue 5, p. 569-572.
National Health and Medical Research Council, "A Guide to Glaucoma for Primary Health Care Providers—A companion document to NHMRC Guidelines for the screening, prognosis, diagnosis, management and prevention of glaucoma", 2011.
Tsukamoto, H. et al. "Additive effect of bunazosin on intraocular pressure when topically added to treatment with latanoprost in patients with glaucoma," *Jap. J. Ophthalmol*. 2003, vol. 47, Issue 3, p. 526-528.

\* cited by examiner

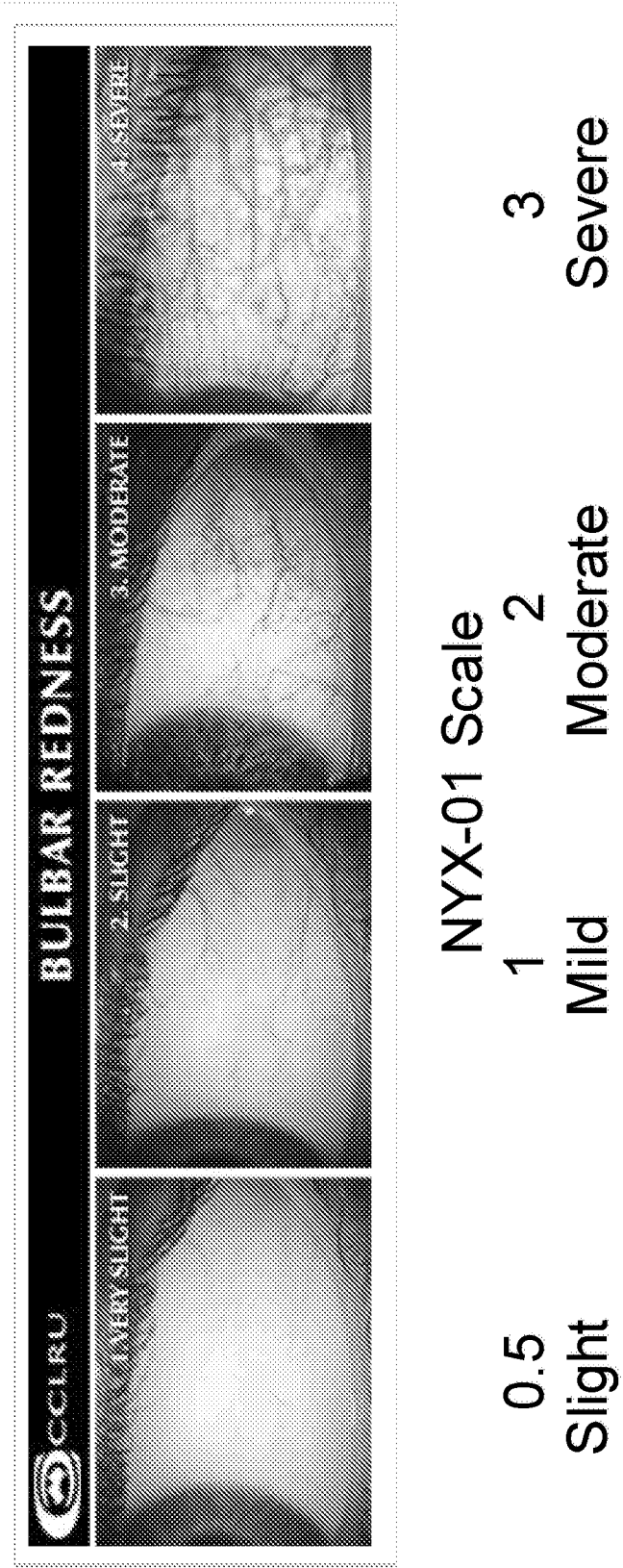

METHODS AND COMPOSITIONS FOR TREATMENT OF GLAUCOMA AND RELATED CONDITIONS

CROSS-REFERENCE TO RELATED APPLICATIONS

This application is the national stage of International (PCT) Patent Application Serial No. PCT/US2019/056324, filed Oct. 15, 2019, which claims the benefit of and priority to U.S. Provisional Patent Application Ser. No. 62/745,806, filed Oct. 15, 2018, and U.S. Provisional Patent Application Ser. No. 62/752,088, filed Oct. 29, 2018; the contents of each of which are hereby incorporated by reference in their entirety.

FIELD OF THE INVENTION

The invention provides methods, compositions, and kits containing an alpha-adrenergic antagonist, such as phentolamine, for treating patients suffering from glaucoma, ocular hypertension, and/or other ocular disorders.

BACKGROUND

Glaucoma is a disease of the eye that often affects the retina and/or optic nerve and, if left untreated, can lead to blindness. Various forms of glaucoma are described in the literature, such as congenital, open-angle, closed-angle, primary, and secondary glaucoma. Prolonged periods of elevated intraocular pressure are a common characteristic of many forms of glaucoma. Such prolonged periods of elevated intraocular pressure can result in irreversible damage to the retina and optic nerve, resulting in progressive, permanent vision loss. Ocular hypertension is a condition characterized by elevated intraocular pressure, and can be present in patients where no apparent vision loss has yet occurred. Treatments that reduce intraocular pressure provide benefits to suffering from ocular hypertension and/or glaucoma.

Existing drug therapies to reduce intraocular pressure are not effective for all patients and/or have undesirable side effects. For example, certain prostaglandin analogs can cause temporary or permanent darkening or pigmentation of the periorbital skin, eyelashes, and iris hyperemia, and/or ocular itching. Beta blockers can have effects on pulmonary tissue, leading to the possibility of cardiac side effects as well as hypertension, increased reactivity to allergens, and/or decreased visual acuity. Miotic agents, such as pilocarpine, can cause headaches and undesired visual effects, such as blurry vision and visual impairment (e.g., dim, dark, "jumping" vision), which can limit the ability of patients to perform certain activities, such as driving an automobile during low light conditions, such as night time. Certain orally administered carbonic anhydrase inhibitors, such as acetazolamide, can cause metabolic acidosis, fatigue, and/or dyspepsia. Certain compounds having alpha adrenergic agonistic activity (such as brimonidine and trabodenoson) can cause allergic conjunctivitis, hyperemia, and/or itchy eyes. Further, various existing drug therapies for reducing intraocular pressure have the undesired feature that the agents must be administered to the patient more than once a day given due to the relatively short duration efficacy of the drug.

Additional classes of therapeutic agents that have been described for treatment of glaucoma include rho kinase inhibitors, adenosine receptor agonists, NMDA receptor antagonists, and 5-$HT_{2A}$ receptor agonists. Rho kinase inhibitors can leave corneal deposits (verticillata), reduce the patient's visual acuity, and/or cause eye redness lasting for a duration of many hours up to a day.

Bunazosin has been described in the literature as an alpha-adrenoceptor antagonist potentially useful as a therapeutic agent for treatment of glaucoma. See, for example, Hara et al. in *Cardiovascular Drug Reviews* (2005) vol. 23(1), pages 43-56. It was reported that bunazosin decreased intraocular pressure in patients. Id. However, not all alpha-adrenoceptor antagonists cause a reduction in intraocular pressure in patients. For example, the alpha-adrenoceptor antagonist dapiprazole hydrochloride has been reported to not significantly alter intraocular pressure in normotensive eyes or in eyes with elevated intraocular pressure. Accordingly, there remains a need for additional safe and effective methods and compositions for treating glaucoma, ocular hypertension, and/or other ocular disorders.

The present invention addresses the aforementioned need for methods and compositions for treating patients suffering from glaucoma, ocular hypertension, and other ocular disorders while minimizing undesirable side effects, and the invention provides other related advantages.

SUMMARY

The invention provides methods, compositions, and kits containing an alpha-adrenergic antagonist, such as phentolamine, for treating patients suffering from glaucoma, ocular hypertension, and/or other ocular disorders. The alpha-adrenergic antagonist, such as phentolamine, is administered topically to the eye of the patient, preferably in the form of a liquid aqueous ophthalmic formulation. Desirably the alpha-adrenergic antagonist is administered to the patient once daily in order to reduce intraocular pressure in the eye of the patient, such as to achieve a reduction in intraocular pressure of at least 10%, 20% or more. Such reduction in intraocular pressure due to the alpha-adrenergic antagonist provides therapeutic benefits to patients suffering from glaucoma, ocular hypertension, and/or other ocular disorders. One benefit of therapeutic methods described herein is that the patient may also experience an improvement in visual performance. Such improvement in the patient's ability to see clearly, as well as ability to distinguish between an object and its background, is a benefit in addition to the therapeutic benefits provided for treating glaucoma, ocular hypertension, and/or other ocular disorders. Exemplary aspects and embodiments of the invention are described below.

One aspect of the invention provides a method of treating a condition selected from the group consisting of glaucoma, ocular hypertension, and non-arteritic anterior ischemic optic neuropathy in a patient while minimizing eye redness during the patient's waking hours. The method comprises administering to an eye of a patient in need thereof at or near the bedtime of the patient an effective amount of a once daily dosage of phentolamine or a pharmaceutically acceptable salt thereof to thereby treat the condition. The once daily dosage may be administered to the eye of the patient for, for example, at least three, five, or fourteen consecutive days. One benefit of the dosing protocol is that it minimizes eye redness experienced by the patient during the patient's waking hours, while achieving a reduction in intraocular pressure that is desirable for treatment of glaucoma and ocular hypertension. In certain embodiments, the once daily dosage contains phentolamine mesylate.

Another aspect of the invention provides a method of treating a condition selected from the group consisting of glaucoma, ocular hypertension, and non-arteritic anterior ischemic optic neuropathy in a patient according to a monotherapy treatment regimen. The method comprises administering to an eye of a patient in need thereof a dosage of a single therapeutic agent in an amount effective for treatment of said condition, wherein the single therapeutic agent is phentolamine or a pharmaceutically acceptable salt thereof. The daily dosage may be administered to the eye of the patient according to a particular dosing protocol, such as administration to the eye of the patient once per day, which may be, for example, at or near the bed time of the patient. Such dosing protocol may entail for, for example, administering the dosage to the eye of the patient for at least three, five, or fourteen consecutive days. In certain embodiments, the single therapeutic agent is phentolamine mesylate.

Another aspect of the invention provides a method of treating a condition selected from the group consisting of glaucoma, ocular hypertension, and non-arteritic anterior ischemic optic neuropathy in a patient. The method comprises administering to an eye of a patient in need thereof a dosage of an alpha-adrenergic antagonist in an amount sufficient to achieve a reduction in a symptom or feature of the condition for a duration of at least 8 hours, to thereby treat the condition without at least one of the following adverse events:
  (a) stinging or burning sensation experienced by the patient upon administration of the alpha-adrenergic antagonist to the eye; or
  (b) an increase in eye redness more than two grades measured using the CCLRU Redness Grading Scale compared to the patient's level of eye redness without receiving the amount of alpha-adrenergic antagonist.
In certain embodiments, the symptom or feature of the condition is intraocular pressure. In certain embodiments, the method achieves a reduction in intraocular pressure in the eye of at least 5%, 10%, or 20% for a duration of at least 12, 18, or 24 hours.

Another aspect of the invention provides a pharmaceutical composition comprising an alpha-adrenergic antagonist and a second therapeutic agent selected from the group consisting of prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor. Preferably, the pharmaceutical composition is formulated for ophthalmic administration.

Another aspect of the invention provides a method of treating keratoconus in a patient, wherein the method comprises administering to an eye of a patient in need thereof a therapeutically effective dosage of an alpha-adrenergic antagonist to treat the keratoconus.

BRIEF DESCRIPTION OF FIGURES

FIG. 1 depicts exemplary eye redness as measured according to (1) the CCLRU Redness Grading Scale, and (2) the NYX-001 Redness Grading Scale.

DETAILED DESCRIPTION OF THE INVENTION

The invention provides methods, compositions, and kits containing an alpha-adrenergic antagonist, such as phentolamine, for treating patients suffering from glaucoma, ocular hypertension, and/or other ocular disorders. The alpha-adrenergic antagonist, such as phentolamine, is administered topically to the eye of the patient, preferably in the form of a liquid aqueous ophthalmic formulation. Desirably the alpha-adrenergic antagonist is administered to the patient once daily in order to reduce intraocular pressure in the eye of the patient, such as to achieve a reduction in intraocular pressure of at least 10%, 20% or more. Such reduction in intraocular pressure due to the alpha-adrenergic antagonist provides therapeutic benefits to patients suffering from glaucoma, ocular hypertension, and/or other ocular disorders. One benefit of therapeutic methods described herein is that the patient may also experience an improvement in visual performance. Such improvement in the patient's ability to see clearly, as well as ability to distinguish between an object and its background, is a benefit in addition to the therapeutic benefits provided for treating glaucoma, ocular hypertension, and/or other ocular disorders. Various aspects of the invention are set forth below in sections; however, aspects of the invention described in one particular section are not to be limited to any particular section.

Definitions

To facilitate an understanding of the present invention, a number of terms and phrases are defined below.

The terms "a," "an" and "the" as used herein mean "one or more" and include the plural unless the context is inappropriate.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. Unless specified otherwise, an effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for therapeutic use in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see Martin in Remington's Pharmaceutical Sciences, 15th Ed., Mack Publ. Co., Easton, PA [1975].

As used herein, the term "pharmaceutically acceptable salt" refers to any pharmaceutically acceptable salt (e.g., acid or base) of a compound of the present invention which, upon administration to a subject, is capable of providing a compound of this invention. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_3$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate (mesylate), 2-naphthalenesulfonate, nicotinate, oxalate, palmoate, pectinate, persulfate, phenylpropionate, picrate, pivalate, propionate, succinate, sulfate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "alkanoate" is art-recognized and refers to alkyl-$C(O)O^-$.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

Throughout the description, where compositions and kits are described as having, including, or comprising specific components, or where processes and methods are described as having, including, or comprising specific steps, it is contemplated that, additionally, there are compositions and kits of the present invention that consist essentially of, or consist of, the recited components, and that there are processes and methods according to the present invention that consist essentially of, or consist of, the recited processing steps.

As a general matter, compositions specifying a percentage are by weight unless otherwise specified. Further, if a variable is not accompanied by a definition, then the previous definition of the variable controls.

I. Therapeutic Methods

The invention provides methods for treating patients suffering from glaucoma, ocular hypertension, and/or other ocular disorders by administering to the eye of the patient an alpha-adrenergic antagonist, such as phentolamine. The alpha-adrenergic antagonist is administered topically to the eye of the patient, preferably in the form of a liquid aqueous ophthalmic formulation. Various aspects and embodiments of the therapeutic methods are described in the sections below. The sections are arranged for convenience and information in one section is not to be limited to that section, but may be applied to methods in other sections.

A. First Method

One aspect of the invention provides a method of treating a condition selected from the group consisting of glaucoma, ocular hypertension, and non-arteritic anterior ischemic optic neuropathy in a patient while minimizing eye redness during the patient's waking hours, wherein the method comprises administering to an eye of a patient in need thereof at or near the bedtime of the patient an effective amount of a once daily dosage of phentolamine or a pharmaceutically acceptable salt thereof to thereby treat the condition.

The method may be further characterized by additional features, such as the dosing regimen and the identity of the phentolamine or pharmaceutically acceptable salt thereof. The invention embraces all permutations and combinations of these features.

Accordingly, the method may be further characterized according to the dosing regimen. For example, in certain embodiments, the dosage is administered for at least three consecutive days. In certain embodiments, the dosage is administered for at least seven consecutive days. In certain embodiments, the dosage is administered for at least 14 consecutive days. In certain embodiments, the dosage is administered on at least three days in a five day period. In certain embodiments, the dosage is administered on at least three days in a seven day period. In certain embodiments, the dosage is administered on one day in a three day period. In certain embodiments, the dosage is administered on one day in a five day period.

The method may be further characterized according to the identity of the dosage. For example, in certain embodiments, the dosage comprises a pharmaceutically acceptable salt of phentolamine. In certain embodiments, the dosage comprises phentolamine mesylate.

B. Second Method

Another aspect of the invention provides a method of treating a condition selected from the group consisting of glaucoma, ocular hypertension, and non-arteritic anterior ischemic optic neuropathy in a patient according to a monotherapy treatment regimen, wherein the method comprises administering to an eye of a patient in need thereof a dosage of a single therapeutic agent in an amount effective for treatment of said condition, wherein the single therapeutic agent is phentolamine or a pharmaceutically acceptable salt thereof.

The method may be further characterized by additional features, such as the dosing regimen and the identity of the single therapeutic agent. The invention embraces all permutations and combinations of these features.

Accordingly, the method may be further characterized according to the dosing regimen. For example, in certain embodiments, the dosage is administered to the eye of the patient at or near the bedtime of the patient. In certain embodiments, the dosage is administered at least once daily for at least three consecutive days. In certain embodiments, the dosage is administered at least once daily for at least seven consecutive days. In certain embodiments, the dosage is administered at least once daily for at least 14 consecutive days. In certain embodiments, the dosage is administered on at least three days in a five day period. In certain embodiments, the dosage is administered on at least three days in a seven day period. In certain embodiments, the dosage is administered on one day in a three day period. In certain embodiments, the dosage is administered on one day in a five day period.

In certain embodiments, the dosage is administered once per day. In certain other embodiments, the dosage is administered twice, three times, or four times per day.

The method may be further characterized according to the identity of the single therapeutic agent. For example, in certain embodiments, the single therapeutic agent is a pharmaceutically acceptable salt of phentolamine. In certain embodiments, the single therapeutic agent is phentolamine mesylate.

C. Third Method

Another aspect of the invention provides a method of treating a condition selected from the group consisting of glaucoma, ocular hypertension, and non-arteritic anterior ischemic optic neuropathy in a patient, wherein the method comprises administering to an eye of a patient in need thereof a dosage of an alpha-adrenergic antagonist in an amount sufficient to achieve a reduction in a symptom or feature of the condition for a duration of at least 8 hours, to thereby treat the condition without at least one of the following adverse events:
  (a) stinging or burning sensation experienced by the patient upon administration of the alpha-adrenergic antagonist to the eye; or
  (b) an increase in eye redness more than two grades measured using the CCLRU Redness Grading Scale compared to the patient's level of eye redness without receiving the amount of alpha-adrenergic antagonist.

In certain embodiments, the stinging or burning sensation is a stinging or burning sensation that lasts for a duration of at least 0.1, 0.5, 1, 2, 3, 4, 5, 6, 7, 8, 9, 10, 12, 15, 20, or 30 minutes. In certain embodiments, the stinging or burning sensation is a stinging or burning sensation that lasts for a duration of at least 1 minute.

In certain embodiments, the symptom or feature of the condition is intraocular pressure. In certain embodiments, the method achieves a reduction in intraocular pressure in the eye of at least 5%, 10%, or 20% for a duration of at least 12, 18, or 24 hours.

Desirably, the alpha-adrenergic antagonist causes a reduction in intraocular pressure.

In an alternative embodiment, the invention provides a method of treating a condition selected from the group consisting of glaucoma, ocular hypertension, and non-arteritic anterior ischemic optic neuropathy in a patient, wherein the method comprises administering to an eye of a patient in need thereof a dosage of an alpha-adrenergic antagonist in an amount sufficient to achieve a reduction in a symptom or feature of the condition for a duration of at least 8 hours, to thereby treat the condition without at least one of the following adverse events:
  (a) stinging or burning sensation experienced by the patient at a time that is greater than two minute after administration of the alpha-adrenergic antagonist to the eye; or
  (b) an increase in eye redness more than two grades measured using the CCLRU Redness Grading Scale compared to the patient's level of eye redness without receiving the amount of alpha-adrenergic antagonist.

In certain embodiments, there is no stinging or burning sensation experienced by the patient at a time that is greater than 3, 4, 5, 6, 7, 8, 9, 10, 15, or 20 minutes after administration of the alpha-adrenergic antagonist to the eye.

The method may be further characterized by additional features, such as the dosing regimen and the identity of the alpha-adrenergic antagonist. The invention embraces all permutations and combinations of these features.

Accordingly, the method may be further characterized according to the dosing regimen for the alpha-adrenergic antagonist. For example, in certain embodiments, the alpha-adrenergic antagonist is administered to the eye of the patient at or near the bedtime of the patient. In certain embodiments, the alpha-adrenergic antagonist is administered to the eye of the patient within 1 hour of the patient's bedtime. In certain embodiments, the alpha-adrenergic antagonist is administered at least once daily for at least three consecutive days. In certain embodiments, the alpha-adrenergic antagonist is administered at least once daily for at least seven consecutive days. In certain embodiments, the alpha-adrenergic antagonist is administered at least once daily for at least 14 consecutive days. In certain embodiments, the dosage is administered once per day. In certain embodiments, the dosage is administered on at least three days in a five day period. In certain embodiments, the dosage is administered on at least three days in a seven day period. In certain embodiments, the dosage is administered on one day in a three day period. In certain embodiments, the dosage is administered on one day in a five day period.

In certain other embodiments, the dosage is administered twice, three times, or four times per day.

The method may be further characterized according to the dosage of alpha-adrenergic antagonist. For example, in certain embodiments, the dosage of alpha-adrenergic antagonist is an amount sufficient to achieve a reduction in a symptom or feature of the condition for a duration of at least 12 hours, to thereby treat the condition without any of the following adverse events: (a) stinging or burning sensation experienced by the patient upon administration of the alpha-adrenergic antagonist to the eye; and (b) an increase in eye redness more than two grades measured using the CCLRU Redness Grading Scale compared to the patient's level of eye redness without receiving the amount of alpha-adrenergic antagonist. In certain other embodiments, the dosage of alpha-adrenergic antagonist is an amount sufficient to achieve a reduction in a symptom or feature of the condition for a duration of at least 24 hours, to thereby treat the condition without any of the following adverse events: (a) stinging or burning sensation experienced by the patient upon administration of the alpha-adrenergic antagonist to the eye; and (b) an increase in eye redness more than two grades measured using the CCLRU Redness Grading Scale compared to the patient's level of eye redness without receiving the amount of alpha-adrenergic antagonist.

The method may be further characterized according to the identity of the alpha-adrenergic antagonist. For example, in certain embodiments, the alpha-adrenergic antagonist is phentolamine, phenoxybenzamine, tolazoline, trazodone, alfuzosin, doxazosin, prazosin, tamsulosin, terazosin, silodosin, atipamezole, idazoxan, mirtazapine, yohimbine, fenoldopam, thymoxamine, or a pharmaceutically acceptable salt of any of the foregoing. In certain embodiments, the alpha-adrenergic antagonist is phentolamine or a pharmaceutically acceptable salt thereof. In certain embodiments, the alpha-adrenergic antagonist is a pharmaceutically acceptable salt of phentolamine. In certain embodiments, the alpha-adrenergic antagonist is phentolamine mesylate. In certain embodiments, the alpha-adrenergic antagonist is fenoldopam mesylate.

In certain embodiments, the alpha-adrenergic antagonist is a non-selective alpha-adrenergic antagonist. In certain embodiments, the alpha-adrenergic antagonist is a reversible, non-selective alpha-adrenergic antagonist.

In certain embodiments, the alpha-adrenergic antagonist is characterized according to its activity towards certain alpha-adrenergic receptors. Accordingly, in certain embodiments, the alpha-adrenergic antagonist has antagonist activity towards an alpha-1 adrenergic receptor. Activity toward the alpha-1 adrenergic receptor may be further characterized according to whether there is activity toward one or more of the alpha-1 adrenergic receptor subtypes (e.g., alpha-1A, alpha-1B, and alpha-1D). Accordingly, in certain embodiments, the alpha-adrenergic antagonist has antagonist activity towards the alpha-IA adrenergic receptor. In certain embodiments, the alpha-adrenergic antagonist has antagonist activity towards the alpha-1B adrenergic receptor. In certain embodiments, the alpha-adrenergic antagonist has antagonist activity towards the alpha-1D adrenergic receptor. In certain embodiments, the alpha-adrenergic antagonist has antagonist activity towards each of the alpha-1 adrenergic receptor subtypes.

In certain embodiments, the alpha-adrenergic antagonist has antagonist activity towards an alpha-2 adrenergic receptor. Activity toward the alpha-2 adrenergic receptor may be further characterized according to whether there is activity toward one or more of the alpha-2 adrenergic receptor subtypes (e.g., alpha-2A, alpha-2B, and alpha-2C). Accordingly, in certain embodiments, the alpha-adrenergic antagonist has antagonist activity towards the alpha-2A adrenergic receptor. In certain embodiments, the alpha-adrenergic antagonist has antagonist activity towards the alpha-2B adrenergic receptor. In certain embodiments, the alpha-adrenergic antagonist has antagonist activity towards the alpha-2C adrenergic receptor. In certain embodiments, the alpha-adrenergic antagonist has antagonist activity towards each of the alpha-2 adrenergic receptor subtypes.

The alpha-adrenergic antagonist may be characterized according to its activity towards (i) an alpha-1 adrenergic receptor versus (ii) an alpha-2 adrenergic receptor. In certain embodiments, the alpha-adrenergic antagonist has antagonist activity at both (i) an alpha-1 adrenergic receptor and (ii) an alpha-2 adrenergic receptor. In certain embodiments, the alpha-adrenergic antagonist has antagonist activity at (i) an alpha-1 adrenergic receptor but not (ii) an alpha-2 adrenergic receptor. In certain embodiments, the alpha-adrenergic antagonist has antagonist activity at (i) an alpha-2 adrenergic receptor but not (ii) an alpha-1 adrenergic receptor. In certain embodiments, the inhibitory activity (as, for example, measured by an $IC_{50}$ value) of the alpha-adrenergic antagonist is at least 10-fold greater towards (i) the alpha-1 adrenergic receptor compared to the (ii) alpha-2 adrenergic receptor. In certain embodiments, the inhibitory activity (as, for example, measured by an $IC_{50}$ value) of the alpha-adrenergic antagonist is at least 10-fold greater towards (i) the alpha-2 adrenergic receptor compared to (ii) the alpha-1 adrenergic receptor.

D. Fourth Method

Another aspect of the invention provides a method of treating a condition selected from the group consisting of glaucoma, ocular hypertension, and non-arteritic anterior ischemic optic neuropathy in a patient, wherein the method comprises administering to an eye of a patient in need thereof a therapeutically effective dosage of an alpha-adrenergic antagonist and a second therapeutic agent selected from the group consisting of prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor, to thereby treat the condition.

The method may be further characterized by additional features, such as the dosing regimen and the identity of the alpha-adrenergic antagonist, and the identity of the second therapeutic agent. The invention embraces all permutations and combinations of these features.

Accordingly, the method may be further characterized according to the dosing regimen for the alpha-adrenergic antagonist. For example, in certain embodiments, the alpha-adrenergic antagonist is administered once per day. In certain embodiments, the alpha-adrenergic antagonist is administered two times, three times, or four times per day.

The method may be further characterized according to the identity of the second therapeutic agent. For example, in certain embodiments, the second therapeutic agent is selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, or a pharmaceutically acceptable salt of any one of the foregoing. In certain embodiments, the second therapeutic agent is selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, carbachol, aceclidine, oxotremorine, or a pharmaceutically acceptable salt of any one of the foregoing. In certain embodiments, the second therapeutic agent is selected from the group consisting of latanoprost, timolol, netarsudil, or a pharmaceutically acceptable salt of any one of the foregoing. In certain embodiments, the second therapeutic agent is betaxolol, apraclonidine, brinzolamide, unoprostone, levobunolol, carteolol, metipranolol, carbachol, ecothiophate iodide, omidenepag isopropyl (an EP2 agonist), sepetaprost, NO-bimatoprost, H-1337 (a leucine-rich repeat kinase inhibitor), or a pharmaceutically acceptable salt of any one of the foregoing. In certain embodiments, the second therapeutic agent is latanoprost. In certain embodiments, the second therapeutic agent is latanoprost administered at a daily dose of about 1.5 micrograms.

The method may be further characterized according to the identity of the alpha-adrenergic antagonist. For example, in certain embodiments, the alpha-adrenergic antagonist is phentolamine, phenoxybenzamine, tolazoline, trazodone, alfuzosin, doxazosin, prazosin, tamsulosin, terazosin, silodosin, atipamezole, idazoxan, mirtazapine, yohimbine, fenoldopam, thymoxamine, or a pharmaceutically acceptable salt of any of the foregoing. In certain embodiments, the alpha-adrenergic antagonist is phentolamine or a pharmaceutically acceptable salt thereof. In certain embodiments, the alpha-adrenergic antagonist is a pharmaceutically acceptable salt of phentolamine. In certain embodiments, the alpha-adrenergic antagonist is phentolamine mesylate.

E. Fifth Method

Another aspect of the invention provides a method of treating keratoconus in a patient, wherein the method comprises administering to an eye of a patient in need thereof a therapeutically effective dosage of an alpha-adrenergic antagonist to treat the keratoconus.

The method may be further characterized by additional features, such as the dosing regimen and the identity of the alpha-adrenergic antagonist, and the identity of any second therapeutic agent. The invention embraces all permutations and combinations of these features.

Accordingly, the method may be further characterized according to the dosing regimen for the alpha-adrenergic antagonist. For example, in certain embodiments, the alpha-adrenergic antagonist is administered once per day. In certain embodiments, the alpha-adrenergic antagonist is administered two times, three times, or four times per day.

In certain embodiments, the dosage is administered to the eye of the patient at or near the bedtime of the patient. In certain embodiments, the dosage is administered to the eye of the patient within 1 hour of the patient's bedtime.

In certain embodiments, the alpha-adrenergic antagonist is a pharmaceutically acceptable salt of phentolamine. In certain embodiments, the alpha-adrenergic antagonist is phentolamine mesylate.

F. Additional Methods

Additional therapeutic methods are provided below. The methods may be further characterized by additional features, such as the dosing regimen and the identity of the alpha-adrenergic antagonist.

One aspect of the invention provides a method of improving visual performance in a patient suffering from a disorder selected from the group consisting of glaucoma, elevated intraocular pressure, and a combination thereof, wherein the method comprises administering to an eye of a patient in need thereof a therapeutically effective dosage of an alpha-adrenergic antagonist to thereby improve visual performance and treat the disorder. In certain embodiments, the disorder is glaucoma.

Another aspect of the invention provides a method of improving visual performance and reducing intraocular pressure in a patient suffering from a disorder selected from the group consisting of glaucoma, elevated intraocular pressure, and a combination thereof, wherein the method comprises administering to an eye of a patient in need thereof a therapeutically effective dosage of an alpha-adrenergic antagonist to thereby improve visual performance, reduce intraocular pressure, and treat the disorder. In certain embodiments, the disorder is glaucoma.

Another aspect of the invention provides a method of improving visual performance in a patient suffering from keratoconus, wherein the method comprises administering to an eye of a patient in need thereof an effective amount of an alpha-adrenergic antagonist to thereby improve visual performance. In certain embodiments, the alpha-adrenergic antagonist is a pharmaceutically acceptable salt of phentolamine. In certain embodiments, the alpha-adrenergic antagonist is phentolamine mesylate.

Another aspect of the invention provides a method of improving visual performance and reducing pupil diameter in a patient suffering from a disorder selected from the group consisting of glaucoma, elevated intraocular pressure, and a combination thereof, wherein the method comprises administering to an eye of a patient in need thereof a therapeutically effective dosage of an alpha-adrenergic antagonist to thereby improve visual performance, reduce pupil diameter, and treat the disorder. In certain embodiments, the disorder is glaucoma.

Another aspect of the invention provides a method of reducing intraocular pressure and reducing pupil diameter in a patient suffering from a disorder selected from the group consisting of glaucoma, elevated intraocular pressure, and a combination thereof, wherein the method comprises administering to an eye of a patient in need thereof a therapeutically effective dosage of an alpha-adrenergic antagonist to thereby reduce intraocular pressure, reduce pupil diameter, and treat the disorder. In certain embodiments, the disorder is glaucoma.

Another aspect of the invention provides a method of treating glaucoma and achieving one or more of improving visual performance, reducing intraocular pressure, and reducing pupil diameter in a patient suffering from glaucoma, wherein the method comprises administering to an eye of a patient in need thereof a therapeutically effective dosage of an alpha-adrenergic antagonist to thereby treat the glaucoma and achieve one or more of improving visual performance, reducing intraocular pressure, and reducing pupil diameter in the patient.

Another aspect of the invention provides a method of treating glaucoma and elevated intraocular pressure and optionally improving visual performance in a patient, wherein the method comprises administering to an eye of a patient in need thereof a therapeutically effective dosage of an alpha-adrenergic antagonist to thereby treat the glaucoma and elevated intraocular pressure and optionally improve visual performance in the patient. In certain embodiments, the method improves visual performance.

The methods may be further characterized according to, for example, the improvement in visual performance. In certain embodiments, the improvement in visual performance is near-distance improvement in visual performance. In certain embodiments, the improvement in visual performance is improvement in visual performance at a distance. In certain embodiments, the improvement in visual performance is an improvement in visual acuity. In certain embodiments, the improvement in visual performance is an improvement in contrast sensitivity.

The methods may be further characterized according to, for example, characteristics of the patient. In certain embodiments, the patient has poor visual performance at a near distance. In certain embodiments, the patient has poor visual performance at a far distance.

G. Additional Optional Features of First, Third, and Fifth Therapeutic Methods

Additional optional features of the first, third, and fifth therapeutic methods include administering a second therapeutic agent. Accordingly, in certain embodiments, the method further comprises administering to the eye of the patient a second therapeutic agent selected from the group consisting of a prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor. In certain other embodiments, the method further comprises administering to the eye of the patient a second therapeutic agent selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, or a pharmaceutically acceptable salt of any one of the foregoing. In certain other embodiments, the method further comprises administering to the eye of the patient a second therapeutic agent selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, carbachol, aceclidine, oxotremorine, or a pharmaceutically acceptable salt of any one of the foregoing. In certain other embodiments, the method further administering to the eye of the patient a second therapeutic agent selected from the group consisting of betaxolol, apraclonidine, brinzolamide, unoprostone, levobunolol, carteolol, metipranolol, carbachol, ecothiophate iodide, omidenepag isopropyl, sepetaprost, NO-bimatoprost, and H-1337, or a pharmaceutically acceptable salt of any one of the foregoing. In certain embodiments, the second therapeutic agent is latanoprost. In certain embodiments, the second therapeutic agent is latanoprost administered at a daily dose of about 1.5 micrograms.

In certain embodiments, the method further comprises administering to the eye of the patient an additional therapeutic agent, such as an alpha-adrenergic antagonist. Accordingly, in certain embodiments, the method further comprises administering to the eye of the patient an additional therapeutic agent that is an alpha-adrenergic antagonist. In certain embodiments, the additional therapeutic agent is bunazosin or a pharmaceutically acceptable salt thereof. Bunazosin is a compound featuring greater inhibitory activity towards (i) the alpha-1 adrenergic receptor compared to the (ii) alpha-2 adrenergic receptor.

H. General Considerations for Therapeutic Methods

General considerations that may be applied to therapeutic methods described herein (e.g., the methods described in Parts A-G above) are provided below and include, for example, the degree of eye redness, the amount of phentolamine or pharmaceutically acceptable salt thereof in the dosage, the reduction in intraocular pressure in the eye due to the administering, the duration of reduction in intraocular pressure, the condition being treated, and patient populations that may derive particular benefits from the therapeutic methods. A more thorough description of such features is provided below. The invention embraces all permutations and combinations of these features.

Degree of Eye Redness

The methods may be further characterized according to the degree of eye redness the patient experiences. The degree of eye redness can be evaluated and characterized using procedures described in the literature, such as the Cornea and Contact Lens Research Unit (CCLRU) Redness Grading Scale developed by the School of Optometry, University of New South Wales. See, for example, Terry et al. in *Optom. Vis. Sci.* (1993) vol. 70, pages 234-243; and Pult et al. in *Ophthal. Physiol. Opt.* (2008) vol. 28, pages 13-20. The CCLRU Redness Grading Scale evaluates eye redness on a four-point scale: (0) no eye redness, (1) very slight eye redness, (2) slight eye redness, (3) moderate eye redness, and (4) severe eye redness. See FIG. 1 for an illustration of the eye redness scale.

In certain embodiments, the patient experiences an increase in eye redness of no more than two grades measured using the CCLRU Redness Grading Scale during the patient's waking hours compared to the patient's level of eye redness without receiving said dosage. In certain embodiments, the patient experiences an increase in eye redness of no more than one grade measured using the CCLRU Redness Grading Scale during the patient's waking hours compared to the patient's level of eye redness without receiving said dosage. In certain embodiments, any increase in eye redness experienced by the patient is less than one grade measured using the CCLRU Redness Grading Scale during the patient's waking hours compared to the patient's level of eye redness without receiving said dosage.

Dosage of Phentolamine or Pharmaceutically Acceptable Salt Thereof

The methods may be further characterized according to the amount of phentolamine or pharmaceutically acceptable salt thereof in the dosage. For example, in certain embodiments, the dosage contains from about 0.1 mg to about 2.0 mg of phentolamine or a pharmaceutically acceptable salt thereof. In certain embodiments, the dosage contains from about 0.5 mg to about 1.0 mg of phentolamine or a pharmaceutically acceptable salt thereof. In certain other embodiments, the dosage contains from about 0.1 mg to about 2.0 mg of phentolamine mesylate. In certain embodiments, the dosage contains from about 0.3 mg to about 0.7 mg of phentolamine mesylate. In certain embodiments, the dosage contains about 0.5 mg of phentolamine mesylate. In certain other embodiments, the dosage contains from about 0.8 mg to about 1.2 mg of phentolamine mesylate. In certain embodiments, the dosage contains about 1 mg of phentolamine mesylate.

The dosage of phentolamine or a pharmaceutically acceptable salt thereof is desirably administered to the eye of the patient in the form of an ophthalmic solution, which is delivered to the eye in the form of eye drop. A standard eye drop typically contains from about 0.03 mL to about 0.05 mL of solution.

In certain embodiments, the dosage may be in the form of an aqueous ophthalmic solution. For example, in certain embodiments, the dosage is an aqueous ophthalmic solution free of a chelating agent containing:
 (a) about 0.1% (w/v) to about 2% (w/v) of phentolamine mesylate;
 (b) about 1% (w/v) to about 6% (w/v) of at least one polyol compound selected from the group consisting of mannitol, glycerol, and propylene glycol;
 (c) about 1 mM to about 6 mM of an alkali metal acetate; and
 (d) water;
  wherein the solution has a pH in the range of 4 to 6 and does not contain a chelating agent.

In certain embodiments, the dosage is an aqueous ophthalmic solution free of a chelating agent containing:
 (a) about 0.5% (w/v) to about 2% (w/v) of phentolamine mesylate;
 (b) about 1% (w/v) to about 6% (w/v) of at least one polyol compound selected from the group consisting of mannitol, glycerol, and propylene glycol;
 (c) about 1 mM to about 6 mM of an alkali metal acetate; and
 (d) water;
  wherein the solution has a pH in the range of 4.5 to 5.5 and does not contain a chelating agent.

In certain embodiments, the at least one polyol is mannitol. In certain embodiments, the solution contains 4% (w/v) mannitol. In certain embodiments, the alkali metal acetate is sodium acetate. In certain embodiments, the solution comprises 3 mM sodium acetate.

In certain embodiments, the dosage is an aqueous ophthalmic solution free of a chelating agent containing:
 (a) about 0.25% (w/v) to about 2% (w/v) of phentolamine mesylate;
 (b) about 3% (w/v) to about 5% (w/v) of mannitol;

(c) about 2 mM to about 4 mM of sodium acetate; and
(d) water;
  wherein the solution has a pH in the range of 4.5 to 5.2 and does not contain a chelating agent.

In certain embodiments, the dosage is an aqueous ophthalmic solution free of a chelating agent containing:
(a) about 0.5% (w/v) to about 2% (w/v) of phentolamine mesylate;
(b) about 3% (w/v) to about 5% (w/v) of mannitol;
(c) about 2 mM to about 4 mM of sodium acetate; and
(d) water;
  wherein the solution has a pH in the range of 4.6 to 5.2 and does not contain a chelating agent.

In certain embodiments, the dosage is an aqueous ophthalmic solution free of a chelating agent containing:
(a) about 0.5% (w/v) to about 1% (w/v) of phentolamine mesylate;
(b) about 4% mannitol;
(c) about 3 mM sodium acetate; and
(d) water;
  wherein the solution has a pH in the range of 4.6 to 5.2 and does not contain a chelating agent.

In certain embodiments, the dosage is an aqueous ophthalmic solution containing:
(a) about 0.25% (w/v) to about 2% (w/v) of phentolamine mesylate;
(b) about 3% (w/v) to about 5% (w/v) of mannitol;
(c) about 1 mM to about 6 mM of sodium acetate; and
(d) water;
  wherein the solution has a pH in the range of 4.5 to 5.2 and does not contain any additional component that is a chelating agent.

In certain embodiments, the dosage is an aqueous ophthalmic solution containing:
(a) about 1% (w/v) of phentolamine mesylate;
(b) about 3% (w/v) to about 5% (w/v) of mannitol;
(c) about 2 mM to about 4 mM of a buffer comprising sodium acetate; and
(d) water;
  wherein the solution has a pH in the range of 4.5 to 5.2 and does not contain any additional component that is a chelating agent.

In certain embodiments, the dosage is an aqueous ophthalmic solution containing:
(a) about 0.25% (w/v) to about 2% (w/v) of phentolamine mesylate;
(b) about 3% (w/v) to about 5% (w/v) of mannitol;
(c) about 2 mM to about 4 mM of sodium acetate; and
(d) water;
  wherein the solution has a pH in the range of 4.5 to 5.2 and does not contain any additional component that is a chelating agent.

In certain embodiments, the dosage is an aqueous ophthalmic solution containing:
(a) about 0.5% (w/v) to about 2% (w/v) of phentolamine mesylate;
(b) about 3% (w/v) to about 5% (w/v) of mannitol;
(c) about 2 mM to about 4 mM of a buffer comprising sodium acetate; and
(d) water;
  wherein the solution has a pH in the range of 4.6 to 5.2 and does not contain any additional component that is a chelating agent.

In certain embodiments, the dosage is an aqueous ophthalmic solution containing:
(a) about 0.5% (w/v) to about 1% (w/v) of phentolamine mesylate;
(b) about 4% mannitol;
(c) about 3 mM of a buffer comprising sodium acetate; and
(d) water;
  wherein the solution has a pH in the range of 4.6 to 5.2 and does not contain any additional component that is a chelating agent.

In certain embodiments, the dosage is an aqueous ophthalmic solution comprising: (a) about 1% (w/v) of phentolamine mesylate; (b) about 4% (w/v) mannitol; (c) about 3 mM of a buffer comprising sodium acetate; and (d) water; wherein the solution has a pH in the range of 4.5 to 5.5 and does not contain any additional component that is a chelating agent.

In certain embodiments, the dosage is an aqueous ophthalmic solution free of a chelating agent comprising: (a) about 1% (w/v) of phentolamine mesylate; (b) about 4% (w/v) mannitol; (c) about 3 mM of a buffer comprising sodium acetate; and (d) water; wherein the solution has a pH in the range of 4.0 to 7.5 and does not contain a chelating agent.

Reduction in Intraocular Pressure in the Eye

The methods may be further characterized according to the reduction in intraocular pressure in the eye due to the administering. For example, in certain embodiments, the patient experiences at least a 5% reduction in intraocular pressure in the eye due to the administering. In certain embodiments, the patient experiences at least a 10% reduction in intraocular pressure in the eye due to the administering. In certain embodiments, the patient experiences at least a 15% reduction in intraocular pressure in the eye due to the administering. In certain embodiments, the patient experiences at least a 20% reduction in intraocular pressure in the eye due to the administering. In certain embodiments, the patient experiences at least a 25% reduction in intraocular pressure in the eye due to the administering. In certain embodiments, the patient experiences at least a 30% reduction in intraocular pressure in the eye due to the administering.

In certain embodiments, the patient experiences at least a 1 mmHg reduction in intraocular pressure in the eye due to the administering. In certain embodiments, the patient experiences at least a 2 mmHg reduction in intraocular pressure in the eye due to the administering. In certain embodiments, the patient experiences at least a 3 mmHg reduction in intraocular pressure in the eye due to the administering. In certain embodiments, the patient experiences at least a 4 mmHg reduction in intraocular pressure in the eye due to the administering. In certain embodiments, the patient experiences at least a 5 mmHg reduction in intraocular pressure in the eye due to the administering. In certain embodiments, the patient experiences at least a 6 mmHg reduction in intraocular pressure in the eye due to the administering. In certain embodiments, the patient experiences at least a 7 mmHg reduction in intraocular pressure in the eye due to the administering. In certain embodiments, the patient experiences at least an 8 mmHg reduction in intraocular pressure in the eye due to the administering.

In certain embodiments, the patient experiences reduction in intraocular pressure in the eye in the range of from about 1 mmHg to about 5 mmHg due to the administering. In certain embodiments, the patient experiences reduction in intraocular pressure in the eye in the range of from about 5 mmHg to about 10 mmHg due to the administering. In certain embodiments, the patient experiences reduction in intraocular pressure in the eye in the range of from about 10 mmHg to about 15 mmHg due to the administering. In certain embodiments, the patient experiences reduction in intraocular pressure in the eye in the range of from about 4 mmHg to about 8 mmHg due to the administering. In certain embodiments, the patient experiences reduction in intraocular pressure in the eye in the range of from about 8 mmHg to about 12 mmHg due to the administering.

Duration of Reduction in Intraocular Pressure

The methods may be further characterized according to the duration of reduction in intraocular pressure. For example, in certain embodiments, the reduction lasts for a duration of at least 12 hours. In certain embodiments, the reduction lasts for a duration of at least 24 hours. In certain embodiments, the reduction lasts for a duration of at least 2 days. In certain embodiments, the reduction lasts for a duration of at least 5 days. In certain embodiments, the reduction lasts for a duration of at least 7 days. In certain embodiments, the reduction lasts for a duration of at least 10, 14, 21, or 28 days.

In certain embodiments, the reduction lasts for a duration of from about 5 to about 24 hours. In certain embodiments, the reduction lasts for a duration of from about 12 to about 24 hours. In certain embodiments, the reduction lasts for a duration of from about 1 day to about 3 days. In certain embodiments, the reduction lasts for a duration of from about 3 days to about 5 days. In certain embodiments, the reduction lasts for a duration of from about 5 days to about 7 days. In certain embodiments, the reduction lasts for a duration of from about 7 days to about 14 days.

Condition Being Treated

The methods may be further characterized according to the condition being treated. For example, in certain embodiments, the condition is glaucoma. In certain other embodiments, the glaucoma is congenital glaucoma. In certain other embodiments, the glaucoma is open-angle glaucoma. In certain other embodiments, the glaucoma is closed-angle glaucoma. In certain other embodiments, the glaucoma is primary glaucoma. In certain other embodiments, the glaucoma is secondary glaucoma. In certain other embodiments, the glaucoma is pigmentary glaucoma, pseudoexfoliative glaucoma, traumatic glaucoma, neovascular glaucoma, uveitic glaucoma, or glaucoma due to irido corneal endothelial syndrome. In certain other embodiments, the glaucoma is normal tension glaucoma.

In certain embodiments, the condition is ocular hypertension. In certain embodiments, the condition is ocular hypertension after surgery.

In certain embodiments, the condition is keratoconus. In certain embodiments, the condition is non-arteritic anterior ischemic optic neuropathy.

Patient Populations that May Derive Particular Benefits from the Therapeutic Methods The methods may be further characterized according to patient populations that may derive particular benefits from the therapeutic methods. For example, in certain embodiments, the patient's eye has an intraocular pressure greater than about 22 mmHg. In certain other embodiments, the patient to begin treatment is characterized as having an intraocular pressure in the range of from about 20 mmHg to about 30 mmHg. In certain embodiments, the patient to begin treatment is characterized as having an intraocular pressure in the range of from about 20 mmHg to about 25 mmHg. In certain other embodiments, the patient to begin treatment is characterized as having an intraocular pressure in the range of from about 25 mmHg to about 30 mmHg.

In certain other embodiments, the patient's eye has an intraocular pressure not greater than than about 22 mmHg. In certain other embodiments, the patient to begin treatment is characterized as having an intraocular pressure in the range of from about 12 mmHg to about 22 mmHg. In certain other embodiments, the patient to begin treatment is characterized as having an intraocular pressure in the range of from about 15 mmHg to about 22 mmHg. In certain other embodiments, the patient to begin treatment is characterized as having an intraocular pressure in the range of from about 18 mmHg to about 22 mmHg. In certain other embodiments, the patient to begin treatment is characterized as having an intraocular pressure in the range of from about 10 mmHg to about 12 mmHg, from about 12 mmHg to about 14 mmHg, from about 14 mmHg to about 16 mmHg, from about 16 mmHg to about 18 mmHg, from about 18 mmHg to about 20 mmHg, or from about 20 mmHg to about 22 mmHg. In certain other embodiments, the patient to begin treatment is characterized as having an intraocular pressure less than about 15, 17, 19, 21 or 22 mmHg.

In certain other embodiments, the patient to begin treatment is characterized as having an intraocular pressure less than 26 mmHg. In certain other embodiments, the patient to begin treatment is characterized as having an intraocular pressure less than 24 mmHg. In certain other embodiments, the patient to begin treatment is characterized as having an intraocular pressure less than 22 mmHg. In certain other embodiments, the patient to begin treatment is characterized as having an intraocular pressure less than 20 mmHg. In certain other embodiments, the patient to begin treatment is characterized as having an intraocular pressure less than 18 mmHg. In certain other embodiments, the patient to begin treatment is characterized as having an intraocular pressure less than 16 mmHg.

In certain other embodiments, the patient to begin treatment is characterized as having an intraocular pressure in the range of from about 17 mmHg to about 36 mmHg, from about 17 mmHg to about 32 mmHg, from about 17 mmHg to about 28 mmHg, from about 17 mmHg to about 26 mmHg, from about 17 mmHg to about 24 mmHg, or from about 17 mmHg to about 22 mmHg. In certain other embodiments, the patient to begin treatment is characterized as having an intraocular pressure in the range of from about 20 mmHg to about 36 mmHg, from about 20 mmHg to about 32 mmHg, from about 20 mmHg to about 28 mmHg, from about 20 mmHg to about 26 mmHg, from about 20 mmHg to about 24 mmHg, or from about 20 mmHg to about 22 mmHg. In certain other embodiments, the patient to begin treatment is characterized as having an intraocular pressure in the range of from about 20 mmHg to about 26 mmHg, from about 20 mmHg to about 25 mmHg, from about 20 mmHg to about 24 mmHg, from about 20 mmHg to about 23 mmHg, or from about 20 mmHg to about 22 mmHg. In certain other embodiments, the patient to begin treatment is characterized as having an intraocular pressure less than about 23, 24, 25, or 26 mmHg In certain embodiments, the patient is a human. In certain embodiments, the patient is an adult human. In certain embodiments, the patient is a pediatric human.

Time of Administration

Various methods described above require administration of the dosage at or near the bedtime of the patient. Accordingly, in certain embodiments, the dosage is administered within 2 hours, 1.5 hours, 1 hour, 45 minutes, 30 minutes, or 15 minutes of the patient's bedtime. In certain embodiments, the dosage is administered within 1 hour of the patient's bedtime.

Improvement in Visual Performance

One benefit of the therapeutic methods is that the patient may also experience an improvement in visual performance.

Visual performance pertains to the patient's overall vision quality and includes a patient's ability to see clearly, as well as ability to distinguish between an object and its background.

One aspect of visual performance is visual acuity. Visual acuity is a measure of a patient's ability to see clearly. Visual acuity can be measured using, for example, a Snellen chart. Further, the visual acuity measurement can be taken under scotopic conditions, mesopic conditions, and/or photopic conditions.

Another aspect of visual performance is contrast sensitivity. Contrast sensitivity is a measure of the patient's ability to distinguish between an object and its background. Contrast sensitivity can be measured using, for example, a Holladay Automated Contrast Sensitivity System. The contrast sensitivity can be measured under various light conditions, including, for example, photopic conditions, mesopic conditions, and scotopic conditions, each either with or without glare. In certain embodiments, the contrast sensitivity is measured under mesopic conditions either with or without glare.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a two-line improvement in the patient's vision as measured using the Snellen chart. In certain other embodiments, the improvement in visual acuity is a one-line improvement in the patient's vision as measured using the Snellen chart.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions. Further, contrast sensitivity can be measured in the presence of glare or the absence of glare. All combinations of light conditions and glare are contemplated.

Benefits provided by the therapeutic methods can be characterized according to the patient's improvement in contrast sensitivity. For example, in certain embodiments, the improvement in contrast sensitivity is at least a 10% (or 20%, 30%, 50%, 60%, or 70%) improvement measured under mesopic conditions using the Holladay Automated Contrast Sensitivity System. In certain embodiments, the improvement in contrast sensitivity is at least a 10% (or 20%, 30%, 50%, 60%, or 70%) improvement measured under photopic conditions using the Holladay Automated Contrast Sensitivity System. In certain other embodiments, the improvement in contrast sensitivity is at least a 10% (or 20%, 30%, 50%, 60%, or 70%) improvement measured under mesopic conditions or scotopic conditions using the Holladay Automated Contrast Sensitivity System.

In certain other embodiments, the improvement in visual performance provided by the method is both (i) improved visual acuity (such as under scotopic conditions, mesopic conditions, and/or photopic conditions) and (ii) improved contrast sensitivity (such as under scotopic conditions, mesopic conditions, and/or photopic conditions).

In certain embodiments, the improvement in visual performance is improvement in near-vision performance. In certain embodiments, the improvement in visual performance is improvement in visual performance at a distance. In certain embodiments, the improvement in visual performance is improved visual performance under low-light conditions. In certain embodiments, the improvement in visual performance is improved visual acuity. In certain embodiments, the improvement in visual performance is improved contrast sensitivity. In certain embodiments, the method provides at least a 10% reduction in pupil diameter in the eye of the patient. In certain embodiments, the method provides at least a 15% reduction in pupil diameter in the eye of the patient. In certain embodiments, the method provides at least a 20% reduction in pupil diameter in the eye of the patient. In certain embodiments, the method provides at least a 25% reduction in pupil diameter in the eye of the patient. In certain embodiments, the method provides at least a 30% reduction in pupil diameter in the eye of the patient.

Reduction in Pupil Diameter

One benefit of the therapeutic methods is that the patient may also experience a reduction in pupil diameter. Reduction in pupil diameter can result in improvement in visual performance.

The reduction in pupil diameter can be characterized according to, for example, the percent reduction in pupil diameter and size of the pupil measured under certain light conditions. Accordingly, in certain embodiments, the reduction in pupil diameter under mesopic conditions is at least 5% compared to the pupil diameter of the patient under the same mesopic conditions but not having received the therapy defined by the method. In certain other embodiments, the reduction in pupil diameter under mesopic conditions is at least 10% compared to the pupil diameter of the patient under the same mesopic conditions but not having received the therapy defined by the method. In certain other embodiments, the patient experiences a reduction in pupil diameter of at least 0.5 mm when measured under mesopic conditions relative to the diameter of the patient's pupil under the same mesopic conditions but not having received the therapy defined by the method. In certain other embodiments, the patient experiences a reduction in pupil diameter ranging from about 0.6 mm to about 3 mm, about 0.6 mm to about 2.5 mm, or about 0.6 mm to about 2 mm when measured under mesopic conditions relative to the diameter of the patient's pupil under the same mesopic conditions but not having received the therapy defined by the method. In certain other embodiments, the patient experiences a reduction in pupil diameter ranging from about 0.6 mm to about 1.2 mm when measured under mesopic conditions relative to the diameter of the patient's pupil under the same mesopic conditions but not having received the therapy defined by the method. In yet other embodiments, the patient's pupil is reduced to a diameter of about 3 mm to about 5 mm, about 3 mm to about 6 mm, about 4 mm to about 5 mm, about 4 mm to about 6 mm, or about 4 mm to about 7 mm under mesopic conditions due to the therapy defined by the method. In certain embodiments, the patient's pupil is reduced to a diameter of about 4 mm to about 6 mm under mesopic conditions due to the therapy defined by the method.

In certain embodiments, the method provides at least a 10% reduction in pupil diameter in the eye of the patient. In certain embodiments, the method provides at least a 15% reduction in pupil diameter in the eye of the patient. In certain embodiments, the method provides at least a 20% reduction in pupil diameter in the eye of the patient. In certain embodiments, the method provides at least a 25% reduction in pupil diameter in the eye of the patient. In certain embodiments, the method provides at least a 30% reduction in pupil diameter in the eye of the patient.

Reducing Aberrant Focus of Scattered Light Rays in a Patient's Eye

One benefit of the therapeutic methods is that the patient may also experience a reduction in aberrant focus of scattered light rays in the patient's eye. This can provide improvement in visual performance for the patient. In certain embodiments, the therapeutic method provides a reduction in aberrant focus of scattered light rays in a patient's eye for at least twenty hours. In certain embodiments, the therapeutic method provides a reduction aberrant focus of scattered light rays in a patient's eye for at least twenty-four hours. In yet other embodiments, the therapeutic method provides a reduction aberrant focus of scattered light rays in a patient's eye for at least thirty-six hours, forty-eight hours, sixty hours, or seventy-two hours.

II. Combination Therapy

Another aspect of the invention provides for combination therapy. The First and Third Therapeutic Methods described hereinabove may optionally further comprise administering one or more second therapeutic agents to the patient. Exemplary second therapeutic agents include, for example:

A prostaglandin analog, such as latanoprost, bimatoprost, travoprost, tafluprost, latanoprostene bunod, or a pharmaceutically acceptable salt thereof;

A beta blocker, such as timolol or a pharmaceutically acceptable salt thereof;

An alpha agonist, such as brimonidine or a pharmaceutically acceptable salt thereof;

A carbonic anhydrase inhibitor, such as dorzolamide, brinzolamide, acetazolamide, methazolamide, or a pharmaceutically acceptable salt thereof;

A cholinergic agonist, such as pilocarpine or a pharmaceutically acceptable salt thereof;

A Rho kinase inhibitor, such as netarsudil or a pharmaceutically acceptable salt thereof.

Latanaoprost may be administered in the form of a sterile, isotonic, buffered aqueous solution of latanoprost with a pH of approximately 6.7 and an osmolality of approximately 267 mOsmol/kg, where each 1 mL of the solution contains 50 micrograms of latanoprost. The solution may optionally contain benzalkonium chloride (0.02% w/w), sodium chloride, sodium dihydrogen phosphate monohydrate, and disodium hydrogen phosphate.

Latanaoprost may be administered to the patient according to the procedures described in the XALATAN® prescribing information, which is hereby incorporated by reference. In certain embodiments, a single daily dose of 1.5 micrograms of latanoprost is administered to the patient's eye. In certain embodiments, a single daily dose in the range of about 0.5 to about 1.0 micrograms, about 1.0 to about 1.5 micrograms, or about 1.5 to about 2.0 micrograms of latanoprost is administered to the patient's eye.

Timolol may be administered as timolol maleate in the form of an ophthalmic solution. One or two drops per day of a solution that contains on a 1 mL basis 3.4 mg of timolol maleate may be administered to the eye of the patient. Alternatively, one drop per day of a solution that contains on a 1 mL basis 6.8 mg of timolol maleate may be administered to the eye of the patient.

Netarsudil may be administered to the patient in the form of an ophthalmic solution, such as a sterile, isotonic, buffered aqueous solution containing netarsudil dimesylate (0.02% w/w) having a pH of approximately 5 and an osmolality of approximately 295 mOsmol/kg. Each 1 mL of the solution contains 0.28 mg of netarsudil dimesylate. The aqueous solution may contain benzalkonium chloride (e.g., 0.015% w/w), boric acid, and mannitol. Netarsudil dimesylate may be administered to the patient once per day as one eye drop of the sterile, isotonic, buffered aqueous solution containing netarsudil dimesylate (0.02% w/w) having a pH of approximately 5 and an osmolality of approximately 295 mOsmol/kg.

The amount of each therapeutic agent and the relative timing of administration of each therapeutic agent may be selected in order to achieve a desired combined therapeutic effect. For example, when administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like In certain embodiments, the therapeutic agents may act additively or synergistically. A synergistic combination may allow the use of lower dosages of one or more agents and/or less frequent administration of one or more agents of a combination therapy. A lower dosage or less frequent administration of one or more agents may lower toxicity of the therapy without reducing the efficacy of the therapy.

Pharmaceutical Compositions Containing at Least Two Active Agents

Another aspect of the invention provides pharmaceutical compositions containing at least two active agents. For example, one aspect of the invention provides a pharmaceutical composition comprising an alpha-adrenergic antagonist and a second therapeutic agent selected from the group consisting of prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor.

The pharmaceutical composition may be further characterized according to the identity of the second therapeutic agent. For example, in certain embodiments, the second therapeutic agent is selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, or a pharmaceutically acceptable salt of any one of the foregoing. In certain embodiments, the second therapeutic agent is selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, carbachol, aceclidine, oxotremorine, or a pharmaceutically acceptable salt of any one of the foregoing. In certain embodiments, the second therapeutic agent is selected from the group consisting of latanoprost, timolol, netarsudil, or a pharmaceutically acceptable salt of any one of the foregoing. In certain embodiments, the second therapeutic agent selected is betaxolol, apraclonidine, brinzolamide, unoprostone, levobunolol, carteolol, metipranolol, carbachol, ecothiophate iodide, omidenepag isopropyl (an EP2 agonist), sepetaprost, NO-bimatoprost, H-1337 (a leucine-rich repeat kinase inhibitor), or a pharmaceutically acceptable salt of any one of the foregoing The pharmaceutical composition may be further characterized according to the identity of the alpha-adrenergic antagonist. For example, in certain embodiments, the alpha-adrenergic antagonist is phentolamine, phenoxybenzamine, tolazoline, trazodone, alfuzosin, doxazosin, prazosin, tamsulosin, terazosin, silodosin, atipamezole, idazoxan, mirtazapine, yohimbine, fenoldopam, thymoxamine, or a pharmaceutically acceptable salt of any of the foregoing. In certain embodiments, the alpha-adrenergic antagonist is phentolamine or a pharmaceutically acceptable salt thereof. In certain embodiments, the alpha-adrenergic antagonist is a pharmaceutically acceptable salt of phentolamine. In certain embodiments, the alpha-adrenergic antagonist is phentolamine mesylate.

In certain embodiments, the pharmaceutical composition comprises (i) pharmaceutically acceptable salt of phentolamine and (ii) latanoprost.

In certain embodiments, the pharmaceutical composition is formulated for ophthalmic administration.

In certain embodiments, the invention provides an aqueous ophthalmic solution comprising:
(a) about 0.1% (w/v) to about 2% (w/v) of phentolamine mesylate;
(b) latanoprost (e.g., about 0.005% (w/v) latanoprost);
(c) about 1% (w/v) to about 6% (w/v) of at least one polyol compound selected from the group consisting of mannitol, glycerol, and propylene glycol;
(d) about 1 mM to about 6 mM of an alkali metal acetate; and
(e) water;
wherein the solution has a pH in the range of 4 to 6 and does not contain any additional component that is a chelating agent.

In certain embodiments, the invention provides an aqueous ophthalmic solution comprising:
(a) about 0.1% (w/v) to about 2% (w/v) of phentolamine mesylate;
(b) latanoprost (e.g., about 0.005% (w/v) latanoprost);
(c) about 1% (w/v) to about 6% (w/v) of at least one polyol compound selected from the group consisting of mannitol, glycerol, and propylene glycol;
(d) about 1 mM to about 6 mM of an alkali metal acetate; and
(e) water;
wherein the solution has a pH in the range of 4 to 6 and does not contain any additional component that is a chelating agent.

In certain embodiments, the dosage is an aqueous ophthalmic solution comprising:
(a) about 0.5% (w/v) to about 2% (w/v) of phentolamine mesylate;
(b) latanoprost (e.g., about 0.005% (w/v) latanoprost);
(c) about 1% (w/v) to about 6% (w/v) of at least one polyol compound selected from the group consisting of mannitol, glycerol, and propylene glycol;
(d) about 1 mM to about 6 mM of an alkali metal acetate; and
(e) water;
wherein the solution has a pH in the range of 4.5 to 5.5 and does not contain any additional component that is a chelating agent.

In certain embodiments, the at least one polyol is mannitol. In certain embodiments, the solution contains 4% (w/v) mannitol. In certain embodiments, the alkali metal acetate is sodium acetate. In certain embodiments, the solution comprises 3 mM sodium acetate.

In certain embodiments, the dosage is an aqueous ophthalmic solution containing:
(a) about 0.25% (w/v) to about 2% (w/v) of phentolamine mesylate;
(b) latanoprost (e.g., about 0.005% (w/v) latanoprost);
(c) about 3% (w/v) to about 5% (w/v) of mannitol;
(d) about 1 mM to about 6 mM of sodium acetate; and
(e) water;
wherein the solution has a pH in the range of 4.5 to 5.2 and does not contain any additional component that is a chelating agent.

In certain embodiments, the dosage is an aqueous ophthalmic solution containing:
(a) about 1% (w/v) of phentolamine mesylate;
(b) latanoprost (e.g., about 0.005% (w/v) latanoprost);
(c) about 3% (w/v) to about 5% (w/v) of mannitol;
(d) about 2 mM to about 4 mM of a buffer comprising sodium acetate; and
(e) water;
wherein the solution has a pH in the range of 4.5 to 5.2 and does not contain any additional component that is a chelating agent.

In certain embodiments, the dosage is an aqueous ophthalmic solution containing:
(a) about 0.25% (w/v) to about 2% (w/v) of phentolamine mesylate;
(b) latanoprost (e.g., about 0.005% (w/v) latanoprost);
(c) about 3% (w/v) to about 5% (w/v) of mannitol;
(d) about 2 mM to about 4 mM of sodium acetate; and
(e) water;
wherein the solution has a pH in the range of 4.5 to 5.2 and does not contain any additional component that is a chelating agent.

In certain embodiments, the dosage is an aqueous ophthalmic solution containing:
(a) about 0.5% (w/v) to about 2% (w/v) of phentolamine mesylate;
(b) latanoprost (e.g., about 0.005% (w/v) latanoprost);
(c) about 3% (w/v) to about 5% (w/v) of mannitol;
(d) about 2 mM to about 4 mM of a buffer comprising sodium acetate; and
(e) water;
wherein the solution has a pH in the range of 4.6 to 5.2 and does not contain any additional component that is a chelating agent.

In certain embodiments, the dosage is an aqueous ophthalmic solution containing:
(a) about 0.5% (w/v) to about 1% (w/v) of phentolamine mesylate;
(b) latanoprost (e.g., about 0.005% (w/v) latanoprost);
(c) about 4% mannitol;
(d) about 3 mM of a buffer comprising sodium acetate; and
(e) water;
wherein the solution has a pH in the range of 4.6 to 5.2 and does not contain any additional component that is a chelating agent.

In certain embodiments, the dosage is an aqueous ophthalmic solution comprising: (a) about 1% (w/v) of phentolamine mesylate; (b) about 4% (w/v) mannitol; (c) about 3 mM of a buffer comprising sodium acetate; (d) water; and (e) latanoprost (e.g., about 0.005% (w/v) latanoprost);

wherein the solution has a pH in the range of 4.5 to 5.5 and does not contain any additional component that is a chelating agent.

In certain embodiments, the dosage is an aqueous ophthalmic solution free of a chelating agent comprising: (a) about 1% (w/v) of phentolamine mesylate; (b) about 4% (w/v) mannitol; (c) about 3 mM of a buffer comprising sodium acetate; (d) water; and (e) latanoprost (e.g., about 0.005% (w/v) latanoprost); wherein the solution has a pH in the range of 4.0 to 7.5 and does not contain a chelating agent.

Implantable Ocular Device

Compositions described herein may be administered to the patient's eye via an implantable ocular device that dispenses the composition. The implantable ocular device may be configured to dispense the composition at a desired rate and/or frequency. In certain embodiments, the implantable ocular device is a slow release insert.

III. Ophthalmic Solutions

Therapeutically active agents are desirably administered to the eye of the patient in the form of an ophthalmic solution. Such an ophthalmic solution comprises one or more therapeutically active agents and a pharmaceutically acceptable carrier. Desirably, the ophthalmic solution exhibits good storage stability to permit distribution of the ophthalmic solution through normal distribution channels for pharmaceuticals. In certain embodiments, the pharmaceutically acceptable carrier is water. Additional components may be added to the ophthalmic solution in order to optimize performance properties of the ophthalmic solution. Exemplary additional components include, for example, a chelating agent (e.g., EDTA), polyol compound, poly($C_{2-4}$alkylene)glycol polymer, dextran, cellulose agent, buffer, tonicity modifier, preservative, antioxidant, viscosity modifying agent, corneal permeation enhancing agent, solubilizing agent, stabilizing agent, surfactant, demulcent polymer, wetting agent, and other materials.

Ophthalmic solutions may be further characterized according to the presence or absence of one or more of a chelating agent (e.g., EDTA), polyol compound, poly($C_{2-4}$alkylene)glycol polymer, dextran, cellulose agent, buffer, tonicity modifier, preservative, antioxidant, viscosity modifying agent, corneal permeation enhancing agent, solubilizing agent, stabilizing agent, surfactant, demulcent polymer, wetting agent, and other materials. In certain embodiments, the ophthalmic solution does not contain a chelating agent (e.g., EDTA). In certain embodiments, the ophthalmic solution does not contain a preservative.

Various therapeutic methods above involve administering a dosage of phentolamine or a pharmaceutically acceptable salt thereof to the patient. The dosage of phentolamine or a pharmaceutically acceptable salt thereof is desirably in the form of an ophthalmic solution. The ophthalmic solution is formulated to be suitable for administration to the eye of a patient, and desirably provides immediate release of phentolamine, that is, the ophthalmic solution is not a sustained release formulation that delivers phentolamine over an extended duration, such as hours, days or weeks.

The ophthalmic solution desirably comprises an aqueous pharmaceutically acceptable carrier and phentolamine or a pharmaceutically acceptable salt thereof. The ophthalmic solution may contain excipients(s) that are suitable for administration to the eye. Various pharmaceutically acceptable salts are described in the literature. The preferred salt form of phentolamine is phentolamine mesylate. Accordingly, the methods may use an ophthalmic solution that comprises an aqueous pharmaceutically acceptable carrier and phentolamine mesylate.

Accordingly, in certain embodiments, the dosage utilized in the methods is an ophthalmic solution comprising an aqueous pharmaceutically acceptable carrier and phentolamine or a pharmaceutically acceptable salt thereof. In certain other embodiments, the dosage is an ophthalmic solution comprising an aqueous pharmaceutically acceptable carrier and phentolamine mesylate. In certain other embodiments, the dosage is an ophthalmic solution comprising water, a polyol, and phentolamine or a pharmaceutically acceptable salt thereof. In certain other embodiments, the dosage is an ophthalmic solution comprising water, mannitol, and phentolamine mesylate. In certain other embodiments, the dosage is an ophthalmic solution comprising water, a polyol, an alkali metal carboxylate, and phentolamine or a pharmaceutically acceptable salt thereof. In certain other embodiments, the dosage is an ophthalmic solution comprising water, mannitol, sodium acetate, and phentolamine mesylate.

Other ophthalmic solutions that are contemplated for use in the present invention include, for example, (i) aqueous ophthalmic solutions free of a chelating agent, and (ii) polyvinylpyrrolidone artificial tears formulations, each of which are described in more detail below.

Ophthalmic solutions may be further characterized according to the viscosity of the solution. In certain embodiments, the ophthalmic solution at a temperature of about 25° C. has a viscosity in the range of 0.9 cP to about 1.1 cP. In certain embodiments, the ophthalmic solution at a temperature of about 25° C. has a viscosity of about 1 cP.

Aqueous Ophthalmic Solution Free of a Chelating Agent

In certain embodiments, the dosage utilized in the methods is an aqueous ophthalmic solution free of a chelating agent, wherein said solution comprises (a) phentolamine or a pharmaceutically acceptable salt thereof; (b) at least one polyol compound, such as a polyol compound having a molecular weight less than 250 g/mol; (c) at least one buffer; and (d) water; wherein the solution does not contain a chelating agent. The amount of ingredients in the aqueous ophthalmic solutions may be selected in order to achieve particular performance properties, such as stability to storage, minimize irritation to the eye of a patient, and enhance penetration of phentolamine into the eye of a patient.

One exemplary preferred solution is an aqueous ophthalmic solution free of a chelating agent comprising: (a) about 0.10% (w/v) to about 4% (w/v) of phentolamine or a pharmaceutically acceptable salt thereof; (b) about 1% (w/v) to about 6% (w/v) of at least one polyol compound having a molecular weight less than 250 g/mol; (c) about 0.1 mM to about 10 mM of at least one buffer; and (d) water; wherein the solution has a pH in the range of 4.0 to 7.5 and does not contain a chelating agent.

Exemplary components and features of the aqueous ophthalmic solutions are described in more detail below.

Phentolamine & Pharmaceutically Acceptable Salts

The aqueous ophthalmic solution comprises phentolamine or a pharmaceutically acceptable salt of phentolamine. Exemplary pharmaceutically acceptable salts include, for example, the hydrochloric acid salt and mesylate salt. Accordingly, in certain embodiments, the solution comprises phentolamine (i.e., as the free base). In certain other embodiments, the solution comprises phentolamine hydrochloride. In certain yet other embodiments, the solution comprises phentolamine mesylate.

The amount of phentolamine or a pharmaceutically acceptable salt thereof in the aqueous ophthalmic solution may be adjusted in order to achieve desired performance properties. For example, where is it desired to provide a larger amount of phentolamine (or pharmaceutically acceptable salt thereof) to the patient in a single administration of the aqueous ophthalmic solution, the concentration of phentolamine (or pharmaceutically acceptable salt thereof) is increased in the aqueous ophthalmic solution. Single administration of aqueous ophthalmic solutions having a higher concentration of phentolamine (or pharmaceutically acceptable salt thereof) may provide the patient with reduced intraocular pressure for a longer duration of time because more phentolamine (or pharmaceutically acceptable salt thereof) is administered to the patient.

Accordingly, in certain embodiments, the aqueous ophthalmic solution comprises from about 0.1% (w/v) to about 5% (w/v) of phentolamine or a pharmaceutically acceptable salt thereof. In certain embodiments, the aqueous ophthalmic solution comprises from about 0.1% (w/v) to about 1% (w/v) of phentolamine or a pharmaceutically acceptable salt thereof, about 1% (w/v) to about 2% (w/v) of phentolamine or a pharmaceutically acceptable salt thereof, about 2% (w/v) to about 3% (w/v) of phentolamine or a pharmaceutically acceptable salt thereof, about 3% (w/v) to about 4% (w/v) of phentolamine or a pharmaceutically acceptable salt thereof, about 4% (w/v) to about 5% (w/v) of phentolamine or a pharmaceutically acceptable salt thereof. In certain embodiments, the aqueous ophthalmic solution comprises from about 0.1% (w/v) to about 2% (w/v) of phentolamine or a pharmaceutically acceptable salt thereof. In certain embodiments, the aqueous ophthalmic solution comprises from about 0.25% (w/v) to about 2% (w/v) of phentolamine or a pharmaceutically acceptable salt thereof. In certain other embodiments, the aqueous ophthalmic solution comprises from about 0.5% (w/v) to about 2% (w/v) of phentolamine or a pharmaceutically acceptable salt thereof. In certain other embodiments, the aqueous ophthalmic solution comprises from about 0.25% (w/v) to about 1% (w/v) of phentolamine or a pharmaceutically acceptable salt thereof. In certain other embodiments, the aqueous ophthalmic solution comprises about 1% (w/v) of phentolamine or a pharmaceutically acceptable salt thereof. In certain other embodiments, the aqueous ophthalmic solution comprises from about 0.1% (w/v) to about 4% (w/v) of phentolamine mesylate. In certain other embodiments, the aqueous ophthalmic solution comprises from about 0.1% (w/v) to about 2% (w/v) of phentolamine mesylate. In certain other embodiments, the aqueous ophthalmic solution comprises from about 0.25% (w/v) to about 2% (w/v) of phentolamine mesylate. In certain other embodiments, the aqueous ophthalmic solution comprises from about 0.5% (w/v) to about 2% (w/v) of phentolamine mesylate. In certain other embodiments, the aqueous ophthalmic solution comprises from about 0.25% (w/v) to about 1% (w/v) of phentolamine mesylate. In certain other embodiments, the aqueous ophthalmic solution comprises about 1% (w/v) of phentolamine mesylate. In certain other embodiments, the aqueous ophthalmic solution comprises about 0.25% (w/v) or about 0.5% (w/v) of phentolamine mesylate.

Polyol Compounds

The aqueous ophthalmic solution comprises one or more polyol compounds. The polyol compound is an organic compound having at least two hydroxyl groups (e.g., from 2 to about 6 hydroxyl groups). The polyol compound is beneficial to the aqueous ophthalmic solution because, for example, it can increase the stability of the aqueous ophthalmic solution to storage and/or modify the tonicity of the aqueous ophthalmic solution. Exemplary polyol compounds include, for example, mannitol, glycerol, propylene glycol, ethylene glycol, sorbitol, and xylitol.

The aqueous ophthalmic solution may contain a single polyol compound or a mixture of one or more polyol compounds. In other words, the aqueous ophthalmic solution comprises at least one polyol compound. In certain embodiments, the aqueous ophthalmic solution comprises at least one polyol compound that is mannitol, glycerol, propylene glycol, ethylene glycol, sorbitol, or xylitol. In certain other embodiments, the at least one polyol compound is mannitol. In certain other embodiments, the at least one polyol compound is glycerol. In certain other embodiments, the at least one polyol compound is propylene glycol. In certain other embodiments, the at least one polyol compound is mannitol, and the solution further comprises glycerol. In certain other embodiments, the at least one polyol compound is mannitol, and the solution further comprises propylene glycol. In certain other embodiments, the at least one polyol compound is glycerol, and the solution further comprises propylene glycol. In certain other embodiments, the mannitol described in embodiments above is D-mannitol.

The amount of the at least one polyol compound in the aqueous ophthalmic solution may be selected in order to achieve desired performance properties for the solution. The polyol compound may, for example, increase the stability of the solution to storage and/or modify the tonicity of the solution to make it more suitable for administration to the eye of a patient. In certain embodiments, the aqueous ophthalmic solution comprises from about 2% (w/v) to about 5% (w/v) of the at least one polyol compound. In certain other embodiments, the aqueous ophthalmic solution comprises from about 3.5% (w/v) to about 4.5% (w/v) of the at least one polyol compound. In certain other embodiments, the aqueous ophthalmic solution comprises about 4% (w/v) of the at least one polyol compound. In certain other embodiments, the aqueous ophthalmic solution comprises from about 2% (w/v) to about 3% (w/v) mannitol, and about 0.5% (w/v) to about 1.5% (w/v) glycerin. In certain other embodiments, the mannitol described in embodiments above is D-mannitol.

In certain embodiments, the amount of polyol may be selected based on the amount of phentolamine (or pharmaceutically acceptable salt thereof), such that there is an inverse relationship between the amount of phentolamine (or pharmaceutically acceptable salt thereof) and the polyol in order to achieve isotonicity with the eye. For example, in embodiments where the aqueous ophthalmic solution contains about 2% (w/v) phentolamine, mannitol is present in the solution at a concentration of about 3% (w/v). In embodiments where the aqueous ophthalmic solution contains about 1% (w/v) phentolamine, mannitol is present in the solution at a concentration of about 4% (w/v). To further illustrate this principle, in embodiments where the aqueous ophthalmic solution contains about 0.5% (w/v) phentolamine, mannitol may be present in the solution at a concentration of about 4.5% (w/v). In certain embodiments, the mannitol described in embodiments above is D-mannitol.

It is appreciated that the aqueous ophthalmic solution can contain additional ingredients described herein, such as various polymer materials. One such embodiment is an aqueous ophthalmic solution comprising, for example, at least one polyol compound that is propylene glycol, and further comprising polypropylene glycol, such as polypropylene glycol having a weight average molecular weight in the range of about 5,000 g/mol to about 100,000 g/mol.

Poly(C$_{2-4}$Alkylene)Glycol Polymer

The aqueous ophthalmic solution may optionally comprise a poly(C$_{2-4}$alkylene)glycol polymer. An exemplary poly(C$_{2-4}$alkylene)glycol polymer is polypropylene glycol, such as a polypropylene glycol having a weight average molecular weight in the range of about 5,000 g/mol to about 100,000 g/mol, about 10,000 g/mol to about 50,000 g/mol, or about 50,000 g/mol to about 100,000 g/mol.

Dextran

The aqueous ophthalmic solution may optionally comprise dextran. Dextran is a commercially available, branched polysaccharide comprising glucose molecules. The amount of dextran in the aqueous ophthalmic solution may be selected to achieve certain performance properties. In certain embodiments, the aqueous ophthalmic solution comprises from about 0.01% (w/v) to about 2% (w/v) dextran. In certain other embodiments, the aqueous ophthalmic solution comprises from about 0.01% (w/v) to about 1% (w/v) dextran.

The dextran may be further characterized according to its weight average molecular weight. In certain embodiments, the dextran has a weight average molecular weight in the range of about 65,000 g/mol to about 75,000 g/mol. In certain other embodiments, the dextran has a weight average molecular weight of about 70,000 g/mol. In yet other embodiments, the dextran has a weight average molecular weight in the range of about 5,000 g/mol to about 100,000 g/mol, about 10,000 g/mol to about 50,000 g/mol, or about 50,000 g/mol to about 100,000 g/mol.

Cellulose Agent

The aqueous ophthalmic solution may optionally comprise a cellulose agent. Exemplary cellulose agents include, for example, cellulose, carboxymethyl cellulose, hydroxyethylcellulose, hydroxypropylcellulose, and hydroxypropylmethyl cellulose. In certain embodiments, the cellulose agent is hydroxypropylmethyl cellulose. In certain other embodiments, the cellulose agent is cellulose, carboxymethyl cellulose, hydroxyethylcellulose, or hydroxpropylcellulose. The amount of cellulose agent in the aqueous ophthalmic solution may be selected in order to achieve desired performance properties. For example, in certain embodiments, the aqueous ophthalmic solution comprises from about 0.01% (w/v) to about 2% (w/v) cellulose agent.

The cellulose agent may be further characterized according to its weight average molecular weight. In certain embodiments, the cellulose agent has a weight average molecular weight in the range of about 5,000 g/mol to about 100,000 g/mol, about 10,000 g/mol to about 50,000 g/mol, or about 50,000 g/mol to about 100,000 g/mol.

Buffer

The aqueous ophthalmic solution comprises at least one buffer. The buffer imparts to the solution a buffering capacity, that is, the capacity to neutralize, within limits, either acids or bases (alkali) with relatively little or no change in the original pH. The buffer may be an acid, a base, or a combination of an acid and a base. The buffer may be organic, inorganic, or a combination of organic and inorganic components. It should be understood that the buffer at least partially dissociates in aqueous solution to form a mixture of, e.g., an acid and conjugate base or a base and conjugate acid. For example, the buffer may be a combination of a carboxylic acid and its carboxylate salt (e.g., a combination of acetic acid and sodium acetate). In another embodiment, the buffer may be a combination of an acid and a base, where the acid and the base are not conjugates. For example, the acid may be boric acid and the base may be tris(hydroxymethyl)aminomethane (TRIS).

Exemplary buffers include organic acids (e.g., acetic acid, sorbic acid, and oxalic acid), a borate salt, a hydrogen carbonate salt, a carbonate salt, a gluconate salt, a lactate salt, a phosphate salt, a propionate salt, a perborate salt, tris-(hydroxymethyl)aminomethane (TRIS), bis(2-hydroxyethyl)-imino-tris-(hydroxymethyl)aminoalcohol (bis-tris), N-[2-hydroxy-1,1-bis(hydroxymethyl)ethyl]glycine (tricene), N-[2-hydroxy-1,1-bis(hydroxymethyl)ethyl]glycine, 3-(N-morpholino)propanesulfonic acid, N-(carbamoylmethyl)taurine (ACES), an amino acid, salts thereof, and combinations thereof. It should be understood that the salt form of a buffer may comprise any suitable counterion. For example, the salt form of an acid may comprise an alkali or alkaline earth metal counterion.

The buffer can be characterized according to its strength, i.e., the buffering capacity. The buffering capacity can be tested, for example, by determining the millimoles (mM) of strong acid or base (or respectively, hydrogen or hydroxide ions) required to change the pH of a buffer solution by one unit when added to one liter (a standard unit) of the buffer solution. The buffering capacity generally depends on the type and concentration of the buffer components and can be greater in particular pH ranges. For example, a buffer may have an optimal buffering capacity in a pH range near the pK$_a$ of the buffer, e.g., within about 1 pH unit or within about 2 pH units of the pK$_a$ the buffer. In certain embodiments, the buffer is a weak buffer, such as an alkali metal carboxylate (e.g., sodium acetate).

In certain embodiments, the buffer is a weak acid buffer having one or more of the following characteristics: (a) a pK$_a$ of from about 4.0 to about 6.0; more preferably, from about 4.5 to about 5.5; and (b) a lipophilicity value Log P of from about −0.50 to about 1.5; more preferably, from about −0.25 to about 1.35.

The amount of buffer can be adjusted in order to achieve desired performance properties for the aqueous ophthalmic solution. For example, in certain embodiments, the buffer may be present at a concentration of less than about 10 mM, less than about 7 mM, less than about 5 mM, less than about 3 mM, or less than about 2 mM. In some embodiments, the buffer may be present at a concentration of from about 1 mM to about 10 mM, from about 1 mM to about 7 mM, from about 1 mM to about 5 mM, from about 1 mM to about 3 mM, from about 1 mM to about 2 mM, from about 2 mM to about 5 mM, or from about 2 mM to about 3 mM. In yet other embodiments, the buffer is present at a concentration of about 3 mM.

The amount and identity of the buffer may be selected in order to achieve certain performance properties for the aqueous ophthalmic solution. For example, the amount of buffer may impact the quantity of acid that may be neutralized before there is substantial change in the pH of the aqueous ophthalmic solution. Also, the amount of buffer may impact the tonicity of the aqueous ophthalmic solution. Desirably, the quantity and identity of the buffer should be selected in order to minimize any irritation that may be caused by administration of the aqueous ophthalmic solution to the eye of a patient. Accordingly, in certain embodiments, the buffer is present at a concentration in the range of about 2 mM to about 4 mM. In yet other embodiments, the buffer is present at a concentration of about 3 mM. In certain embodiments, the buffer comprises an alkali metal alkylcarboxylate. In certain other embodiments, the buffer comprises an alkali metal acetate. In yet other embodiments, the buffer comprises sodium acetate.

Solution pH

The aqueous ophthalmic solution may be characterized according to the pH of the solution. Desirably, the aqueous ophthalmic solution has a pH in the range of 4.0 to 7.5. In certain embodiments, the aqueous ophthalmic solution has a pH in the range of 4.5 to 7.5. In certain embodiments, the solution has a pH in the range of 4.5 to 6.0. In certain other embodiments, the solution has a pH in the range of 4.5 to 5.5. In yet other embodiments, the solution has a pH in the range of 4.7 to 5.1.

Additional Materials for Aqueous Ophthalmic Solutions

The aqueous ophthalmic solutions may contain additional materials in order to make the composition more suitable for administration to the eye of a patient. Exemplary additional materials are described below and include, for example, a tonicity modifier, preservative, antioxidant, viscosity modifying agent, stabilizing agent, corneal permeation enhancing agent, and surfactants.

A. Tonicity Modifier

The aqueous ophthalmic solution may optionally comprise one or more tonicity modifiers. The tonicity modifier may be ionic or non-ionic. In certain embodiments, the tonicity modifier may be a salt, a carbohydrate, or a polyol. Exemplary tonicity modifiers include alkali metal or alkaline earth metal halides (such as LiBr, LiCl, LiI, KBr, KCl, KI, NaBr, NaCl, NaI, $CaCl_2$, and $MgCl_2$), boric acid, dextran (e.g., Dextran 70), cyclodextrin, dextrose, mannitol, glycerin, urea, sorbitol, propylene glycol, or a combination thereof.

It is appreciated that the tonicity modifier may be added to the aqueous ophthalmic solution in an amount sufficient to provide a desired osmolality. In certain embodiments, the tonicity modifier is present in the aqueous ophthalmic solution in an amount sufficient so that the aqueous ophthalmic solution has an osmolality ranging from about 50 to about 1000 mOsm/kg, from about 100 to about 400 mOsm/kg, from about 200 to about 400 mOsm/kg, or from about 280 to about 380 mOsm/kg. In certain embodiments, a tonicity modifier may be present in an amount ranging from about 0.01% (w/v) to about 7% (w/v), about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

B. Preservative

The aqueous ophthalmic solution may optionally comprise one or more preservatives in order to, for example, reduce or prevent microbial contamination. Exemplary preservatives include quaternary ammonium salts such as polyquaternium-1, cetrimide, benzalkonium chloride, or benzoxonium chloride; alkyl-mercury salts of thiosalicylic acid such as thiomersal, phenylmercuric nitrate, phenylmercuric acetate, or phenylmercuric borate; parabens such as methylparaben or propylparaben; alcohols such as chlorobutanol, benzyl alcohol, phenyl ethanol, cyclohexanol, 3-pentanol, or resorcinol; a peroxide; chlorine dioxide or PURITE; guanidine derivatives such as chlorohexidine gluconate or polyaminopropyl biguanide; and combinations thereof.

The amount of preservative can be adjusted in order to achieve desired performance properties for the aqueous ophthalmic solution. In certain embodiments, the preservative is present in an amount less than about 5% (w/v), 3% (w/v), 1% (w/v), or 0.1% (w/v) of the aqueous ophthalmic solution. In certain other embodiments, the preservative is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

C. Antioxidant

The aqueous ophthalmic solution may optionally comprise one or more antioxidants. Exemplary antioxidants for use in the aqueous ophthalmic solutions described herein include water soluble antioxidants such as ascorbic acid, cysteine hydrochloride, sodium bisulfate, sodium metabisulfite, sodium bisulfite, sodium sulfite, and the like; and oil-soluble antioxidants, such as ascorbyl palmitate, butylated hydroxyanisole (BHA), butylated hydroxytoluene (BHT), lecithin, propyl gallate, alpha-tocopherol, and the like.

The amount of antioxidant can be adjusted in order to achieve desired performance properties for the aqueous ophthalmic solution. In certain embodiments, the antioxidant is present in an amount less than about 5% (w/v), 3% (w/v), 1% (w/v), or 0.1% (w/v) of the aqueous ophthalmic solution. In certain other embodiments, the antioxidant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

D. Viscosity Modifying Agent

The aqueous ophthalmic solution may optionally comprise one or more viscosity modifying agents. The viscosity modifying agent may be used, for example, to increase the absorption of an active agent or increase the retention time of the aqueous ophthalmic solution in the eye. Exemplary viscosity modifying agents include polyvinylpyrrolidone, methylcellulose, hydroxypropyl methylcellulose, hydroxyethylcellulose, hydroxpropylcellulose, carboxymethylcellulose (CMC) and salts thereof (e.g., CMC sodium salt), gelatin, cellulose glycolate, sorbitol, niacinamide, an alpha-cyclodextran, polyvinyl alcohol, polyethylene glycol, hyaluronic acid, a polysaccharide, a monosaccharide, and combinations thereof.

The amount of viscosity modifying agent can be adjusted in order to achieve desired performance properties for the aqueous ophthalmic solution. In certain embodiments, the viscosity modifying agent is present in an amount less than about 10% (w/v), 5% (w/v), 3% (w/v), 1% (w/v), or 0.1% (w/v) of the aqueous ophthalmic solution. In certain other embodiments, the viscosity modifying agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution. In certain other embodiments, the viscosity modifying agent is present in an amount sufficient to provide an aqueous ophthalmic solution with a viscosity in the range of about 30 centipoise to about 100 centipoise.

The viscosity modifying agent may be a polymer that results in delayed release of one or more therapeutic agents in the solution. The identity of the polymer may be selected so as to achieve a desired time-release profile for the one or more therapeutic agents.

E. Corneal Permeation Enhancing Agent

The aqueous ophthalmic solution may optionally comprise one or more agents for enhancing corneal permeation of phentolamine (or a pharmaceutically acceptable salt thereof). Exemplary agents for enhancing corneal permeation include polymers, organic acids, esters of an organic acid (e.g., a monoglyceride of fatty acid having 8 to 12 carbon atoms), cyclodextrin, benzalkonium chloride (BAK), EDTA, caprylic acid, citric acid, boric acid, sorbic acid, polyoxyethylene-20-stearyl ether (PSE), polyethoxylated castor oil (PCO), deoxycholic acid sodium salt (DC), cetylpyridinium chloride (CPC), laurocapram, hexamethylenelauramide, hexamethyleneoctanamide, decylmethylsulfoxide, methyl sulfone, dimethyl sulfoxide, and combinations thereof.

The amount of corneal permeation enhancing agent can be adjusted in order to achieve desired performance properties for the aqueous ophthalmic solution. In certain embodiments, the corneal permeation enhancing agent is present in an amount less than about 10% (w/v), 5% (w/v), 1% (w/v), or 0.1% (w/v) of the aqueous ophthalmic solution. In certain other embodiments, the corneal permeation enhancing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), about 0.05% (w/v) to about 0.5% (w/v), about 1% (w/v) to about 3% (w/v), or about 2% (w/v) to about 4% (w/v), of the aqueous ophthalmic solution.

F. Solubilizing Agent

The aqueous ophthalmic solution may optionally comprise one or more solubilizing agents to improve the solubility of phentolamine (or a pharmaceutically acceptable salt thereof) in the aqueous ophthalmic solution. Exemplary solubilizing agents include, for example, a fatty acid glycerol poly-lower alkylene (i.e., a $C_1$ to $C_7$, linear or branched) glycol ester, fatty acid poly-lower alkylene glycol ester, polyalkylene glycol (e.g., polyethylene glycol), glycerol ether of vitamin E, tocopherol polyethylene glycol 1000 succinate (TPGS), tyloxapol, polysorbate 20, polysorbate 40, polysorbate 60, polysorbate 80, polyoxyethylene/polyoxypropylene surfactants (e.g., Pluronic F-68, F-84 and P-103), cyclodextrin, and combinations thereof.

The amount of solubilizing agent can be adjusted in order to achieve desired performance properties for the aqueous ophthalmic solution. In certain embodiments, the solubilizing agent is present in an amount less than about 10% (w/v), 5% (w/v), 3% (w/v), 1% (w/v), or 0.10% (w/v) of the aqueous ophthalmic solution. In certain other embodiments, the solubilizing agent is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

G. Stabilizing Agent

The aqueous ophthalmic solution may optionally comprise one or more stabilizing agents in order to improve the stability of the aqueous ophthalmic solution to storage, etc. Stabilizing agents described in the pharmaceutical literature are contemplated to be amenable for use in the aqueous ophthalmic solutions described herein. Exemplary stabilizing agents include an alcohol (e.g., polyols, such as mannitol, glycerol, propylene glycol, sorbitol, and xylitol), poly-alkylene glycols such as polyethylene glycol, polypropylene glycol, polyethylene glycol-nonphenol ether, polyethylene glycol sorbitan monolaurate, polyethylene glycol sorbitan monooleate, polyethylene glycol sorbitan monooleate, polyethylene glycol stearate, polyethylene glycol polypropylene glycol ether, polyvinyl alcohol, polyvinyl pyrrolidine, ascorbic acid, vitamin E, N-acetylcamosine (NAC), sorbic acid, and combinations thereof. In certain embodiments, the stabilizing agent is a polymer, such as one of the polymers mentioned above.

The amount of stabilizing agent can be adjusted in order to achieve desired performance properties for the aqueous ophthalmic solution. In certain embodiments, the stabilizing agent is present in an amount less than about 10% (w/v), 5% (w/v), or 1% (w/v) of the aqueous ophthalmic solution. In certain other embodiments, the stabilizing agent is present in an amount ranging from about 0.01% (w/v) to about 5% (w/v), about 0.01% (w/v) to about 1% (w/v), or about 0.01% (w/v) to about 0.1% (w/v) of the aqueous ophthalmic solution.

H. Surfactant

The aqueous ophthalmic solution may optionally comprise one or more surfactants. Exemplary surfactants include Polysorbate 20 (i.e., polyoxyethylene (20) sorbitan monolaurate), Polysorbate 40 (i.e., polyoxyethylene (20) sorbitan monopalmitate), Polysorbate 60 (i.e., polyoxyethylene (20) sorbitan monostearate), Polysorbate 80 (i.e., polyoxyethylene (20) sorbitan monooleate), glyceryl stearate, isopropyl stearate, polyoxyl stearate, propylene glycol stearate, sucrose stearate, polyethylene glycol, a polypropylene oxide, a polypropylene oxide copolymer, Pluronic F68, Pluronic F-84, Pluronic P-103, an alcohol ethoxylate, an alkylphenol ethoxylate, an alkyl glycoside, an alkyl polyglycoside, a fatty alcohol, hydroxypropylmethyl cellulose (HPMC), carboxymethyl cellulose (CMC), cyclodextrin, a polyacrylic acid, phosphatidyl chloline, phosphatidyl serine, and combinations thereof.

The amount of surfactant can be adjusted in order to achieve desired performance properties for the aqueous ophthalmic solution. In certain embodiments, the surfactant is present in an amount less than about 10% (w/v), 5% (w/v), 3% (w/v), 1% (w/v), or 0.1% (w/v) of the aqueous ophthalmic solution. In certain other embodiments, the surfactant is present in an amount ranging from about 0.01% (w/v) to about 5% (w/v), about 0.01% (w/v) to about 1% (w/v), about 0.1% (w/v) to about 1% (w/v), about 0.05% (w/v) to about 5% (w/v), or about 0.05% (w/v) to about 0.5% (w/v), of the aqueous ophthalmic solution.

I. Demulcent Polymers

The aqueous ophthalmic solution may optionally comprise one or more demulcent polymers. Because of their ability to hold large amounts of water, demulcent polymers are useful for coating and moisturizing the cornea of the eye. Exemplary demulcent polymers include cellulose derivatives, dextran 40, dextran 70, gelatin, and liquid polyols.

J. Wetting Agents

The aqueous ophthalmic solution may optionally comprise one or more wetting agents. Wetting agents can be used to wet the surface of the eye. Exemplary wetting agents include polysorbates, poloxamers, tyloxapol, and lecithin.

K. Additional Materials

The aqueous ophthalmic solutions may optionally comprise one or more additional materials, such as acetylcysteine, cysteine, sodium hydrogen sulfite, butyl-hydroxyanisole, butyl-hydroxytoluene, alpha-tocopherol acetate, thiourea, thiosorbitol, sodium dioctyl sulfosuccinate, monothioglycerol, lauric acid sorbitol ester, triethanol amine oleate, or palmitic acid esters.

Further, the aqueous ophthalmic solutions may comprise a carrier, such as one or more of the exemplary carriers are described in for example, Martin, Remington's Pharmaceutical Sciences, 15th Ed., Mack Publ. Co., Easton, PA [1975]). The carrier can be, for example, a mixture of water and a water-miscible solvent (e.g., an alcohol such as glycerin, a vegetable oil, or a mineral oil). Other exemplary carriers include a mixture of water and one or more of the following materials: hydroxyethylcellulose, carboxymethylcellulose, methylcellulose, an alkali metal salt of carboxymethylcellulose, hydroxymethylcellulose, methylhydroxypropylcellulose, hydroxypropylcellulose, ethyl oleate, polyvinylpyrrolidone, an acrylate polymer, a methacrylate polymer, a polyacrylamide, gelatin, an alginate, a pectin, tragacanth, karaya gum, xanthan gum, carrageenin, agar, acacia, a starch (such as starch acetate or hydroxypropyl starch), polyvinyl alcohol, polyvinyl methyl ether, polyethylene oxide, or a cross-linked polyacrylic acid.

Exemplary Aqueous Ophthalmic Solutions

The aqueous ophthalmic solutions having been generally described above will now be more specifically described by reference to the following more specific examples. The following more specific examples are only exemplary and are not intended to limit the scope of the invention in any way.

One such exemplary solution is an aqueous ophthalmic solution free of a chelating agent comprising: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.25% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4 to 6.

Another such exemplary solution is an aqueous ophthalmic solution free of a chelating agent comprising: (a) about 0.5% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the at least one polyol is mannitol. In certain embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 2% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Another such exemplary solution is an aqueous ophthalmic solution free of a chelating agent comprising: (a) about 0.25% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4.5 to 5.5 and does not contain a chelating agent.

The aqueous ophthalmic solution may be more specifically defined according to the following embodiments. For example, in certain embodiments, the aqueous ophthalmic solution comprises from about 0.25% (w/v) to about 1% (w/v) of phentolamine mesylate. In certain other embodiments, the aqueous ophthalmic solution comprises from about 1% (w/v) to about 4% (w/v) mannitol. In certain other embodiments, the aqueous ophthalmic solution comprises 4% (w/v) mannitol. In certain embodiments, the alkali metal acetate is sodium acetate. In certain other embodiments, the aqueous ophthalmic solution comprises 3 mM sodium acetate. In still other embodiments, the aqueous ophthalmic solution consists of (i) about 0.5% (w/v) to about 1% (w/v) of phentolamine mesylate; (ii) about 1% (w/v) to about 6% (w/v) of one or more polyol compounds selected from the group consisting of mannitol, glycerol, and propylene glycol; (iii) about 1 mM to about 6 mM of an alkali metal acetate; (iv) acetic acid; and (v) water; wherein the solution has a pH in the range of 4.5 to 5.5.

Further exemplary aqueous ophthalmic solutions are provided in Tables 1-3 below, where in each instance the solution has a pH in the range of 4.7 to 5.1.

TABLE 1

EXEMPLARY AQUEOUS OPHTHALMIC SOLUTIONS.

| | Formulation No. | | | | | | | |
|---|---|---|---|---|---|---|---|---|
| Component | A1 | B1 | C1 | D1 | E1 | F1 | G1 | H1 |
| Phentolamine mesylate (% w/v) | 1.5 | 1 | 0.5 | 1 | 1 | 1 | 1 | 1 |
| Mannitol (% w/v) | 4 | 4 | 4 | 3 | 3 | 2 | 2 | 4 |
| Sodium acetate (mM) | 3 | 3 | 3 | 3 | 3 | 3 | 3 | 3 |
| Glycerol (% w/v) | 0 | 0 | 0 | 0.5 | 0 | 1 | 0 | 0) |
| Propylene glycol (% w/v) | 0 | 0 | 0 | 0 | 0.5 | 0 | 1 | 0 |

TABLE 1-continued

EXEMPLARY AQUEOUS OPHTHALMIC SOLUTIONS.

| Component | Formulation No. | | | | | | | |
|---|---|---|---|---|---|---|---|---|
| | A1 | B1 | C1 | D1 | E1 | F1 | G1 | H1 |
| Dextran 70 (% w/v) | 0 | 0 | 0 | 0 | 0 | 0 | 0 | 0.1 |
| Water | q.s. | q.s | q.s. | q.s. | q.s. | q.s. | q.s. | q.s. |

TABLE 2

EXEMPLARY AQUEOUS OPHTHALMIC SOLUTIONS.

| Component | Formulation No. | | | | | |
|---|---|---|---|---|---|---|
| | A2 | B2 | C2 | D2 | E2 | F2 |
| Phentolamine mesylate (% w/v) | 0.25 | 0.25 | 0.25 | 0.25 | 0.25 | 0.25 |
| Mannitol (% w/v) | 4 | 3 | 3 | 2 | 2 | 4 |
| Sodium acetate (mM) | 3 | 3 | 3 | 3 | 3 | 3 |
| Glycerol (% w/v) | 0 | 0.5 | 0 | 1 | 0 | 0 |
| Propylene glycol (% w/v) | 0 | 0 | 0.5 | 0 | 1 | 0 |
| Dextran 70 (% w/v) | 0 | 0 | 0 | 0 | 0 | 0.1 |
| Water | q.s. | q.s. | q.s. | q.s. | q.s. | q.s. |

TABLE 3

EXEMPLARY AQUEOUS OPHTHALMIC SOLUTIONS.

| Component | Formulation No. | | | | | | | |
|---|---|---|---|---|---|---|---|---|
| | A3 | B3 | C3 | D3 | E3 | F3 | G3 | H3 |
| Phentolamine mesylate (% w/v) | 1.5 | 1 | 0.5 | 0.25 | 1 | 1 | 1 | 1 |
| Mannitol (% w/v) | 4 | 4 | 4 | 4 | 3 | 2 | 2 | 4 |
| Sodium acetate (mM) | 3 | 3 | 3 | 3 | 3 | 3 | 2 | 3 |
| Water | q.s. | q.s. | q.s. | q.s. | q.s. | q.s. | q.s. | q.s. |

Another exemplary aqueous ophthalmic solution comprises phentolamine mesylate (e.g., at 100 w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), dextran having a weight average molecular weight of about 70,000 g/mol (e.g., at 0.1% w/v), hydroxypropyl methylcellulose (e.g., at 0.3% w/v), potassium chloride, purified water, sodium borate, and sodium chloride; wherein the solution has a pH in the range of 4 to 6. In certain other embodiments, the aqueous ophthalmic solution consists of phentolamine mesylate (e.g., at 10% w/v), mannitol (e.g., at 4% w/v), dextran having a weight average molecular weight of about 70,000 g/mol (e.g., at 0.100 w/v), hydroxypropyl methylcellulose (e.g., at 0.3% w/v), potassium chloride, purified water, sodium borate, and sodium chloride; wherein the solution has a pH in the range of 4.5 to 5.1.

Another exemplary aqueous ophthalmic solution comprises phentolamine mesylate (e.g., at 1% w/v), mannitol (e.g., at 4% w/v), sodium acetate (e.g., at 3 mM), and water, wherein the solution has a pH in the range of about 4 to about 6. In certain embodiments, the solution has a pH in the range of 4.5 to 5.1. In certain embodiments, the aqueous ophthalmic solution consists essentially of phentolamine mesylate (e.g., at 1% w/v), mannitol (e.g., at 4% w/v), sodium acetate (e.g., at 3 mM), and water, wherein the solution has a pH in the range of 4 to 6. In certain embodiments, the aqueous ophthalmic solution comprises phentolamine mesylate at 1% w/v, mannitol 4% w/v, sodium acetate at 3 mM, and water, wherein the solution has a pH in the range of 4.5 to 5.1. In certain other embodiments, the aqueous ophthalmic solution consists of phentolamine mesylate (e.g., at 1% w/v), mannitol (e.g., at 4% w/v), sodium acetate (e.g., at 3 mM), and water, wherein the solution has a pH in the range of 4.5 to 5.1. In certain embodiments, the aqueous ophthalmic solution consists essentially of phentolamine mesylate at 1% w/v, mannitol 4% w/v, sodium acetate at 3 mM, and water, wherein the solution has a pH in the range of 4.5 to 5.1.

Yet another exemplary solution is an aqueous ophthalmic solution free of a chelating agent that comprises: (a) about 0.1% (w/v) to about 2% (w/v) of phentolamine mesylate; (b) about 1% (w/v) to about 6% (w/v) of at least one polyol compound selected from the group consisting of is mannitol, glycerol, and propylene glycol; (c) about 1 mM to about 6 mM of an alkali metal acetate; and (d) water; wherein the solution has a pH in the range of 4 to 6 and does not contain a chelating agent.

Yet another exemplary solution is an aqueous ophthalmic solution free of a chelating agent that comprises: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.1% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b)

about 4% mannitol; (c) about 3 mM sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.25% (w/v) to about 2% (w/v) of phentolamine mesylate; (b) about 3% (w/v) to about 5% (w/v) of mannitol; (c) about 2 mM to about 4 mM of a buffer comprising sodium acetate; and (d) water; wherein the solution has a pH in the range of 4.5 to 5.2 and does not contain a chelating agent.

Yet another exemplary solution is an aqueous ophthalmic solution free of a chelating agent that comprises: (a) about 0.5% (w/v) to about 2% (w/v) of phentolamine mesylate; (b) about 3% (w/v) to about 5% (w/v) of mannitol; (c) about 2 mM to about 4 mM of a buffer comprising sodium acetate; and (d) water; wherein the solution has a pH in the range of 4.6 to 5.2 and does not contain a chelating agent.

Yet another exemplary solution is an aqueous ophthalmic solution free of a chelating agent that comprises: (a) about 0.5% (w/v) to about 1% (w/v) of phentolamine mesylate; (b) about 3% (w/v) to about 5% (w/v) of mannitol; (c) about 1 mM to about 4 mM of a buffer comprising sodium acetate; and (d) water; wherein the solution has a pH in the range of 4.6 to 5.2 and does not contain a chelating agent.

Yet another exemplary solution is an aqueous ophthalmic solution free of a chelating agent, comprising: (a) about 0.1% (w/v) to about 1% (w/v) of phentolamine mesylate; (b) about 4% mannitol; (c) about 3 mM of a buffer comprising sodium acetate; and (d) water; wherein the solution has a pH in the range of 4.6 to 5.2 and does not contain a chelating agent. In certain embodiments, the aqueous ophthalmic solution free of a chelating agent that comprises about 0.25% (w/v) to about 1% (w/v) of phentolamine mesylate.

Yet another exemplary solution is an aqueous ophthalmic solution free of a chelating agent, comprising: (a) about 0.5% (w/v) to about 1% (w/v) of phentolamine mesylate; (b) about 4% mannitol; (c) about 3 mM of a buffer comprising sodium acetate; and (d) water; wherein the solution has a pH in the range of 4.6 to 5.2 and does not contain a chelating agent.

Stability Features of Aqueous Ophthalmic Solutions

The aqueous ophthalmic solutions described herein may be further characterized according to their stability features, such as the percentage of phentolamine (or pharmaceutically acceptable salt thereof) that is present in the aqueous ophthalmic solution after storage for a certain length of time. As explained above, one of the benefits of the present aqueous ophthalmic solutions is that they possess good stability over extended periods of time, even though they do not have a chelating agent.

Accordingly, in certain embodiments, the aqueous ophthalmic solution is characterized by less than 2% by weight of the phentolamine or pharmaceutically acceptable salt thereof degrades upon storage of the solution at 25° C. for 12 weeks. In certain other embodiments, the aqueous ophthalmic solution is characterized by less than 2% by weight of the phentolamine or pharmaceutically acceptable salt thereof degrades upon storage at 25° C. for 24 weeks (or 36 weeks or 48 weeks). In yet other embodiments, less than 7% by weight of the phentolamine or pharmaceutically acceptable salt thereof degrades upon storage at 40° C. for 12 weeks (or 24, 36, or 48 weeks). In yet other embodiments, the aqueous ophthalmic solution is characterized by less than 10% by weight of the phentolamine or pharmaceutically acceptable salt thereof degrades upon storage at 25° C. for 18 months, 24 months, or 36 months. In yet other embodiments, the aqueous ophthalmic solution is characterized by less than 10% by weight of the phentolamine or pharmaceutically acceptable salt thereof degrades upon storage at temperature in the range of 2-8° C. for 18 months, 24 months, or 36 months. In yet other embodiments, the aqueous ophthalmic solution is characterized by less than 4% by weight (or preferably less than 3% by weight) of the phentolamine or pharmaceutically acceptable salt thereof degrades upon storage at 25° C. for 18 months, 24 months, or 36 months. In yet other embodiments, less than 10% by weight of the phentolamine or pharmaceutically acceptable salt thereof degrades upon storage at 40° C. for 4, 5, or 6 months.

Polyvinylpyrrolidone Artificial Tears Formulation

Another ophthalmic solution contemplated for use in the present invention is an ophthalmic solution comprising an alpha-adrenergic antagonist (e.g., phentolamine or a pharmaceutically acceptable salt thereof) and a polyvinylpyrrolidone artificial tears composition. Exemplary polyvinylpyrrolidone artificial tears compositions are described in, for example, U.S. Pat. Nos. 5,895,654; 5,627,611; and 5,591,426; and U.S. Patent Application Publication No. 2002/0082288, all of which are hereby incorporated by reference. Artificial tears compositions are understood to promote wettability and spread, have good retention and stability on the eye, and desirably do not cause any significant discomfort to the user. Accordingly, an exemplary polyvinylpyrrolidone artificial tear composition comprises: (1) polyvinylpyrrolidone, preferably in the amount of about 0.1-5% by weight of the solution; (2) benzalkonium chloride, preferably in an amount of about 0.01-0.10% by weight of the solution; (3) hydroxypropyl methylcellulose, preferably in an amount of about 0.2-1.5% by weight of the solution; (4) glycerin, preferably in an amount of about 0.2-1.0% by weight of the solution, and (5) water, wherein the composition is an aqueous solution having isotonic properties.

Sustained Release Delivery Systems

When it is desirable to have sustained release of one or more therapeutic agents to the patient, the therapeutic agent(s) may be administered to the patient in the form of a sustained release delivery system. Sustained release delivery systems are described in the published literature. Exemplary sustained release delivery systems include intracanalicular inserts, a slow release contact lens, a bio-erodible IVT insert, and an intracameral insert. Inserts may be biodegradable or non-biodegradable. Exemplary materials described in the literature for use in sustained release delivery systems include a mixture of EVA and PVA polymers, a mixture of silicone and PVA polymer, a mixture of polyimide and PVA polymer, a mixture of PMMA and EVA polymers, PLGA polymer, and liposomes.

IV. Medical Kits

Another aspect of the invention provides a medical kit comprising, for example, (i) a therapeutic agent described herein, and (ii) instructions for treating glaucoma, ocular hypertension, and/or other ocular disorders according to methods described herein.

EXAMPLES

The invention now being generally described, will be more readily understood by reference to the following examples, which are included merely for purposes of illustrating certain aspects and embodiments of the present invention, and are not intended to limit the invention.

Example 1—Reduction in Intraocular Pressure by Phentolamine Mesylate in Healthy Human Subjects Having Normal Intraocular Pressure An aqueous solution containing phentolamine mesylate was applied as an eye drop to the eye of healthy human subjects having normal intraocular pressure, and reduction in intraocular pressure in the eye was measured. Experimental procedures and results are described below.

Part I—Experimental Procedures

One of the test articles in Table 1 was administered in the form an eye drop to the eye of a healthy human subject having normal intraocular pressure. Intraocular pressure of the subject's eye was measured before administration of the test article and then again 2-3 hours after administration of test article.

TABLE 1

| Test Article | Description |
| --- | --- |
| 0.5% PM | 0.5% w/w phentolamine mesylate in aqueous vehicle |
| 1% PM | 1% w/w phentolamine mesylate in aqueous vehicle |
| Placebo | aqueous vehicle without phentolamine mesylate |

Part II—Results

Results are provided in Tables 2 and 3 below. The abbreviation IOP refers to intraocular pressure.

TABLE 2

| | Statistic | 1.0% PM | 0.5% PM | Placebo |
| --- | --- | --- | --- | --- |
| Screen | N (number of eyes) | 40 | 40 | 40 |
| | Mean Intraocular Pressure | 16.6 | 16.7 | 16.08 |
| | SD | 2.479 | 2.738 | 2.280 |
| | Median Intraocular Pressure | 16.0 | 17.0 | 16.0 |
| | Minimum Intraocular Pressure | 12.0 | 11.0 | 12.0 |
| | Maximum Intraocular Pressure | 21.0 | 21.0 | 21.0 |
| Day 1 Post-dose | N (number of eyes) | 40 | 40 | 40 |
| | Mean Intraocular Pressure | 14.18 | 15.38 | 16.18 |
| | SD | 2.908 | 3.621 | 3.202 |
| | Median Intraocular Pressure | 14 | 16 | 16.5 |
| | Minimum Intraocular Pressure | 9 | 8 | 10 |
| | Maximum Intraocular Pressure | 21 | 21 | 22 |
| Change from Screening | N (number of eyes) | 40 | 40 | 40 |
| | Mean Intraocular Pressure | 2.42 | 1.32 | −0.10 |
| | SD | −0.429 | −0.883 | −0.922 |
| | Median Intraocular Pressure | 2 | 1 | −0.5 |
| | Statistic | 1.0% PM | 0.5% PM | Placebo |
| | Minimum Intraocular Pressure | 3 | 3 | 2 |
| | Maximum Intraocular Pressure | 0 | 0 | −1 |
| P-value | | <0.0001 | 0.01483 | |

TABLE 3

| | Placebo | 0.5% w/w PM | 1% w/w PM |
| --- | --- | --- | --- |
| | Absolute Change (mm Hg) | | |
| All IOP | −0.13 | 1.46 | 2.26 |
| IOP >17 | 0.87 | 2.29 | 3.00 |
| IOP >18 | 1.18 | 2.06 | 3.13 |
| | Percent Change (mm Hg) | | |
| All IOP | −0.80% | 8.71% | 13.69% |
| IOP >17 | −4.71% | 12.12% | 15.93% |
| IOP >18 | 6.25% | 10.70% | 16.39% |

Example 2—Reduction in Intraocular Pressure by Phentolamine Mesylate in Human Subjects with Intraocular Pressure of at Least 22 mmHG Ability of phentolamine mesylate to reduce intraocular pressure (IOP) in the eye of a human subject having an IOP≥22 mmHg may be evaluated according to a clinical study in which an aqueous ophthalmic solution containing phentolamine mesylate is administered to the eye of a patient, and then the patient is evaluated for reduction in intraocular pressure in the eye that received the aqueous ophthalmic solution containing phentolamine mesylate. Experimental procedures and results are described below.

Part I—Experimental Procedures

Human subjects are screened for potential enrollment and, if qualified, enrolled in the study. Inclusion criteria and exclusion criteria for the study are set forth below. If a subject does not meet the inclusion/exclusion criteria but the investigator believes the subject should be in the study, a deviation may be allowed following a discussion between the Principal Investigator and Sponsor of the study.

Inclusion Criteria
  Written informed consent to participate in this trial.
  Males or females greater than 45 years of age.
  Good general health.
  Baseline IOP≥22 mmHG.
  BCDVA of 20/40 or better in at least one eye.
  Able and willing to give informed consent and comply with all protocol mandated procedures.

Exclusion Criteria
  Cataract(s).
  Ocular trauma within the past six months, or ocular surgery or laser treatment within the past three months.
  Refractive surgery or cataract surgery in either eye.
  Use of ocular medication within 4 weeks of Visit 1.
  Clinically significant ocular disease (e.g., corneal edema, uveitis, severe keratoconjunctivitis sicca, retinal degenerative disease) which might interfere with the study.
  Any abnormality preventing reliable applanation tonometry of either eye.
  Known hypersensitivity or contraindication to phentolamine mesylate, or any component of the formulation, or to topical anesthetics.
  Contraindications to phentolamine (including history of myocardial infarction, cerebrovascular spasm, cerebrovascular occlusion, coronary insufficiency, angina, or other evidence suggestive of coronary artery disease).
  Low blood pressure—systolic <100 mm Hg or diastolic <60 mm Hg.
  A history of heart rate abnormalities, such as tachycardia or arrhythmias.
  Clinically significant systemic disease (e.g., uncontrolled diabetes, myasthenia gravis, hepatic, renal, cardiovascular or endocrine disorders) which might interfere with the study.
  Use of any topical or systemic alpha adrenergic or cholinergic drugs up to 30 days prior to screening, or during the study.
  Changes of systemic medication that could have a substantial effect on ocular autonomic pupil tone 4 weeks prior to screening, or anticipated during the study.
  Participation in any investigational study within the past 30 days.

Human subjects enrolled in the study shall randomized into two (or more) Treatment Groups with a 1:1 randomization. The Treatment Groups will receive single doses of either:
  Placebo Ophthalmic Solution,
  1% w/w Phentolamine Mesylate Ophthalmic Solution, or
  2% w/w Phentolamine Mesylate Ophthalmic Solution.
Description of the study medications is provided in Table 1.

TABLE 1

Study Medication

| Study Medication | Composition of Study Medication |
| --- | --- |
| Placebo Ophthalmic Solution | 4% w/w mannitol<br>3 mM sodium acetate<br>water<br>pH in the range 4.8 to 5.0 |
| 1% w/w Phentolamine Mesylate Ophthalmic Solution | 1% w/w phentolamine mesylate<br>4% w/w mannitol<br>3 mM sodium acetate<br>water<br>pH in the range 4.8 to 5.0 |
| 2% w/w Phentolamine Mesylate Ophthalmic Solution | 2% w/w phentolamine mesylate<br>4% w/w mannitol<br>3 mM sodium acetate<br>water<br>pH in the range 4.8 to 5.0 |

Doses of study medication are given once daily for one or more weeks; each subject will receive all the treatments. One or more of intraocular pressure, pupil diameter, Best Corrected Distance Visual Acuity (BCDVA), Distance Corrected Near Vision Acuity (DCNVA), Vision questionnaire, and Near Visual Acuity (NVA) will be measured at the screening visit, and throughout the study.

Example 3—Reduction in Intraocular Pressure by Phentolamine Mesylate in Human Subjects with Bilateral Open-Angle Glaucoma or Ocular Hypertension Ability of phentolamine mesylate to reduce intraocular pressure in the eye of a human subject with bilateral open-angle glaucoma or ocular hypertension may be evaluated according to a clinical study in which an aqueous ophthalmic solution containing phentolamine mesylate is administered to the eye of a patient, and then the patient is evaluated for reduction in intraocular pressure in the eye that received the aqueous ophthalmic solution containing phentolamine mesylate. Experimental procedures and results are described below.

Part I—Experimental Procedures

Human subjects are screened for potential enrollment and, if qualified, enrolled in the study. Inclusion criteria and exclusion criteria for the study are set forth below.
Inclusion Criteria
  18 years of age or older.
  Diagnosis of bilateral primary open angle glaucoma or ocular hypertension.
  One qualifying IOP criteria after washout:
  Baseline (Day 0) at T0 (T0=8 am±30 min) IOP≥23 mmHg in the study eye.
  IOP criteria after washout ≤32 mmHg OU at all time points.
  Best-corrected visual acuity (BCVA) in both eyes of 20/200 or better on Snellen, equivalent to +1.0 log Mar.
  Able and willing to sign informed consent, follow study instructions and complete all study visits.
  As applicable, must be willing to discontinue the use of all ocular hypotensive medication(s) in both eyes prior to receiving the study medication and for the entire course of the study.
  Able to self-administer or have a caretaker administer study eye drops.
Exclusion Criteria
  Closed or very narrow angles (Grade 0-1) or those the investigator judges as occludable and/or with evidence of peripheral anterior synechiae (PAS)≥180 degrees by gonioscopy within 6 months prior to Screening Visit in either eye. (Patent laser iridotomy with Grade 1-2 angles is acceptable in either eye, providing the PAS criteria are still met).
  Previous glaucoma intraocular surgery in either eye. Prior laser trabeculoplasty (ALT or SLT) in either eye is allowed if performed more than 6 months prior to Screening Visit.
  Any non-glaucoma intraocular surgery within 3 months prior to Screening Visit in either eye.
  Intraocular laser surgery such as laser capsulotomy, laser iridotomy, and/or retinal laser within 1 month prior to Screening Visit in either eye.
  Significant media opacity in either eye that would impede adequate posterior segment examination.
  Contraindications to pupil dilation in either eye.
  Other forms of glaucoma such as primary congenital, juvenile onset, chronic angle closure, and secondary glaucoma of any type including steroid-induced, inflammation-induced, or exfoliation glaucoma in either eye. Pigment dispersion syndrome/glaucoma is permitted in either eye.

Clinically significant corneal dystrophy, epithelial or endothelial disease, corneal irregularities or scarring that, in the investigator's judgment, would impede an accurate measurement of IOP or visualization of intraocular anatomy in the study eye.

History of refractive surgery in either eye (i.e., radial keratotomy, photorefractive keratectomy, LASIK).

History of corneal cross-linking procedure in either eye.

Unwillingness to be contact lens free during study participation.

Any history of uveitis, keratitis, or scleritis in either eye.

Any history of penetrating ocular trauma in either eye.

History within 3 months prior to Screening Visit of clinically significant moderate or severe chronic or active blepharitis, ocular dermatitis, or recent ocular conjunctivitis and/or ocular inflammation in either eye. Mild blepharitis, hyperemia (due to prostaglandin use) and/or blepharitis, and/or mild inactive seasonal allergic conjunctivitis and non-infective dermatitis are acceptable.

Corneal thickness <480 or >620 μm in the study eye. Pachymetry measurement within 6 months prior to Screening Visit is acceptable.

Advanced or severe glaucoma with progressive visual field loss and/or optic nerve changes in either eye that, in the investigator's best judgment, prevent safe withdrawal from treatment for the time periods required in this protocol.

Progressive retinal (including, but not limited to worsening dry age-related macular degeneration (AMD), presence of active wet AMD, or unstable diabetic retinopathy) or optic nerve disease in either eye from any cause other than glaucoma.

Any prior intravitreal steroid injection in either eye.

Sub-tenon's, sub-conjunctival or periocular steroid injections within the 6 months prior to Screening Visit in either eye.

Any use of ocular topical corticosteroids in either eye within 7 days, or chronic (as determined by the investigator) topical steroids within 28 days prior to Baseline and ensuing trial participation.

Known hypersensitivity to any component of the study medication, or to topical anesthetics or diagnostic drops used during the study.

Any ocular, condition that, in the investigator's judgment, could prevent the subject from safe participation the study.

Planned ocular surgery or intraocular injection procedure in either eye during study participation.

Participation in a clinical study with use of any investigational drug or treatment within 30 days prior to Baseline (Day 0).

Clinically significant abnormalities in: laboratory tests, physical examination, vital signs and/or ECG at Screening Visit. If in the investigator's judgment a subject with clinically significant abnormalities is appropriate for enrollment in the study, a discussion between the investigator and the Medical Monitor must occur and be documented prior to enrollment of this subject in the study.

Clinically significant systemic, psychiatric or psychological disease (for example, renal, hepatic, uncontrolled diabetes, uncontrolled blood pressure, autoimmune disorders, psychiatric disorders, endocrine disorders, or any other disorders) or dependency which, in the investigator's judgment, would be unsafe and interfere with interpretation of the study results or the subject's ability to comply with the study requirements.

Anticipated changes or initiation of medications which might affect IOP and/or systemic blood pressure within 7 days prior to Baseline/Day 0 (e.g., oral anti-hypertensives such as sympathomimetic agents, beta-adrenergic blocking agents, alpha agonists, alpha adrenergic blocking agents, calcium channel blockers, angiotensin converting enzyme inhibitors; [diuretics are allowed]), and 2 months prior to Baseline/Day 0 for corticosteroids (i.e., oral, nasal, topical [dermal, mucosal], and/or inhaled corticosteroids). If there are no further anticipated changes in medications that could affect IOP and/or systemic blood pressure, then once the subject is stable on their new dose of medication for the required time period, the subject may complete the Baseline Visit, assuming that all other screening requirements are met. Medications used on an adjustable or sliding scale based on testing results are allowed.

Known history of Hepatitis B+C, HIV+, or AIDS and/or inadequate venous access.

Women of childbearing potential who are pregnant, nursing, planning a pregnancy, or not using a medically acceptable form of birth control. An adult woman is considered to be of childbearing potential unless she is one year post-menopausal or three months post-surgical sterilization. All females of childbearing potential must have a negative serum pregnancy test result at Screening Visit and a negative urine and serum pregnancy test at Baseline (Day 0) prior to randomization in the study and must not intend to become pregnant during the study.

History of drug or alcohol abuse within the last 5 years.

Related to site study staff and/or site employees.

For human subjects enrolled in the study, the human subject is assigned to a Treatment Group in random order. There will be two or more Treatment Groups, as set forth in Table 1 below. Subjects enrolled in the study will discontinue use of their ocular hypotensive therapy during the washout period. The duration of the washout period will depend on the subject's pre-study ocular hypotensive therapy.

Human subjects shall receive study medication as set forth in Table 1 according to the Treatment Group to which the subject is assigned. Study medication is listed in Table 2. Evaluations of human subjects are performed at the Screening Visit, optionally before treatment on Study Days 0, 7, 14, and 21, and then on Day 28. All human subjects are examined seven days after the last dose for follow-up evaluation.

TABLE 1

Treatment Groups

| Treatment Group | Study Medication and Administration Protocol |
|---|---|
| 1 | One drop of 1% w/w Phentolamine Mesylate Ophthalmic Solution in each eye daily before bedtime for 28 days from Day 1 to Day 28. |
| 2 | One drop of 2% w/w Phentolamine Mesylate Ophthalmic Solution in each eye daily before bedtime for 28 days from Day 1 to Day 28. |
| 3 | One drop of Placebo Ophthalmic Solution in each eye daily before bedtime for 28 days from Day 1 to Day 28. |

TABLE 2

Study Medication

| Study Medication | Composition of Study Medication |
|---|---|
| 1% w/w Phentolamine Mesylate Ophthalmic Solution | 1% w/w phentolamine mesylate<br>4% w/w mannitol<br>3 mM sodium acetate<br>water<br>pH in the range 4.8 to 5.0 |
| 2% w/w Phentolamine Mesylate Ophthalmic Solution | 2% w/w phentolamine mesylate<br>4% w/w mannitol<br>3 mM sodium acetate<br>water<br>pH in the range 4.8 to 5.0 |
| Placebo Ophthalmic Solution | 4% w/w mannitol<br>3 mM sodium acetate<br>water<br>pH in the range 4.8 to 5.0 |

Evaluation of human subjects during the study will include measurement of intraocular pressure, eye redness, heart rate, blood pressure, and any adverse events. The primary efficacy endpoint is reduction in intraocular pressure in the patient's eye measured at day 28 of the study relative to placebo control.

During the study, human subjects are prohibited for taking any additional agent that is a systemic alpha adrenergic antagonists; all eye drops other than study medication are prohibited during the 28 days of dosing. Target enrollment is to enroll at least 40 patients, which will be divided approximately equally among the two or more Treatment Groups.

Example 4—Reduction in Intraocular Pressure by Phentolamine Mesylate in Human Subjects with Bilateral Open-Angle Glaucoma or Ocular Hypertension Ability of phentolamine mesylate to reduce intraocular pressure in the eye of a human subject with bilateral open-angle glaucoma or ocular hypertension may be evaluated according to a clinical study in which an aqueous ophthalmic solution containing phentolamine mesylate is administered to the eye of a patient, and then the patient is evaluated for reduction in intraocular pressure (IOP) in the eye that received the aqueous ophthalmic solution containing phentolamine mesylate. Experimental procedures and results are described below.

Part I—Experimental Procedures

Human subjects are screened for potential enrollment and, if qualified, enrolled in the study. Inclusion criteria and exclusion criteria for the study are set forth below.

Inclusion Criteria
  Have a diagnosis of open-angle glaucoma or ocular hypertension in both eyes.
  IOP after washout from prior IOP-lowering medications, if applicable, is required to be >20 mmHg at 08:00 hours and >17 mmHg at 10:00 and 16:00 hours.
  IOP has to be <27 mmHg in both eyes at all qualification time points.
Exclusion Criteria
  Patient's Open-angle glaucoma or ocular hypertension has a pseudoexfoliation or pigment dispersion component.
  Patient has a history of angle closure or narrow angles, or has previous glaucoma intraocular surgery or glaucoma laser procedures in either eye.
  Has a known hypersensitivity or contraindication to alpha-adrenoceptor antagonists.

For human subjects enrolled in the study, the human subject is assigned to a Treatment Group in random order. There will be two Treatment Groups, as set forth in Table 1 below. Human subjects shall receive study medication as set forth in Table 1 according to the Treatment Group to which the subject is assigned. Study medication is listed in Table 2. A period of thirty days is required for washout periods for ocular hypotensive medications prior to study initiation. Evaluations of human subjects may be performed at Screening, Qualification #1, Day 1/Qualifying #2, Day 15, Day 43, and Day 90. For visits at Day 1, Day 15, Day 43, and Day 90, subjects may be evaluated at 08:00, 10:00, and 16:00 hours within the visit day.

TABLE 1

Treatment Groups

| Treatment Group | Study Medication and Administration Protocol |
|---|---|
| 1 | One drop of 1% w/w Phentolamine Mesylate Ophthalmic Solution in each eye daily before bedtime for 90 days from Day 1 to Day 90.<br>To maintain masking for the study, patients will also place one drop of Placebo Ophthalmic Solution in each eye daily in the morning for 90 days from Day 1 to Day 90. |
| 2 | One drop of 0.5% w/w Timolol Maleate Ophthalmic Solution in each eye twice daily (once in the morning and once in the evening before bedtime) for 90 days from Day 1 to Day 90. |

TABLE 2

Study Medication

| Study Medication | Composition of Study Medication |
|---|---|
| 1% w/w Phentolamine Mesylate Ophthalmic Solution | 1% w/w phentolamine mesylate<br>4% w/w mannitol<br>3 mM sodium acetate<br>water<br>pH in the range 4.8 to 5.0 |
| 0.5% w/w Timolol Maleate Ophthalmic Solution | 0.5% w/w timolol maleate<br>benzalkonium chloride<br>monobasic and dibasic sodium phosphate,<br>water<br>pH of approximately 7.0<br>osmolarity in the range of about 274 to 328 mOs |
| Placebo Ophthalmic Solution | 4% w/w mannitol<br>3 mM sodium acetate<br>water<br>pH in the range 4.8 to 5.0 |

Evaluation of human subjects during the study may include measurement of intraocular pressure, eye redness, heart rate, blood pressure, and any adverse events. The primary efficacy endpoint is mean IOP at one or more of the following time points: 08:00, 10:00, and 16:00 hours at Week 2 (Day 15), Week 6 (Day 43), and Month 3 (Day 90).

During the study, human subjects are prohibited for taking any additional agent that is a systemic alpha adrenergic antagonist; all eye drops other than study medication are prohibited during the 90 days of dosing. Target enrollment is to enroll at least 200 patients, which will be divided approximately equally among the Treatment Groups.

Example 5—Reduction in Intraocular Pressure by Phentolamine Mesylate in Human Subjects with Open-Angle Glaucoma or Ocular Hypertension Ability of phentolamine mesylate to reduce intraocular pressure in the eye of human subjects with bilateral open-angle glaucoma (OAG) or ocular hypertension (OHT) was evaluated according to a clinical study in which an aqueous ophthalmic solution containing phentolamine mesylate was administered to the eye of a patient, and then the patient was evaluated for reduction in intraocular pressure in the eye that received the aqueous ophthalmic solution containing phentolamine mesylate. Approximately 40 subjects with either OAG or OHT were randomized, for a target of 36 completed subjects. Subjects were randomized in a 1:1 ratio to receive 1% w/w Phentolamine Mesylate Ophthalmic Solution or placebo once daily for 14 days beginning at 8 PM to 10 PM on Day 1 and continuing through Day 14. Efficacy evaluations of intraocular pressure (IOP) took place at the Baseline and the Treatment-study Visit days (Day 8±1 Day and Day 15±1 Day) at 8 AM, 10 AM, and 4 PM. All IOP measurements had a window of +15 minutes with at least 2 hours between the 8 AM and 10 AM assessments. There were Follow-up Visits on Day 16 at 8 AM±15 minutes and by phone on Day 22 (7 days after the last Treatment-study Visit). Further experimental procedures and results are described below.

Part I—Experimental Procedures

The total length of subject participation was approximately 7 to 8 weeks with six clinic visits and one telephone call follow up, as summarized below:
  Screening Visit (1 day).
  Washout Visit/period (as necessary) (4-5 weeks with safety check visit at 2 weeks).
  Qualification/Baseline Visit (1 day).
  Treatment-study Visit Day 8 (1 week).
  Treatment-study Visit Day 15 (1 week).
  Follow-up clinic Visit on Day 16 (1 day).
  Follow-up telephone call at Day 22 (1 week).

Human subjects were screened for potential enrollment and, if qualified, enrolled in the study. Inclusion criteria and exclusion criteria for the study are set forth below. Human subjects could qualify in either eye. The eye with the higher intraocular pressure (IOP) at the Qualification Visit at 8 AM was designated as the study eye for the primary endpoint efficacy analysis. In the case where both eyes had the same IOP, the study eye was the right eye.

Inclusion Criteria
  18 years of age or greater.
  Diagnosis of OAG or OHT. The diagnosis of OHT must have been in both eyes. For OAG, the diagnosis could have been in either eye with OHT in the fellow eye. A reported history of untreated OHT with IOP≥22 mmHg and ≤30 mmHg was preferred.
  Untreated or treated OAG/OHT with 2 or fewer ocular hypotensive medications.
  Untreated (post-washout) mean IOP≥22 mmHg and ≤30 mmHg in the study eye at the Qualification Visit (8 AM).
  Corrected visual acuity in each eye+1.0 logMAR or better by Early Treatment Diabetic Retinopathy Study (ETDRS) in each eye (equivalent to 20/200 or better) at the Screening Visit and Qualification Visit.
  Otherwise healthy and well-controlled subjects.
  Able and willing to give signed informed consent and follow study instructions.
  Able to self-administer study medication or to have study medication administered by a caregiver throughout the study period.

Exclusion Criteria
  Closed or very narrow angles (Grade 0-1, Shaffer) or angles that the investigator judges as occludable and/or with evidence of peripheral anterior synechiae (PAS) ≥180 degrees by gonioscopy within 6 months prior to Screening Visit in either eye.
  Glaucoma: pseudo-exfoliation or pigment dispersion component, history of angle closure or narrow angles. Note: Previous laser peripheral iridotomy was not allowed.
  Known hypersensitivity to any α-adrenoceptor antagonists.
  Previous laser and/or non-laser glaucoma surgery or procedure in either eye.
  Refractive surgery in either eye (e.g., radial keratotomy, photorefractive keratectomy (PRK), laser-assisted in situ keratomileusis (LASIK), or corneal cross linking).
  Ocular trauma in either eye within the 6 months prior to Screening, or ocular surgery or non-refractive laser treatment within the 3 months prior to Screening.
  Recent or current evidence of ocular infection or inflammation in either eye. Current evidence of clinically significant blepharitis, conjunctivitis, or a history of herpes simplex or herpes zoster keratitis at Screening in either eye.
  Ocular medication in either eye of any kind within 30 days of Screening, with the exception of a) ocular hypotensive medications (which had to be washed out), b) lid scrubs (which could be used prior to Screening but could not be used after Screening) or c) lubricating drops for dry eye (preservative-free artificial tears), which could be used throughout the study.
  Clinically significant ocular disease in either eye as deemed by the investigator (e.g., corneal edema, uveitis, or severe keratoconjunctivitis sicca) that might interfere with the study, including glaucomatous damage so severe that washout of ocular hypotensive medications for 1 month was not judged safe (i.e., cup-to-disc ratio >0.8, severe visual field defect).
  History of diabetic retinopathy.
  Contact lens wear within 3 days prior to and for the duration of the study.
  Central corneal thickness in either eye >600 μm at Screening.
  Any abnormality in either eye preventing reliable applanation tonometry (e.g., central corneal scarring).
  Known hypersensitivity or contraindication to α- and/or β-adrenoceptor antagonists (e.g., chronic obstructive pulmonary disease or bronchial asthma; abnormally low blood pressure or heart rate; second or third degree heart block or congestive heart failure; or severe diabetes).
  Clinically significant systemic disease (e.g., uncontrolled diabetes, myasthenia gravis, cancer, hepatic, renal, endocrine or cardiovascular disorders) that might interfere with the study.
  Participation in any investigational study within 30 days prior to Screening.
  Use of any topical or systemic adrenergic or cholinergic drugs up to 30 days prior to Screening, or during the study unless the drug, dose and regimen had been consistent for the 30 days prior to Screening.

Changes in systemic medication that could have an effect on IOP within 30 days prior to Screening or anticipated during the study.

Women of childbearing potential who were pregnant, nursing, planning a pregnancy, or not using a medically acceptable form of birth control. An adult woman was considered to be of childbearing potential unless she was 1 year postmenopausal or 3 months post-surgical sterilization. All females of childbearing potential must have had a negative urine pregnancy test result at the Screening and Qualification examinations and must have intended to not become pregnant during the study.

Resting heart rate (HR) outside the normal range (50-110 beats per minute) at the Screening or Qualification Visit. HR could be repeated only once if outside the normal range, following at least a 5 minute rest period in the sitting position.

Hypertension with resting diastolic blood pressure (BP) >105 mmHg or systolic BP>160 mmHg at the Screening or Qualification Visit. BP could be repeated only once if outside the specified range, following at least a 5 minute rest period in the sitting position.

Subjects with an ophthalmic history of increased IOP (≥22 mmHg and ≤30 mmHg) were selected for study participation and were screened for study eligibility.

After Screening, eligible subjects, if being treated at the time with glaucoma medications, were required to washout and refrain from administration of any glaucoma drugs for at least 28 days and no more than 35 days prior to the Qualification Visit. The washout subjects were brought back at approximately two weeks after starting the washout period for an IOP safety check. In the judgement of the investigator, if there was any risk to the eye(s) of the subject, or if the mean IOP in either eye during washout was >30 mmHg, then an appropriate rescue or prior medication was administered, and the subject was considered a screen failure. Adverse events occurring during the washout period were also assessed at this visit. After the washout, where applicable, a Qualification Visit occurred before dosing on Day 1.

Subjects not previously treated with any glaucoma drugs did not require a washout period and could return the following day, or up to 35 days later, for their Qualification/Baseline Visit.

At the Qualification Visit, IOP eligibility was determined with a Goldmann tonometer using the two-person method (one person physically applies the tonometer, while another reads the result) at 8 AM, 10 AM, and 4 PM (mean IOP at 8 AM must be ≥22 mmHg and ≤30 mmHg, and ≥19 mmHg at 10 AM and 4 PM). IOP was measured twice in both eyes at each timepoint and the mean value was used in eligibility assessments. All IOP measurements had a window of ±15 minutes with at least 2 hours between the 8 AM and 10 AM assessments.

The eye with the higher IOP at the Qualification Visit at 8 AM was designated as the study eye for the primary endpoint efficacy analysis. In the case where both eyes had the same IOP, the study eye was the right eye. All treatments were administered to both eyes (OU).

At the Qualification/Baseline Visit:
Females of childbearing potential took a urine pregnancy test at 8 AM.
Review of concomitant medications was conducted at 8 AM.
IOP measurements using a Goldmann Applanation tonometer at the Baseline visit and both Treatment-study visits were performed at 8 AM, 10 AM and 4 PM.

All IOP measurements had a window of ±15 minutes with at least 2 hours between the 8 AM and 10 AM assessments. IOP was measured twice in both eyes at each timepoint. The mean value at each timepoint for the study eye was used in efficacy assessments. If the difference in the two IOP measurements was >5 mmHg, a third measurement was obtained, and the three values were averaged.

Pupil diameter, using a Neuroptics pupillometer, near visual acuity using a standard chart held at 14 inches, and distance visual acuity with ETDRS were measured at 8 AM.

Resting HR and BP were measured at 8 AM and 4 PM. Blood pressure, using the same arm, same cuff size appropriate for arm circumference throughout the study, and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Eye redness (conjunctival hyperemia) was visually checked at 8 AM, 10 AM and 4 PM using the CCLRU bulbar redness scale.

Adverse events were reviewed at each timepoint.

If the subject met all of the inclusion criteria and none of the exclusion criteria, including all three timepoint IOP measurements, this qualification visit became the Baseline Visit, a subject number was assigned, and he/she was randomized into the study. The first dose of study medication was taken at 8 PM to 10 PM on the Baseline Visit (Day 1).

Site personnel demonstrated the proper instillation technique to the subject at the Qualification/Baseline Visit (Day 1) and the subject self-administered a dose of artificial tears at the study site, instilling 1 drop in each eye from the unit-dose bottle (Note: If a drop was not instilled into the eye, the subject was instructed to wait approximately 10-15 seconds and administer a second drop). The subject received the following instructions regarding proper instillation technique:

The subject should be in a seated position and should tilt his or her head backward for administration of the study medication. The bottle of study medication should be held at an almost vertical position above the eye while the lower eyelid is pulled down gently, and 1 drop is placed into the conjunctival cul-de-sac. The tip of the bottle should not touch the eye. After a drop is instilled in each eye, the subject should keep the eyes gently closed for approximately 30 seconds. After successful instillation of the drop in each eye, the subject should carefully empty any remaining contents as directed.

The subject was given their study medication dropper bottles, instructions when to administer the eye drop (8 PM to 10 PM), and when to return to the clinic.

The subject was instructed to administer one drop to each eye from a new single unit-dose bottle, each evening of dosing, and close the eyes gently for 30 seconds, then empty the remaining bottle contents (and store the opened bottle in the baggie provided and place it in the medication box for return to the study site at the Day 8 Visit). The subject was instructed to follow the same procedures each subsequent evening of dosing (approximately 24 hours between doses). At the Day 8 visit, the medication box, complete with opened bottles and any unopened study medication was to be returned to the study site where the baggies of opened medication were removed, and the study medication box was re-dispensed with the unopened medication. During the second week of treatment, subjects were instructed to continue to administer one drop of study medication to each eye every night using a new bottle for each dose, then emptying the remaining contents of that bottle (and storing the opened bottles in the baggies and placing them back in the box to return to the study site at the Day 15 Visit). The Day 15 visit was the last day of study treatment; no further study medication was dispensed at that visit.

The subject was instructed to contact the investigator should adverse events of concern occur (e.g., shortness of breath, fainting, etc.), or to go to the emergency room if the event was life-threatening.

Treatment-study visits occurred twice—on Day 8±1 Day and Day 15±1 Day. IOP evaluations were performed at 8 AM, 10 AM and 4 PM on each of these days. On Study Day 8, the following was performed:

Review of concomitant medications was conducted at 8 AM.

IOP measurements were performed at 8 AM, 10 AM and 4 PM. All IOP measurements had a window of ±15 minutes with at least 2 hours between the 8 AM and 10 AM assessments. IOP was measured twice in both eyes at each timepoint. The mean value at each timepoint for the study eye was used in efficacy assessments. If the difference in the two IOP measurements was >5 mmHg, a third measurement was obtained, and the three values were averaged.

Pupil diameter, near and distance visual acuity, resting HR and BP were measured at 8 AM and 4 PM. Blood pressure, using the same arm, same cuff size appropriate for arm circumference throughout the study, and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Eye redness (conjunctival hyperemia) was visually checked at each timepoint using the CCLRU bulbar redness scale.

On Study Day 15, the following was performed:

Subjects were to bring their used dropper bottles and any unused medications with them for purposes of drug accountability.

Subjects were asked if they had any problems with their eyes from the last visit, and if there have been any changes in their medical condition, or concomitant medications, since their last visit. Any changes in the condition of the subject were recorded as an adverse event.

Females of childbearing potential took a urine pregnancy test at 8 AM.

Review of concomitant medications was conducted at 8 AM.

IOP measurements were performed at 8 AM, 10 AM and 4 PM. All IOP measurements had a window of ±15 minutes with at least 2 hours between the 8 AM and 10 AM assessments. IOP was measured twice in both eyes at each timepoint. The mean value at each time point for the study eye was used in efficacy assessments. If the difference in the two IOP measurements was >5 mmHg, a third measurement was obtained, and the three values were averaged.

Pupil diameter, near and distance visual acuity distance visual acuity, resting HR and BP were measured at 8 AM. Blood pressure, using the same arm, same cuff size appropriate for arm circumference throughout the study, and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Eye redness (conjunctival hyperemia) was visually checked at each time point using the CCLRU bulbar redness scale.

Adverse events were reviewed at each time point.

Distance and near visual acuity, pupil diameter, and a complete ophthalmic examination, including biomicroscopy were also performed at 4 PM.

Subjects completing their Day 15 Visit were instructed not to resume their original glaucoma medication(s) until after completion of the Day 22 Follow-up phone call.

A Follow-up Visit occurred at 8 AM±15 minutes on Day 16. Assessments performed at this visit included an IOP measurement at 8 AM±15 minutes, visual acuity, pupil diameter, and safety measures. More specifically, the following were performed:

Subjects were asked if they had any problems with their eyes from the last visit, and if there have been any changes in their medical condition, or concomitant medications, since their last visit. Any changes in the condition of the subject were recorded as an adverse event.

Review of concomitant medications was conducted at 8 AM.

IOP was measured twice in the study eye at 8 AM±15 minutes, and the two values were averaged. If the difference in the two IOP measurements was >5 mmHg, a third measurement was obtained, and the three values were averaged.

Pupil diameter, near and distance visual acuity distance visual acuity, resting HR and BP were measured at 8 AM. Blood pressure, using the same arm, same cuff size appropriate for arm circumference throughout the study, and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Eye redness (conjunctival hyperemia) was visually checked at each timepoint using the CCLRU bulbar redness scale.

Adverse events were reviewed at 8 AM.

Subjects completing their Day 16 Visit were reminded not to resume their original glaucoma medication(s) until after completion of the Day 22 Follow-up phone call.

A Follow-up Visit phone call occurred on Day 22, seven days after the last dose. Any concomitant medications, subject-reported conjunctiva redness and adverse events (AEs) were collected.

Visits on Day 8 and 15 were allowed to be 1 day early or late. If the visit was late, the subject was advised to take an additional dose from one of the 2 spare dropper bottles provided in the study medication box the night before the visit. The subject was instructed to then empty the remaining contents and store the opened bottle in the baggie provided and place it in the medication box for return to the study site at their next visit. If the Day 15 Visit occurred one day early or late, the Day 16 Visit and the Day 22 telephone call were adjusted accordingly.

Any subject was permitted to voluntarily withdraw from the study at any time without prejudice. A non-completing subject was defined as one who exited the study by their own volition or at the discretion of the Investigator and/or the Medical Monitor prior to completing all of the study procedures required in the protocol.

Study subjects received study medication as set forth in Table 1 according to the Treatment Group to which the subject was assigned. Study medication is listed in Table 2.

TABLE 1

Treatment Groups

| Treatment Group | Study Medication and Administration Protocol |
|---|---|
| 1 | One drop of 1% w/w Phentolamine Mesylate Ophthalmic Solution in each eye daily at 8 PM to 10 PM for 14 days, from Day 1 through Day 14 for subjects randomized to active treatment. |
| 2 | One drop of Placebo Ophthalmic Solution in each eye daily at 8 PM to 10 PM for 14 days, from Day 1 through Day 14 for subjects randomized to placebo. |

TABLE 2

Study Medication

| Study Medication | Composition of Study Medication |
|---|---|
| 1% w/w Phentolamine Mesylate Ophthalmic Solution | 1% w/w phentolamine mesylate<br>4% w/w mannitol<br>3 mM buffer comprising sodium acetate and acetic acid<br>water<br>pH in the range 4.8 to 5.0 |
| Placebo Ophthalmic Solution | 4% w/w mannitol<br>3 mM buffer comprising sodium acetate and acetic acid<br>water<br>pH in the range 4.8 to 5.0 |

Evaluation of Efficacy and Safety—Endpoints and Measurement Procedures

Evaluation of human subjects during the study included measurement of intraocular pressure, eye redness, heart rate, blood pressure, and any adverse events. The primary efficacy endpoint was the change from Baseline to Day 15 in mean diurnal IOP in the study eye. Mean diurnal IOP was the mean of the IOP measurements at all three timepoints (8 AM, 10 AM, 4 PM). IOP measurements at the Baseline Visit and both Treatment-study Visits were performed at 8 AM, 10 AM and 4 PM. All IOP measurements had a window of +15 minutes with at least 2 hours between the 8 AM and 10 AM assessments. IOP was measured twice in both eyes at each timepoint. The mean value at each timepoint for the study eye was used in efficacy assessments. If the difference in the two IOP measurements was >5 mmHg, a third measurement was obtained, and the three values were averaged.

Secondary efficacy endpoints were analyzed by study eye, fellow eye, and all eyes (unless otherwise indicated) and included:

Change from Baseline to Day 15 in mean diurnal IOP in the fellow eye and all eyes.

Change from Baseline to Day 8 in mean diurnal IOP.

Mean IOP at each post-treatment timepoint (8 AM, 10 AM and 4 PM; on Day 8 and Day 15).

Change and percent change from Baseline to Day 8 and Day 15 in IOP at each timepoint (8 AM, 10 AM, 4 PM), and Day 16 at 8 AM.

Percentage of subjects achieving reductions from Baseline to Day 8 and Day 15 in IOP at 8 AM of greater than or equal to 10%, 15%, 20%, 25% and 30%.

Percentage of subjects achieving Day 8, Day 15 and Day 16 IOP levels at 8 AM of less than or equal to 16 mmHg, 18 mmHg, 20 mmHg and 22 mmHg.

Change and percent change from Baseline Day 8, Day 15, and Day 16 in IOP at 8 AM.

Change and percent change to Days 8, 15, and 16 in pupil diameter at 8 AM.

Percentage of subjects achieving reductions from Baseline to Day 8, Day 15 and Day 16 in pupil diameter at 8 AM of greater than or equal to 10%, 15%, 20%, 25%, and 30%.

Change and percent change from Baseline to Day 8, Day 15, and Day 16 in best corrected distance visual acuity (BCDVA) (ETDRS high contrast) (photopic and mesopic) at 8 AM.

Change and percent change from Baseline to Day 8, Day 15, and Day 16 in distance corrected near visual acuity (DCNVA) (ETDRS high contrast) (photopic and mesopic) at 8 AM.

Percentage of subjects achieving improvements from Baseline to Day 8, Day 15, and Day 16 in BCDVA and DCNVA (photopic and mesopic) of greater than or equal to 1 line, 2 lines and 3 lines.

All Secondary Endpoints related to IOP were analyzed additionally in those subpopulations with Baseline IOP of <25 mmHg and ≥25 mmHg.

For each subject at each timepoint (8 AM, 10 AM, 4 PM), the OP value was the average OP (from the 2 measurements taken at that timepoint) in the study eye or in the fellow eye. The lighting conditions were kept the same from visit to visit. Every effort was made to have the same clinician perform the IOP measurements at all timepoints and at all visits.

The standard procedure for measuring efficacy endpoints at the Screening Visit, the Qualification/Baseline Visit, the Treatment-study visits, and Follow-up Visit utilized the equipment and procedures set forth in Table 3, below.

TABLE 3

Procedures for Measuring Efficacy Endpoints

| Efficacy Endpoint | Equipment Name | Measurement (Unit) | Procedure |
|---|---|---|---|
| IOP | Goldmann Applanation Tonometer | mmHg | Used a two-person method (one-person physically applied the tonometer, while another read the result). |

TABLE 3-continued

Procedures for Measuring Efficacy Endpoints

| Efficacy Endpoint | Equipment Name | Measurement (Unit) | Procedure |
|---|---|---|---|
| | | | Each site was required to have the appropriate SOP for the Tonometer and the tip for a) calibrating the tonometer regularly and b) preventing transmission of disease. Either a Goldmann Prism or Tonosafe Prism tip was used. The same machine and room was used each time for this measurement. |
| Distance Visual Acuity | Standard ETDRS chart | Letters and/or LogMAR | In photopic and mesopic conditions. High Contrast. Best Corrected. Chart 4 m away (on wall or screen). Monocular and binocular measurements. |
| Near Visual Acuity | Standard reading card (Rosenbaum pocket vision screener) | Jaeger and/or LogMAR | In photopic and mesopic conditions. High Contrast. Best Corrected. Held the card 14 inches away. Monocular and binocular measurements. |
| Pupil diameter | Neuroptics Pupillometer | mm | In photopic and mesopic conditions. Held pupillometer close to eye and when circle in the screen is centered on the pupil, the measurement was taken; the output was recorded on case report form. |

For this study photopic and mesopic light conditions were considered to be "with the lights on or with the lights off". There were no specific light conditions required other than that the same light conditions were to be used throughout the study.

The primary safety measures were objective biomicroscopic and ophthalmoscopic examination, subjective ocular tolerability, and AEs. Other safety measures were systemic safety as measured by heart rate and blood pressure. Urine pregnancy tests for females of childbearing potential were conducted. Conjunctival hyperemia was measured with a CCLRU card 4-point scale:

Mild (+1)=Normal Appeared white with a small number of conjunctival blood vessel easily observed.
Mild (+1)=Prominent, pinkish-red color of both the bulbar and palpebral conjunctiva.
Moderate (+2)=Bright, scarlet red color of the bulbar and palpebral conjunctiva.
Severe (+3)=Beefy red with petechiae, dark red bulbar and palpebral conjunctiva with evidence of subconjunctival hemorrhage.

Biomicroscopy of anterior segment was performed, including evaluation of cornea, conjunctiva and anterior chamber. Fluorescein staining was used. For ophthalmoscopy, a dilated fundus exam was performed including examination of the optic nerve, macula, vessels and periphery. Blood pressure was measured using the same arm and same cuff size appropriate for arm circumference throughout the study. Blood pressure and heart rate were measured after at least 3 minutes rest in the sitting position. If HR or BP were outside the normal range (HR<50 or >110 beats per minute, resting diastolic blood pressure (BP)>105 mmHg or systolic BP>160 mmHg), they could be repeated only once following at least a 5 minute rest period in the sitting position.

Evaluation of Efficacy Analysis Procedures

Efficacy was assessed using the full analysis set (FAS) with subjects included in the treatment group they were randomized to, regardless of the treatment they actually received. For the analysis of the primary efficacy endpoint, observed case data was used (no imputation was performed for missing efficacy data) for the primary analysis. Confirmatory analyses were performed using the all randomized (AR) population, with imputation performed for missing data. For the analysis of the secondary efficacy endpoints, only observed case data was used. If warranted, confirmatory analyses using the AR population with imputation for missing data were also performed for the secondary efficacy endpoints.

For all efficacy endpoints, Baseline was defined as the pre-dose value from the Baseline Visit/Day 1. If there was no pre-dose value from Day 1, then Baseline was the value from the Screening Visit.

IOP was measured twice in both eyes at each timepoint. The mean value at each timepoint for the study eye was used in efficacy assessments. If the difference in the two IOP measurements was >5 mmHg, a third measurement was obtained, and the three values were averaged. The lighting conditions were kept the same from visit to visit.

Diurnal IOP was the mean of all three measurements (8 AM, 10 AM, and 4 PM) on a specific day.

All efficacy data was summarized by treatment group, study day and timepoint (8 AM, 10 AM, 4 PM), as appropriate.

The primary efficacy endpoint was the change from Baseline to Day 15 in mean diurnal IOP. The primary efficacy endpoint was analyzed using analysis of covariance (ANCOVA) with change from Baseline to Day 15 in diurnal IOP as the dependent variable; treatment as a factor; and Baseline diurnal IOP as the covariate. The ANCOVA was performed using the FAS, with subjects included in their randomized treatment group regardless of the treatment they actually received. Observed case data only was used; that is, any missing Day 15 diurnal IOP was not imputed. The least-squares mean (LSM) and standard error (SE) were determined for both treatment groups, along with the placebo-corrected LSM, its 95% confidence interval (CI) and associated p-value. A confirmatory analysis of the primary efficacy endpoint was performed, using the AR population with missing Day 15 values imputed.

For each of the continuous secondary efficacy endpoints, the same ANCOVA for the primary efficacy endpoint was used, with the respective Baseline included as the covariate. Each ANCOVA was performed using the FAS with subjects included in their randomized treatment group regardless of the treatment they actually received. Only observed case data was used; that is, missing values for post-randomization visits were not imputed. The output from each ANCOVA included the LSM and SE for both treatment groups, along with the placebo-corrected LSM, its 95% CI and associated p-value.

For each of the secondary efficacy endpoints related to percentage of subjects (or percentage of eyes) meeting certain criteria, the analysis was performed using a logistic regression with treatment and Baseline included as independent factors. For each analysis, the percentage of subjects (or eyes) in each treatment group meeting the criteria, the odds ratio (OR) with 95% CI and p-value was determined. For all of these endpoints, the FAS was used with subjects included in their randomized treatment group regardless of the treatment they actually received.

Evaluation of Safety—Analysis Procedures

Safety was assessed using the safety population (SP) with subjects included in the treatment group they actually received, regardless of their randomized treatment. Observed case data was used; no imputation was performed for missing safety data.

For all safety endpoints, Baseline was defined as the pre-dose value from the Baseline Visit/Day. If there was no pre-dose value from Day 1, then Baseline was the value from the Screening Visit.

Biomicroscopy results and ophthalmoscopy results were summarized by treatment group using the SP. As both eyes were treated in the study; both eyes were included in the summarizations for visual acuity, biomicroscopy, and ophthalmoscopy. Separate summary tables were created for the study eye versus the fellow eye.

Heart rate and blood pressure values and change from Baseline in the values were summarized by treatment group and time point (8 AM on Day 8, Day 15 and Day 16; 4 PM on Day 15).

Verbatim descriptions of AEs were coded using MedDRA. Only treatment-emergent AEs (TEAEs; those that occur after the first dose of study medication or increase in severity after initiation of study medication) were summarized. TEAEs and serious AEs (SAEs) were summarized by treatment group, by system organ class (SOC), severity, and relationship to study medication.

Part II—Results

The observed reduction in IOP for categories of human subjects is provided in Tables 4A and 4B. Results in Table 4A are from human subjects that received 1% w/w Phentolamine Mesylate Ophthalmic Solution. Results in Table 4B are from human subjects that placebo.

As shown in Table 4A, the reduction in IOP in human subjects receiving 1% w/w Phentolamine Mesylate Ophthalmic Solution was greater in human subjects having a lower baseline IOP (e.g., IOP<23 mmHg) compared to reduction in IOP observed in the category of human subjects having a higher baseline IOP (e.g., the Category A Patients, which have IOP<26 mmHg).

For human subjects enrolled in this study having a baseline IOP≥26 mmHg and receiving 1% w/w Phentolamine Mesylate Ophthalmic Solution according to the dosing protocol, the observed change in IOP at Day 15 relative to Baseline was similar to that observed in the placebo group.

TABLE 4A

Observed Change in IOP for Human Subjects Having a Baseline IOP <26 mmHg

| | Patients* | | | 1% w/w Phentolamine Mesylate Ophthalmic Solution | | |
|---|---|---|---|---|---|---|
| Patient Category | IOP Baseline (mmHg)** | n (number of eyes) | Average Baseline Diurnal IOP (mmHg) | Average Change in IOP from Baseline at Day 15 (mmHg) | Min | Max |
| A | <26 | 25 | 22.56 | −1.83 | −7.7 | 4.3 |
| B | <25 | 18 | 22.09 | −1.85 | −7.7 | 4.3 |
| C | <24 | 12 | 21.58 | −2.52 | −7.3 | 3.7 |
| D | <23 | 5 | 20.6 | −3.10 | −7.3 | −0.3 |

*Per protocol.
**Subjects that achieved IOP baseline at all time points (8 am, 10 am, 4 pm) on Baseline Day 1.

TABLE 4B

Observed Change in IOP for Human Subjects Having a Baseline IOP <26 mmHg

| | Patients* | | | Placebo | | | |
|---|---|---|---|---|---|---|---|
| Patient Category | IOP Baseline (mmHg)** | n (number of eyes) | Average Baseline Diurnal IOP (mmHg) | Average Change in IOP from Baseline at Day 15 (mmHg) | Min | Max | p value |
| A | <26 | 20 | 22.59 | −1.69 | −4.3 | 3.3 | 0.8663 |
| B | <25 | 14 | 22.02 | −1.29 | −4.3 | 3.3 | 0.6082 |
| C | <24 | 6 | 21.19 | −0.35 | −3.7 | 3.3 | 0.1629 |
| D | <23 | 1 | 18 | 3.30 | 3.3 | 3.3 | n/a |

*Per protocol.
**Subjects that achieved IOP baseline at all time points (8 am, 10 am, 4 pm) on Baseline Day 1.

The observed change in pupil diameter under phototopic conditions at day 15 in the human subjects is listed in Tables 5A and 5B. The observed change in pupil diameter under phototopic conditions at day 16 in the human subjects is listed in Tables 6A and 6B. The observed change in pupil diameter under mesopic conditions at day 15 in the human subjects is listed in Table 7A. The observed change in pupil diameter under mesopic conditions at day 16 in the human subjects is listed in Table 7B.

TABLE 5A

Observed Change in Pupil Diameter Under Photopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Photopic Day 15, 8 AM | | | | |
| n | 38 | 40 | | |
| Mean (SD) | 2.84 (0.485) | 3.54 (0.809) | | |
| Median | 2.77 | 3.45 | | |
| Min, Max | 2.2, 4.4 | 2.5, 6.0 | | |
| Day 15, 8 AM Change from Baseline | | | | |
| n | 38 | 40 | | |
| Mean (SD) | −0.72 (0.578) | −0.08 (0.544) | | |
| Median | −0.64 | −0.12 | | |
| Min, Max | −2.0, 0.5 | −1.2, 1.4 | | |
| Day 15, 8 AM Change from Baseline ANCOVA [1] | | | −0.66 (−0.87, −0.45) | <0.0001 |
| Least-squares mean (SE) | −0.73 (0.076) | −0.07 (0.074) | | |
| p-value [2] | <0.0001 | 0.3515 | | |

TABLE 5B

Observed Change in Pupil Diameter Under Photopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Photopic Day 15, 8 AM Percent Change | | | | |

TABLE 5B-continued

Observed Change in Pupil Diameter Under Photopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| from Baseline | | | | |
| n | 38 | 40 | | |
| Mean (SD) | −18.79 (13.168) | −0.56 (17.645) | | |
| Median | −19.55 | −3.93 | | |
| Min, Max | −40.4, 17.9 | −25.9, 70.1 | | |
| Day 15, 8 AM Percent Change from Baseline ANCOVA [1] | | | −18.90 (−25.20, −12.60) | <0.0001 |
| Least-squares mean (SE) | −19.13 (2.262) | −0.23 (2.205) | | |
| p-value [2] | <0.0001 | 0.9157 | | |
| Day 16, 8 AM | | | | |
| n | 38 | 40 | | |
| Mean (SD) | 2.85 (0.497) | 3.70 (0.865) | | |
| Median | 2.84 | 3.49 | | |
| Min, Max | 2.0, 4.3 | 2.4, 6.5 | | |

Min = Minimum, Max = Maximum, SD = Standard deviation, LS = Least-squares, CI = Confidence interval, SE = Standard error

[1] For an analysis of covariance (ANCOVA) with (percent) change from Baseline in Pupil Diameter as the dependent variable; treatment as a factor; and Baseline Pupil Diameter as the covariate.

[2] From a test comparing the individual treatment change from baseline LS mean to zero.

[3] The pooled data from the Study Eye and Fellow Eye.

TABLE 6A

Observed Change in Pupil Diameter Under Photopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Photopic Day 16, 8 AM Change from Baseline | | | | |
| n | 38 | 40 | | |
| Mean (SD) | −0.70 (0.532) | 0.08 (0.537) | | |
| Median | −0.55 | 0.01 | | |
| Min, Max | −1.9, 0.3 | −1.2, 1.4 | | |
| Day 16, 8 AM Change from Baseline ANCOVA [1] | | | −0.80 (−1.01, −0.58) | <0.0001 |
| Least-squares mean (SE) | −0.71 (0.076) | 0.09 (0.074) | | |
| p-value [2] | <0.0001 | 0.2421 | | |
| Day 16, 8 AM Percent Change from Baseline | | | | |
| n | 38 | 40 | | |
| Mean (SD) | −18.47 (12.457) | 3.71 (18.135) | | |
| Median | −17.13 | 0.12 | | |
| Min, Max | −38.8, 12.1 | −26.1, 66.7 | | |

Min = Minimum, Max = Maximum, SD = Standard deviation, LS = Least-squares, CI = Confidence interval, SE = Standard error
[1] For an analysis of covariance (ANCOVA) with (percent) change from Baseline in Pupil Diameter as the dependent variable; treatment as a factor; and Baseline Pupil Diameter as the covariate.
[2] From a test comparing the individual treatment change from baseline LS mean to zero.
[3] The pooled data from the Study Eye and Fellow Eye.

TABLE 6B

Observed Change in Pupil Diameter Under Photopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Photopic | | | | |
| Day 16, 8 AM Percent Change from Baseline ANCOVA [1] | | | −22.79 (−29.25, −16.32) | <0.0001 |
| Least-squares mean (SE) | −18.78 (2.323) | 4.01 (2.264) | | |
| p-value [2] | <0.0001 | 0.0807 | | |

Min = Minimum, Max = Maximum, SD = Standard deviation, LS = Least-squares, CI = Confidence interval, SE = Standard error
[1] For an analysis of covariance (ANCOVA) with (percent) change from Baseline in Pupil Diameter as the dependent variable; treatment as a factor; and Baseline Pupil Diameter as the covariate.
[2] From a test comparing the individual treatment change from baseline LS mean to zero.

TABLE 7A

Observed Change in Pupil Diameter Under Mesopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Mesopic | | | | |
| Day 15, 8 AM Change from Baseline ANCOVA [1] | | | −0.89 (−1.15, −0.63) | <0.0001 |
| Least-squares mean (SE) | −1.02 (0.094) | −0.14 (0.092) | | |
| p-value [2] | <0.0001 | 0.1424 | | |
| Day 15, 8 AM Percent Change from Baseline | | | | |
| n | 38 | 40 | | |
| Mean (SD) | −21.65 (11.281) | −2.03 (14.024) | | |
| Median | −20.22 | −2.93 | | |
| Min, Max | −38.6, 1.8 | −22.5, 48.8 | | |
| Day 15, 8 AM Percent Change from Baseline ANCOVA [1] | | | −19.25 (−24.93, −13.57) | <0.0001 |
| Least-squares mean (SE) | −21.46 (2.039) | −2.21 (1.988) | | |
| p-value [2] | <0.0001 | 0.2707 | | |

Min = Minimum, Max = Maximum, SD = Standard deviation, LS = Least-squares, CI = Confidence interval, SE = Standard error
[1] For an analysis of covariance (ANCOVA) with (percent) change from Baseline in Pupil Diameter as the dependent variable; treatment as a factor; and Baseline Pupil Diameter as the covariate.
[2] From a test comparing the individual treatment change from baseline LS mean to zero.
[3] The pooled data from the Study Eye and Fellow Eye.

TABLE 7B

Observed Change in Pupil Diameter Under Mesopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| All Eyes [3] Mesopic Day 16, 8 AM Percent Change from Baseline | | | | |
| n | 38 | 40 | | |
| Mean (SD) | −19.09 (11.478) | −1.59 (13.521) | | |
| Median | −19.10 | −2.14 | | |
| Min, Max | −39.0, 1.0 | −24.9, 46.8 | | |
| Day 16, 8 AM Percent Change from Baseline ANCOVA [1] | | | −17.07 (−22.62, −11.53) | <0.0001 |

TABLE 7B-continued

Observed Change in Pupil Diameter Under Mesopic Conditions

| Eye Light Condition Visit Statistic | 1% w/w Phentolamine Mesylate Ophthalmic Solution (N = 19) | Placebo (N = 20) | 1% w/w Phentolamine Mesylate Ophthalmic Solution vs. Placebo [1] LS Mean Difference (95% CI) | p-value |
|---|---|---|---|---|
| Least-squares mean (SE) | −18.87 (1.991) | −1.79 (1.941) | | |
| p-value [2] | <0.0001 | 0.3581 | | |

Min = Minimum, Max = Maximum, SD = Standard deviation, LS = Least-squares, CI = Confidence interval, SE = Standard error
[1] For an analysis of covariance (ANCOVA) with (percent) change from Baseline in Pupil Diameter as the dependent variable; treatment as a factor; and Baseline Pupil Diameter as the covariate.
[2] From a test comparing the individual treatment change from baseline LS mean to zero.
[3] The pooled data from the Study Eye and Fellow Eye.

The observed change in near visual acuity in the human subjects measured on days 15 and 16 is listen in Tables 8 and 9.

TABLE 8

Observed Change in Near Visual Acuity

| Eye Light Condition Visit Category [1] | 1% w/w Phentolamine Mesylate Ophthalmic Solution (N = 19) n (%) | Placebo (N = 20) n (%) | 1% w/w Phentolamine Mesylate Ophthalmic Solution vs. Placebo [2] Odds Ratio (95% CI) | p-value |
|---|---|---|---|---|
| All Eyes [3] Photopic Day 8, 8 AM | | | | |
| n | 19 | 20 | | |
| >=1 line | 12 (63.2) | 5 (25.0) | 6.17 (1.81, 24.91) | 0.0018 |
| >=2 lines | 4 (21.1) | 3 (15.0) | 2.03 (0.37, 14.10) | 0.5678 |
| >=3 lines | 2 (10.5) | 1 (5.0) | 1.44 (0.05, 112.24) | 1.0000 |
| Day 15, 8 AM | | | | |
| n | 19 | 20 | | |
| >=1 line | 13 (68.4) | 8 (40.0) | 4.13 (1.41, 12.88) | 0.0072 |
| >=2 lines | 4 (21.1) | 1 (5.0) | 4.73 (0.44, 245.09) | 0.3054 |
| >=3 lines | 2 (10.5) | 0 | 0.76 (0.04, >999.99) | 1.0000 |
| Day 16, 8 AM | | | | |
| n | 19 | 20 | | |
| >=1 line | 14 (73.7) | 9 (45.0) | 3.72 (1.24, 11.91) | 0.0163 |
| >=2 lines | 8 (42.1) | 2 (10.0) | 6.92 (1.23, 73.03) | 0.0232 |
| >=3 lines | 4 (21.1) | 1 (5.0) | 2.51 (0.15, 150.96) | 0.8354 |

CI = Confidence interval. Percentages are the number of subjects achieving the improvement divided by the number of subjects with an assessment at the timepoint.
[1] 1 line = 1.3 LogMAR; 2 lines = 1.2 LogMAR; 3 lines = 1.1 LogMAR, etc.
[2] From a logistic regression with treatment as a factor; and Baseline DCNVA as the covariate.
[3] The pooled data from the Study Eye and Fellow Eye. Subjects are counted in a category if they meet the reduction criterion for at least one eye.

TABLE 9

Observed Change in Near Visual Acuity

| Eye Light Condition Visit Category [1] | 1% w/w Phentolamine Mesylate Ophthalmic Solution (N = 19) n (%) | Placebo (N = 20) n (%) | 1% w/w Phentolamine Mesylate Ophthalmic Solution vs. Placebo [2] Odds Ratio (95% CI) | p-value |
|---|---|---|---|---|
| All Eyes [3] Mesopic Day 8, 8 AM | | | | |
| n | 19 | 20 | | |
| >=1 line | 9 (47.4) | 7 (35.0) | 1.71 (0.58, 5.14) | 0.3967 |
| >=2 lines | 3 (15.8) | 1 (5.0) | 2.92 (0.20, 165.98) | 0.6911 |
| >=3 lines | 0 | 0 | | |

TABLE 9-continued

Observed Change in Near Visual Acuity

| Eye Light Condition Visit Category [1] | 1% w/w Phentolamine Mesylate Ophthalmic Solution (N = 19) n (%) | Placebo (N = 20) n (%) | 1% w/w Phentolamine Mesylate Ophthalmic Solution vs. Placebo [2] Odds Ratio (95% CI) | p-value |
|---|---|---|---|---|
| Day 15, 8 AM | | | | |
| n | 19 | 20 | | |
| >=1 line | 13 (68.4) | 7 (35.0) | 4.21 (1.43, 13.34) | 0.0064 |
| >=2 lines | 5 (26.3) | 4 (20.0) | 1.57 (0.38, 6.92) | 0.6820 |
| >=3 lines | 0 | 0 | | |
| Day 16, 8 AM | | | | |
| n | 19 | 20 | | |
| >=1 line | 12 (63.2) | 9 (45.0) | 2.60 (0.92, 7.73) | 0.0752 |
| >=2 lines | 8 (42.1) | 2 (10.0) | 4.11 (0.89, 26.28) | 0.0750 |
| >=3 lines | 3 (15.8) | 0 | 4.92 (0.77, >999.99) | 0.1627 |

CI = Confidence interval. Percentages are the number of subjects achieving the improvement divided by the number of subjects with an assessment at the timepoint.
[1] 1 line = 1.3 LogMAR; 2 lines = 1.2 LogMAR; 3 lines = 1.1 LogMAR, etc.
[2] From a logistic regression with treatment as a factor; and Baseline DCNVA as the covariate.
[3] The pooled data from the Study Eye and Fellow Eye. Subjects are counted in a category if they meet the reduction criterion for at least one eye.

The observed change in eye redness in the human subjects measured on days 15 and 16 is listed in Tables 10A, 10B, 10C, and 10D. An overall summary of treatment emergent adverse events observed during the study is provided in Table 11.

TABLE 10A

Observed Change in Eye Redness

| Eye Timepoint Category | 1% w/w Phentolamine Mesylate Ophthalmic Solution (N = 19) n (%) | Placebo (N = 20) n (%) | Total (N = 39) n (%) |
|---|---|---|---|
| Study Eye Baseline, 8 AM | | | |
| n | 19 | 20 | 39 |
| None | 9 (47.4) | 9 (45.0) | 18 (46.2) |
| Mild | 9 (47.4) | 7 (35.0) | 16 (41.0) |
| Moderate | 1 (5.3) | 3 (15.0) | 4 (10.3) |
| Severe | 0 | 1 (5.0) | 1 (2.6) |
| Numeric Scale [1] | | | |
| n | 19 | 20 | 39 |
| Mean (SD) | 0.6 (0.61) | 0.8 (0.89) | 0.7 (0.77) |
| Median | 1.0 | 1.0 | 1.0 |
| Min, Max | 0, 2 | 0, 3 | 0, 3 |
| Baseline, 10 AM | | | |
| n | 19 | 20 | 39 |
| None | 10 (52.6) | 8 (40.0) | 18 (46.2) |
| Mild | 8 (42.1) | 9 (45.0) | 17 (43.6) |
| Moderate | 1 (5.3) | 3 (15.0) | 4 (10.3) |
| Severe | 0 | 0 | 0 |

Percentages are the number of subjects in the category divided by the number of subjects with an examination at the timepoint.
[1] Conjunctival redness is graded on a 4-point scale: 0 = none; 1 = mild; 2 = moderate; 3 = severe.

TABLE 10B

Observed Change in Eye Redness

| Eye Timepoint Category | 1% w/w Phentolamine Mesylate Ophthalmic Solution (N = 19) n (%) | Placebo (N = 20) n (%) | Total (N = 39) n (%) |
|---|---|---|---|
| Study Eye Day 15, 8 AM | | | |
| n | 19 | 20 | 39 |
| None | 4 (21.1) | 8 (40.0) | 12 (30.8) |
| Mild | 10 (52.6) | 8 (40.0) | 18 (46.2) |
| Moderate | 3 (15.8) | 4 (20.0) | 7 (17.9) |
| Severe | 2 (10.5) | 0 | 2 (5.1) |
| Numeric Scale [1] | | | |
| n | 19 | 20 | 39 |
| Mean (SD) | 1.2 (0.90) | 0.8 (0.77) | 1.0 (0.84) |
| Median | 1.0 | 1.0 | 1.0 |
| Min, Max | 0, 3 | 0, 2 | 0, 3 |
| Day 15, 10 AM | | | |
| n | 19 | 20 | 39 |
| None | 5 (26.3) | 8 (40.0) | 13 (33.3) |
| Mild | 10 (52.6) | 8 (40.0) | 18 (46.2) |
| Moderate | 2 (10.5) | 4 (20.0) | 6 (15.4) |
| Severe | 2 (10.5) | 0 | 2 (5.1) |

Percentages are the number of subjects in the category divided by the number of subjects with an examination at the timepoint.
[1] Conjunctival redness is graded on a 4-point scale: 0 = none; 1 = mild; 2 = moderate; 3 = severe.

TABLE 10C

Observed Change in Eye Redness

| Eye Timepoint Category | 1% w/w Phentolamine Mesylate Ophthalmic Solution (N = 19) n (%) | Placebo (N = 20) n (%) | Total (N = 39) n (%) |
|---|---|---|---|
| Fellow Eye Baseline, 8 AM | | | |
| n | 19 | 20 | 39 |
| None | 9 (47.4) | 8 (40.0) | 17 (43.6) |
| Mild | 9 (47.4) | 9 (45.0) | 18 (46.2) |

TABLE 10C-continued

Observed Change in Eye Redness

| Eye Timepoint Category | 1% w/w Phentolamine Mesylate Ophthalmic Solution (N = 19) n (%) | Placebo (N = 20) n (%) | Total (N = 39) n (%) |
|---|---|---|---|
| Moderate | 1 (5.3) | 3 (15.0) | 4 (10.3) |
| Severe | 0 | 0 | 0 |
| Numeric Scale [1] | | | |
| n | 19 | 20 | 39 |
| Mean (SD) | 0.6 (0.61) | 0.8 (0.72) | 0.7 (0.66) |
| Median | 1.0 | 1.0 | 1.0 |
| Min, Max | 0, 2 | 0, 2 | 0, 2 |
| Baseline, 10 AM | | | |
| n | 19 | 20 | 39 |
| None | 10 (52.6) | 7 (35.0) | 17 (43.6) |
| Mild | 8 (42.1) | 10 (50.0) | 18 (46.2) |
| Moderate | 1 (5.3) | 3 (15.0) | 4 (10.3) |
| Severe | 0 | 0 | 0 |

Percentages are the number of subjects in the category divided by the number of subjects with an examination at the timepoint.
[1] Conjunctival redness is graded on a 4-point scale: 0 = none; 1 = mild; 2 = moderate; 3 = severe.

TABLE 10D

Observed Change in Eye Redness

| Eye Timepoint Category | 1% w/w Phentolamine Mesylate Ophthalmic Solution (N = 19) n (%) | Placebo (N = 20) n (%) | Total (N = 39) n (%) |
|---|---|---|---|
| Fellow Eye Day 15, 8 AM | | | |
| n | 19 | 20 | 39 |
| None | 6 (31.6) | 9 (45.0) | 15 (38.5) |
| Mild | 9 (47.4) | 7 (35.0) | 16 (41.0) |
| Moderate | 2 (10.5) | 4 (20.0) | 6 (15.4) |
| Severe | 2 (10.5) | 0 | 2 (5.1) |
| Numeric Scale [1] | | | |
| n | 19 | 20 | 39 |
| Mean (SD) | 1.0 (0.94) | 0.8 (0.79) | 0.9 (0.86) |
| Median | 1.0 | 1.0 | 1.0 |
| Min, Max | 0, 3 | 0, 2 | 0, 3 |
| Day 15, 10 AM | | | |
| n | 19 | 20 | 39 |
| None | 6 (31.6) | 8 (40.0) | 14 (35.9) |
| Mild | 9 (47.4) | 8 (40.0) | 17 (43.6) |
| Moderate | 2 (10.5) | 4 (20.0) | 6 (15.4) |
| Severe | 2 (10.5) | 0 | 2 (5.1) |

Percentages are the number of subjects in the category divided by the number of subjects with an examination at the timepoint.
[1] Conjunctival redness is graded on a 4-point scale: 0 = none; 1 = mild; 2 = moderate; 3 = severe.

TABLE 11

Overall Summary of Treatment Emergent Adverse Events

| Adverse Events | 1% w/w Phentolamine Mesylate Ophthalmic Solution (N = 19) n (%) | Placebo (N = 20) n (%) | Total (N = 39) n (%) |
|---|---|---|---|
| Total Number of TEAEs [1] | 16 | 2 | 18 |
| Subjects Reporting Any TEAE | 6 (31.6) | 1 (5.0) | 7 (17.9) |
| Subjects Reporting TEAE by Maximum Severity | | | |
| Mild | 6 (31.6) | 1 (5.0) | 7 (17.9) |
| Moderate | 0 | 0 | 0 |
| Severe | 0 | 0 | 0 |
| Subjects Reporting TEAE by Greatest Relationship | | | |
| Not Related | 1 (5.3) | 0 | 1 (2.6) |
| Possibly Related | 0 | 0 | 0 |
| Related | 5 (26.3) | 1 (5.0) | 6 (15.4) |
| Subjects Reporting Any Serious TEAE | 0 | 0 | 0 |
| Subjects Reporting Any TEAE Leading to Withdrawal from the Study | 0 | 0 | 0 |
| Subjects Reporting Any TEAE Leading to Study Medication Discontinuation | 0 | 0 | 0 |
| Subject Deaths | 0 | 0 | 0 |

Percentages are the number of subjects in the category divided by the number of subjects randomized in the group.
[1] In counting the number of adverse events reported, an adverse event is defined as an event with a unique subject identification number, system organ class, preferred term, and site. Bilateral ocular events are counted twice, i.e. once for each eye.

Example 6-Reduction in Intraocular Pressure by Phentolamine Mesylate in Human Subjects Pharmacologically Induced Mydriasis Ability of phentolamine mesylate to reduce intraocular pressure in the eye of human subjects with pharmacologically induced mydriasis was evaluated according to a clinical study in which placebo or an aqueous ophthalmic solution containing phentolamine mesylate was administered to the eye of a patient having pharmacologically induced mydriasis, and then the patient was evaluated for reduction in intraocular pressure in the eye. In the procedure, one drop test article (i.e., placebo or 1% w/w Phentolamine Mesylate Ophthalmic Solution) was administered to the patient's eye. The clinical study was conducted as a placebo-controlled, randomized, double-masked, 2-arm cross-over, Phase 2b study in 32 randomized human subjects. Approximately one-half of the randomized subjects received phenylephrine 1 hour before treatment with 1% w/w Phentolamine Mesylate Ophthalmic Solution and approximately one-half received tropicamide 1 hour before treatment with 1% w/w Phentolamine Mesylate Ophthalmic Solution. Each subject received the same mydriatic agent throughout the study. Intraocular pressure (IOP) of the subject's eye was measured before administration of the test article (i.e., placebo or 1% w/w Phentolamine Mesylate Ophthalmic Solution) and then again 2-3 hours and at 6 hours after administration of test article. Study medication is further described in Table 1 below.

TABLE 1

Study Medication

| Study Medication | Composition of Study Medication |
| --- | --- |
| 1% w/w Phentolamine Mesylate Ophthalmic Solution | 1% w/w phentolamine mesylate<br>4% w/w mannitol<br>3 mM buffer comprising sodium acetate and acetic acid<br>water<br>pH in the range 4.8 to 5.0 |
| Placebo Ophthalmic Solution | 4% w/w mannitol<br>3 mM buffer comprising sodium acetate and acetic acid<br>water<br>pH in the range 4.8 to 5.0 |

Observed experimental results from the IOP measurements are provided in Tables 2 and 3 below.

TABLE 2

| | 1% w/w Phentolamine Mesylate Ophthalmic Solution | | | | |
| --- | --- | --- | --- | --- | --- |
| Patient Characteristics* | | Average | | | |
| IOP Baseline (mmHg)** | Average Baseline Diurnal IOP (mmHg) | n (number of eyes) | Change in IOP from Baseline (mmHg) | Min | Max |
| <22 | 15.2 | 62 | −1.35 | −10 | 3 |
| <20 | 15.1 | 60 | −1.28 | −10 | 3 |
| <19 | 14.8 | 55 | −1.09 | −7 | 3 |
| <18 | 14.2 | 48 | −1.06 | −7 | 3 |
| <17 | 13.5 | 38 | −1.00 | −6 | 2 |
| <16 | 13 | 32 | −0.75 | −4 | 2 |
| <15 | 12.3 | 24 | −1.13 | −4 | 2 |
| <14 | 11.5 | 16 | −1.44 | −4 | 2 |
| <13 | 11.2 | 13 | −1.54 | −4 | 2 |
| <12 | 10.8 | 9 | −1.67 | −4 | 2 |

*Per protocol.
**As measured at Week 1 Baseline; changes measured at 6-8 hours post dose.

TABLE 3

| | Placebo | | | | | |
| --- | --- | --- | --- | --- | --- | --- |
| Patient Characteristics* | | Average | | | | |
| IOP Baseline (mmHg)** | Average Baseline Diurnal IOP (mmHg) | n (number of eyes) | Change in IOP from Baseline (mmHg) | Min | Max | p value |
| <22 | 15.2 | 62 | −0.65 | −6 | 3 | 0.0803 |
| <20 | 15.1 | 60 | −0.50 | −5 | 3 | 0.047 |
| <19 | 14.8 | 55 | −0.40 | −5 | 3 | 0.0767 |
| <18 | 14.2 | 48 | −0.25 | −5 | 3 | 0.0471 |
| <17 | 13.5 | 38 | −0.18 | −5 | 3 | 0.0734 |
| <16 | 13 | 32 | 0.00 | −5 | 3 | 0.1276 |
| <15 | 12.3 | 24 | −0.13 | −5 | 3 | 0.1078 |
| <14 | 11.5 | 16 | 0.06 | −4 | 3 | 0.0446 |
| <13 | 11.2 | 13 | 0.38 | −4 | 3 | 0.0094 |
| <12 | 10.8 | 9 | 0.56 | −1 | 3 | 0.0119 |

*Per protocol.
**As measured at Week 1 Baseline; changes measured at 6-8 hours post dose.

Example 7-Reduction in Intraocular Pressure by Phentolamine Mesylate in Combination with Latanoprost in Human Subjects with Open-Angle Glaucoma or Ocular Hypertension Ability of phentolamine mesylate to reduce intraocular pressure in the eye of a human subject with bilateral open-angle glaucoma (OAG) or ocular hypertension (OHT) alone or combination with latanoprost may be evaluated according to a clinical study in which an aqueous ophthalmic solution containing phentolamine mesylate is administered to the eye of a patient in combination with latanoprost, and then the patient is evaluated for reduction in intraocular pressure in the eye that received the phentolamine mesylate and latanoprost. Subjects with either OAG or OHT may be randomized in a 1:1:1 ratio to receive (i) 1% w/w Phentolamine Mesylate Ophthalmic Solution Containing 0.005% w/w Latanoprost, (ii) just 1% w/w Phentolamine Mesylate Ophthalmic Solution, or (iii) just 0.005% w/w Latanoprost Ophthalmic Solution once daily in the evening. Efficacy evaluations of intraocular pressure (IOP) are to take place at the Baseline and the Treatment-study Visit days (week 2, week 6, and month 3) at 8 AM, 10 AM, and 4 PM. As an alternative to administering 1% w/w Phentolamine Mesylate Ophthalmic Solution Containing 0.005% w/w Latanoprost, the study may administer (a) 1% w/w Phentolamine Mesylate Ophthalmic Solution and (b) 0.005% w/w Latanoprost Ophthalmic Solution. Further experimental procedures are provided below.

Part I—Experimental Procedures

The study is to be configured as a double-masked, active-controlled, parallel-group, randomized clinical trial. Human subjects are to be screened for potential enrollment and, if qualified, enrolled in the study. Eligible patients will have bilateral open-angle glaucoma or ocular hypertension and are aged ≥18 years with unmedicated IOP between 20 and 36 mmHg (i.e., >20 mmHg and <36 mm Hg) in both eyes at 8:00 AM at two qualification visits (2-7 days apart) and between 17 mmHg and 36 mmHg (i.e., an IOP >17 mmHg and <36 mm Hg) in both eyes at 10:00 AM and 4:00 PM at the second qualification visit. Patients using ocular hypotensive medications will be required to undergo washout before study entry: 4 weeks for prostaglandin analogs and β-adrenergic antagonists, 2 weeks for adrenergic agonists, and 5 days for muscarinic agonists and carbonic anhydrase inhibitors. Best-corrected visual acuity in each eye will be +1.0 logMAR or better by Early Treatment of Diabetic Retinopathy Study measurement.

Exclusion criteria include individuals treated with greater than two ocular hypotensive medications within 30 days of screening, pseudoexfoliation or pigment dispersion glaucoma, a history of iridocorneal angle closure or narrow angles (including previous peripheral iridotomy), previous glaucoma incisional or laser surgery, previous refractive surgery, central corneal thickness >620 μm, or known hypersensitivity or contraindications to phentolamine mesylate or latanoprost (or their excipients). Patients with clinically significant ocular disease other than glaucoma in either eye or systemic disease that might interfere with the study, and women of childbearing potential who were pregnant, nursing, planning a pregnancy, or not using a medically acceptable form of birth control will also excluded.

Enrolled patients will be randomized (1:1:1) via an interactive web-based response system to receive 1% w/w Phentolamine Mesylate Ophthalmic Solution Containing 0.005% w/w Latanoprost 0.005%, only 1% w/w Phentolamine Mesylate Ophthalmic Solution, or only 0.005% w/w Latanoprost Ophthalmic Solution. Each study treatment will be dosed once daily in the evening. Randomization will be stratified by maximum baseline IOP (<25 vs ≥25 mm Hg). Treatment assignments will be masked to the investigator, clinical study team, and patients. An independent person at the investigative site not responsible for performing any study procedure will be assigned to dispense, collect, and store study treatment. As an alternative to administering 1% w/w Phentolamine Mesylate Ophthalmic Solution Containing 0.005% w/w Latanoprost, the study may administer (a) 1% w/w Phentolamine Mesylate Ophthalmic Solution and (b) 0.005% w/w Latanoprost Ophthalmic Solution. Exemplary study medication is further described in the following table.

| Exemplary Study Medication | |
|---|---|
| Study Medication | Composition of Study Medication |
| 1% w/w Phentolamine Mesylate Ophthalmic Solution Containing 0.005% w/w Latanoprost | 1% w/w phentolamine mesylate 0.005% w/w latanoprost 4% w/w mannitol 3 mM buffer comprising sodium acetate and acetic acid water pH in the range 4.8 to 5.0 |
| 1% w/w Phentolamine Mesylate Ophthalmic Solution | 1% w/w phentolamine mesylate 4% w/w mannitol 3 mM buffer comprising sodium acetate and acetic acid water pH in the range 4.8 to 5.0 |
| 0.005% w/w Latanoprost Ophthalmic Solution | 0.005% w/w latanoprost buffer water having a pH of, for example, about 6.7. |

An exemplary 0.005% w/w Latanoprost Ophthalmic Solution is, for example, latanoprost ophthalmic solution available commercially under the tradename XALATAN©, which contains 0.005% w/w latanoprost as a sterile, isotonic, buffered aqueous solution having a pH of approximately 6.7 and an osmolality of approximately 267 mOsmol/kg. Each 1 mL of XALATAN© solution contains 50 micrograms of latanoprost. Inactive ingredients in the XALATAN© solution are sodium chloride, sodium dihydrogen phosphate monohydrate, disodium hydrogen phosphate anhydrous, water for injection, and benzalkonium chloride (0.02% w/w) which functions as a preservative. One drop of XALATAN© solution contains approximately 1.5 micrograms of latanoprost.

Analysis of Efficacy

The primary efficacy endpoint is mean IOP at 8:00 AM, 10:00 AM, and 4:00 PM at week 2, week 6, and month 3. Secondary efficacy endpoints include mean diurnal IOP, mean change and mean percent change from diurnally adjusted (time-consistent) baseline IOP, and percentages of patients achieving pre-specified thresholds for mean, mean change, and mean percent change in mean diurnal IOP. Both eyes will be treated; the study eye is the eye with higher IOP at 8:00 AM on day 1, or the OD eye if IOP is the same in both eyes. The intent-to-treat population includes all randomized patients who received ≥1 dose of study medication and is the primary population for efficacy analyses. The per-protocol population is the subset of patients in the intent-to-treat population who will not have major protocol violations and is the secondary population for efficacy analyses.

Analysis of Safety

Safety outcomes measures are ocular and systemic adverse events (AEs) during the 3-month treatment period. Safety outcomes for the total study duration (3 months) will be reported separately. Safety and tolerability will be assessed using patient responses to open-ended questions (e.g., "How are you feeling?") and ophthalmic and systemic examinations. Ocular safety assessments, which will be undertaken at all study time points, include symptoms and AEs, best-corrected visual acuity (Early Treatment of Diabetic Retinopathy Study measurement), pupil size, biomicroscopy, pachymetry, visual field and cup-disc ratio measurements, and dilated ophthalmoscopy. Biomicroscopic examination of the eyelids, conjunctiva, cornea, anterior chamber, lens, iris, and pupil of both eyes will be performed at every study visit. Systemic safety assessments include measurements of heart rate, and blood pressure. Trial can be extended for up to 12 months for further safety exposure data.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

The invention claimed is:

1. A method of treating a condition selected from the group consisting of glaucoma and ocular hypertension in a human patient while minimizing eye redness during the patient's waking hours, comprising topically administering in the form of an eye drop to an eye of the patient in need thereof at or near the bedtime of the patient a once daily dosage of phentolamine mesylate in the amount of from about 0.3 mg to about 0.7 mg to thereby treat the condition.

2. The method of claim 1, further comprising administering to the eye of the patient a second therapeutic agent selected from the group consisting of a prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor.

3. The method of claim 1, further comprising administering to the eye of the patient a second therapeutic agent selected from the group consisting of latanoprost, bimatoprost, travoprost, tafluprost, latanoprostene bunod, timolol, brimonidine, dorzolamide, brinzolamide, acetazolamide, methazolamide, pilocarpine, netarsudil, ripasudil, AMA0076, trabodenoson, BOL-303259-X, ONO-9054, carbachol, aceclidine, and oxotremorine, or a pharmaceutically acceptable salt of any one of the foregoing.

4. The method of claim 3, wherein the second therapeutic agent is latanoprost.

5. The method of claim 3, wherein the second therapeutic agent is latanoprost administered at a daily dose of about 1.5 micrograms.

6. The method of claim 1, wherein the dosage contains about 0.5 mg of phentolamine mesylate.

7. The method of claim 1, wherein the patient experiences at least a 10% reduction in intraocular pressure in the eye due to the administering.

8. The method of claim 7, wherein the reduction lasts for a duration of at least 12 hours.

9. The method of claim 7, wherein the patient to begin treatment is characterized as having an intraocular pressure less than 26 mmHg.

10. The method of claim 1, wherein the patient experiences at least a 2 mmHg reduction in intraocular pressure in the eye due to the administering.

11. The method of claim 1, wherein the patient experiences at least a 4 mmHg reduction in intraocular pressure in the eye due to the administering.

12. The method of claim 1, wherein the condition is glaucoma.

13. The method of claim 12, wherein the glaucoma is closed-angle glaucoma.

14. The method of claim 12, wherein the glaucoma is normal tension glaucoma.

15. The method of claim 1, wherein the condition is ocular hypertension.

16. The method of claim 1, wherein the patient to begin treatment is characterized as having an intraocular pressure less than 26 mmHg.

17. A method of treating a condition selected from the group consisting of glaucoma and ocular hypertension in a human patient according to a monotherapy treatment regimen, comprising topically administering in the form of an eye drop to an eye of the patient in need thereof a dosage of a single therapeutic agent in an amount of from about 0.3 mg to about 0.7 mg, wherein the single therapeutic agent is phentolamine mesylate.

18. A method of treating a condition selected from the group consisting of glaucoma and ocular hypertension in a human patient, comprising topically administering to an eye of the patient in need thereof (i) phentolamine mesylate in the amount of from about 0.3 mg to about 0.7 mg and (ii) a therapeutically effective dosage of a second therapeutic agent selected from the group consisting of a prostaglandin analog, a beta blocker, an alpha adrenergic agonist, a carbonic anhydrase inhibitor, a cholinergic agonist, NMDA receptor antagonist, adenosine receptor agonist, 5-$HT_{2A}$ receptor agonist, and a Rho kinase inhibitor, to thereby treat the condition.

19. The method of claim 18, wherein the second therapeutic agent is latanoprost.

20. The method of claim 18, wherein the second therapeutic agent is latanoprost administered at a daily dose of about 1.5 micrograms.

* * * * *